US010206961B2

(12) United States Patent
Gruber et al.

(10) Patent No.: US 10,206,961 B2
(45) Date of Patent: Feb. 19, 2019

(54) PROCESS FOR PREPARING METABOLIZED CONDITIONED GROWTH MEDIA

(71) Applicant: Allergan, Inc., Irvine, CA (US)

(72) Inventors: James Vincent Gruber, Washington, NJ (US); Smitha Rao, Hillsborough, NJ (US); Rahul Mehta, San Marcos, CA (US); Sujatha D. Sonti, San Marcos, CA (US)

(73) Assignee: Allergan, Inc., Irvine, CA (US)

( * ) Notice: Subject to any disclaimer, the term of this patent is extended or adjusted under 35 U.S.C. 154(b) by 186 days.

(21) Appl. No.: 14/047,929

(22) Filed: Oct. 7, 2013

(65) Prior Publication Data

US 2014/0045240 A1 Feb. 13, 2014

Related U.S. Application Data

(63) Continuation of application No. 13/294,599, filed on Nov. 11, 2011.

(60) Provisional application No. 61/413,166, filed on Nov. 12, 2010.

(51) Int. Cl.
A61K 36/06 (2006.01)
A61K 8/99 (2017.01)
A61K 35/33 (2015.01)
C12P 1/02 (2006.01)
A61K 36/064 (2006.01)
A61Q 7/00 (2006.01)
A61Q 19/00 (2006.01)
A61Q 19/02 (2006.01)
A61Q 19/08 (2006.01)
A61K 8/9706 (2017.01)

(52) U.S. Cl.
CPC ............ A61K 36/06 (2013.01); A61K 8/9706 (2017.08); A61K 8/99 (2013.01); A61K 35/33 (2013.01); A61K 36/064 (2013.01); A61Q 7/00 (2013.01); A61Q 19/00 (2013.01); A61Q 19/001 (2013.01); A61Q 19/02 (2013.01); A61Q 19/08 (2013.01); C12P 1/02 (2013.01); A61K 2800/522 (2013.01)

(58) Field of Classification Search
None
See application file for complete search history.

(56) References Cited

U.S. PATENT DOCUMENTS

| 4,721,096 A | 1/1988 | Naughton et al. |
| 4,963,489 A | 10/1990 | Naughton et al. |
| 5,032,508 A | 1/1991 | Naughton et al. |
| 5,160,790 A | 11/1992 | Naughton et al. |
| 5,266,780 A | 11/1993 | Naughton et al. |
| 5,460,939 A | 10/1995 | Hansbrough et al. |
| 5,462,860 A | 10/1995 | Mach |
| 5,516,521 A | 5/1996 | Atala et al. |
| 5,559,022 A | 9/1996 | Naughton et al. |
| 5,654,381 A | 8/1997 | Hrkach et al. |
| 5,709,854 A | 1/1998 | Griffith-Cima et al. |
| 5,763,267 A | 6/1998 | Kurjan et al. |
| 5,785,964 A | 7/1998 | Naughton et al. |
| 5,843,766 A | 12/1998 | Applegate et al. |
| 6,372,494 B1* | 4/2002 | Naughton ............... A61K 8/02 424/115 |
| 7,118,746 B1 | 10/2006 | Naughton et al. |
| 7,160,726 B2 | 1/2007 | Mansbridge |
| 8,138,147 B2 | 3/2012 | Naughton et al. |
| 8,361,485 B2 | 1/2013 | Naughton et al. |
| 2003/0198682 A1* | 10/2003 | Gruber .................... A61K 8/11 424/493 |
| 2003/0235559 A1 | 12/2003 | Sobol et al. |
| 2004/0001814 A1 | 1/2004 | Cheung |
| 2004/0253262 A1 | 12/2004 | Cheung |
| 2012/0230940 A1 | 9/2012 | Naughton et al. |

FOREIGN PATENT DOCUMENTS

| JP | 50126872 A | * | 10/1975 |
| JP | 07-010734 | | 1/1995 |
| KR | 20080036315 A | * | 4/2008 |
| SU | 1142451 A | * | 2/1985 |
| WO | 1993/017669 | | 9/1993 |
| WO | 1994/025080 | | 11/1994 |

(Continued)

OTHER PUBLICATIONS

Merkel et al. Infection and Immunity. vol. 56, No. 4. (Apr. 1988) p. 792-801.*
Beam, C. "The Rise of Yeast: Why do scientists always experiment on this fungus?". Web Publication Date: May 6, 2009. [Retrieved from the Internet on: Jan. 4, 2018]. Retrieved from: <URL: http://www.slate.com/articles/news_and_politics/explainer/2009/05/the_rise_of_yeast.html>. (Year: 2009).*
Neeman M, Abramovitch R. et al. "Regulation of angiogenesis by hypoxic stress: from solid tumors to ovarian follicle," Int J. Exp Path 78:57-70, 1997.
Brigham et al. "The stumptailed macaque as a model for androgenic alopecia: effects of topical minoxidil analyzed by use of the folliculogram," Clin Dermatol 6:177-87, 1988.

(Continued)

Primary Examiner — Amy L Clark
(74) Attorney, Agent, or Firm — Laura L. Wine

(57) ABSTRACT

Compositions comprising metabolized conditioned growth medium and/or metabolized cell extract and methods of use are described. The metabolized conditioned growth medium and metabolized cell extract compositions may be formulated with an acceptable carrier into injectable or topical formulations, for example, as a cream, lotion or gel, and may be used in cosmeceutical or pharmaceutical applications. The metabolized conditioned growth medium and metabolized cell extract may also be further processed to concentrate or reduce one or more factors or components contained within the metabolized conditioned growth medium or metabolized cell extract. The growth medium may be conditioned by any eukaryotic cell. The metabolized conditioned growth medium and metabolized cell extract may be used to prevent or treat a condition, for example, a skin condition.

2 Claims, 6 Drawing Sheets

(56) References Cited

FOREIGN PATENT DOCUMENTS

| WO | 1996/039101 | 12/1996 |
|----|-------------|---------|
| WO | 1998/052543 | 11/1998 |
| WO | 2000/069449 | 11/2000 |
| WO | 2003/068161 | 8/2003 |

OTHER PUBLICATIONS

Diani et al. "Immunocytochemical localization of androgen receptors in the scalp of stumptail macaque monkey, a model of androgenic alopecia," Invest Dermaol 102:511-4, 1994.

Flax et al. "Exgraftable human neural stem cells respond to development cues, replace neurons, and express foreign genes," Nature Biotechnol 16:1033-39, 1998.

Freshney "Culture of animal cells. A manual of basic technique" 2nd Ed. A.R. Liss, Inc., New York, NY, Chapter 20, pp. 257-288, 1987.

Frisen et al. "Central nervous system stem cells in the embryo and adult," Cell Mol Life Sci 54:935-45, 1998.

Goey et al. "Inhibition of early murine hemopoietic progenitor cell proliferation after in vivo locoregional administration of transforming growth factor-beta 1," J Immunol 143:877-80, 1989.

Gonzalez-Rubio M et al. "Oxidative stress induces tyrosine phosphorylation of PDGF alpha- and beta-receptors and pp60c-src in mesangial cells," Kidney Int 50:164-73, 1996.

Grotendorst GR et al. "Stimulation of granulation tissue formation by platelet-derived growth factor in normal and diabetic rats," J. Clin Invest 76:2323-2329, 1985.

Haseloff et al. "Simple RNA enzymes with new and highly specific endoribonuclease activities," Nature 334:585-91, 1988.

Holland JM "Animal models of alopecia" Clin Dermatol 6:159-62, 1988.

Hussein AM "Protection against cytosine arabinoside-induced alopecia by minoxidil in a rat animal model," Int J Dermatol 34:470-3, 1995.

Ignotz et al. "Transforming growth factor-beta stimulates the expression of fibronectin and collagen and their incorporation into the extracellular matrix," J Biol Chem 261:4337-45, 1986.

Keller et al. "Human embryonic stem cells: the future is now," Nature Med 5:151-2, 1999.

Kohler et al. "Platelets as a source of fibroblast growth-promoting activity," Exp Cell Res 87:297-301, 1974.

Mackay et al. "Chondrogenic differentiation of cultured human mesenchymal stem cells from marrow," Tissue Eng 4:415-28, 1988.

Matsuda et al. "Photoinduced prevention of tissue adhesion," ASAIO Trans 38:154-57, 1992.

Matsuzaki et al; "Role of hair papilla cells on induction and regeneration processes of hair follicles," Wound Repair Regen 6:524-30, 1998.

McElwee et al. "In vivo depletion of CD8+ T cells restores hair growth in the DEBR model for alopecia areata," Br J Dermatol 135:211-7, 1996.

Michie HJ et al. "Immunobiological studies on the alopecic (DEBER) rat," Br J Dermatol 123:557-67, 1990.

Mombaerts et al. "Creation of a large genomic deletion at the T-cell antigen receptor beta-subunit locus in mouse embryonic stem cells by gene targeting," Proc Natl Acad Sci USA 88:3084-87, 1991.

Mustoe et al. "Accelerated healing of incisional wounds in rats induced by transforming growth factor-beta," Science 237:1333-6, 1987.

Naughton et al. "Hematopoiesis on nylon mesh templates. I. Long-term culture of rat bone marrow cells," J Med 18:219-50, 1987.

Neste DV "The growth of human hair in nude mice," Dermatol Clin 14:609-17, 1996.

Noda et al. "In vivo stimulation of bone formation by transforming growth factor-b," Endocrin 124:2991-5, 1989.

Oliver RF et al. "The DEBR rat model for alopecia areata," J Invest Dermatol 96:978, 1991.

Pan HJ et al. "Evaluation of RU58841 as an anti-androgen in prostate PC3 cells and a topical anti-alopecia agent in the bald scalp of stumptailed macaques," Endocrine 9:39-43, 1998.

PCT/US2011/060457 International Search Report dated Jun. 8, 2012.

Pierce GF et al. "In vivo incisional wound healing augmented by platelet-derived growth factor and recombinant c-sis gene homodimeric proteins," J Exp Med 167:974-87, 1988.

Pietenpol et al. "Transforming growth factor beta 1 suppression of c-myc gene transcription: role in inhibition of keratinocyte proliferation," Proc Natl Acad Sci USA 87:3758-62, 1990.

Pinney et al. "Human three-dimensional fibroblast cultures express angiogenic activity," J Cell Physiol 183:74-82, 2000.

Rittmaster RS et al. "The effects of N,N-diethyl-4-methyl-3-oxo-4-aza-5-alpha-androstane-17 beta-carboxamide, a 5 alpha-reductase inhibitor and antiandrogen, on the development of baldness in the stumptail macaque," J Clin Endocrinol Metab 65:188-93, 1987.

Ross R et al. "A platelet-dependent serum factor that stimulates the proliferation of arterial smooth muscle cells in vitro," Proc Natl Acad Sci USA 71:1207-10, 1974.

Seldon et al. "Implantation of genetically engineered fibroblasts into mice: implications for gene therapy," Science 236:714-18, 1987.

Shamblott et al. "Derivation of pluripotent stem cells from cultured human primordial stem cells," Proc Natl Acad Sci USA 95:13726-31, 1998.

Smith A "Cell therapy: in search of pluripotency," Curr Biol 8:R802-804, 1998.

Sporn MB et al. "Polypeptide transforming growth factors isolated from bovine sources and used for wound healing in vivo," Science 219:1329-31, 1983.

Stein et al. "Stabilization of vascular endothelial growth factor mRNA by hypoxia and hypoglycemia and coregulation with other ischemia-induced genes," Mol Cell Biol 15:5363-8, 1995.

Thomson et al. "Embryonic stem cell lines derived from human blastocyts," Science 282:1145-7, 1988.

Yao DL, West NR et al. "Cryogenic spinal cord injury induces astrocytic gene expression of insulin-like growth factor I and insulin-like growth factor binding protein 2 during myelin regeneration," J Neurosci Res 40:647-59, 1995.

Williams et al. "Cells isolated from adult human skeletal muscle capable of differentiating into multiple mesodermal pheonotypes," Am Surg 65:22-26, 1999.

Yang W et al. "A new role for vascular endothelial growth factor and fibroblast growth factors: increasing endothelial resistance to oxidative stress," FEBS Lett 403:139-42, 1997.

Zaug and Cech "The intervening sequence RNA of Tetrahymena is an enzyme," Science 231:470-5, 1986.

Zaug et al. "The labile phosphodiesterase bond at the ligation junction in a circular intervening sequence RNA," Science 224:574-8, 1984.

* cited by examiner

PROCESS FOR PREPARING METABOLIZED CONDITIONED GROWTH MEDIA

CROSS REFERENCE

This application is a continuation of U.S. patent application Ser. No. 13/294,599 filed Nov. 11, 2011, which claims the benefit of U.S. Provisional Application No. 61/413,166, filed Nov. 12, 2010, the entire disclosure of which is incorporated herein by reference in its entirety.

FIELD OF THE INVENTION

The disclosure relates to compositions comprising metabolized conditioned growth medium and/or metabolized cell extract, and methods for preventing or treating a condition, for example a skin condition, by administering the compositions to a subject.

BACKGROUND OF THE INVENTION

Culture medium compositions typically include essential amino acids, salts, vitamins, minerals, trace metals, sugars, lipids and nucleosides. Cell culture medium attempts to supply the components necessary to meet the nutritional needs required to grow cells in a controlled, artificial and in vitro environment. Nutrient formulations, pH, and osmolarity vary in accordance with parameters such as cell type, cell density, and the culture system employed. Many cell culture medium formulations are documented in the literature and a number of media are commercially available. Once the culture medium is incubated with cells, it is known to those skilled in the art as "spent" or "conditioned medium". Conditioned medium contains many of the original components of the medium, as well as a variety of cellular metabolites and secreted proteins, including, for example, growth factors, inflammatory mediators and other extracellular proteins.

SUMMARY OF THE INVENTION

In one embodiment, the disclosure provides a composition comprising metabolized conditioned growth medium and an acceptable carrier. In some embodiments, the metabolized conditioned growth medium is conditioned growth medium metabolized by yeast cells. In some embodiments, the conditioned growth medium is prepared by culturing cells in a growth medium sufficient to meet the nutritional needs required to grow the cells in vitro to form a conditioned growth medium. In other embodiments, the composition is a topical or injectable composition. In some embodiments, the composition is used to treat or prevent a skin condition. In other embodiments, the skin condition is a cosmetic defect, a congenital defect, hair loss or an acquired defect. In further embodiments, the skin condition is fine lines and wrinkles; age spots and dyspigmentation; decreased skin texture, tone and elasticity; roughness and photo damage; decreased ability of skin to regenerate itself; environmental damage; decreased smoothness and tightness of skin; age spots; fine and coarse lines and wrinkles; fine and coarse periocular wrinkles; nasolabial folds; facial fine and coarse lines; decreased skin radiance and evenness; decreased skin firmness; hyperpigmentation; dark spots and/or patches; decreased skin brightness and youthful appearance; photoaged skin; intrinsically and extrinsically aged skin; abnormal skin cellular turnover; decreased skin barrier; decrease of skin's ability to retain moisture; brown and red blotchiness; redness; abnormal skin epidermal thickness; reduction of dermal epidermal junction; increased pore size and number of pores; or a combination thereof. In one embodiment, the composition rejuvenates sun damaged and aging skin; improves the appearance of fine lines and wrinkles; promotes cell renewal; diminishes the appearance of age spots and dyspigmentation; improves skin tone, texture and elasticity; reduces roughness and photo damage; prevents or reduces environmental damage; plumps the skin; brightens the skin; lightens the skin; strengthens the ability of skin to regenerate itself; improves the appearance of age spots; brightens and lightens age spots; improves skin firmness, elasticity, resiliency; smoothes, tightens, or fills in fine lines on the skin; reduces the appearance of dark circles under the eye; improves lip texture or condition; enhances natural lip color; increases lip volume; promotes epithelialization of post-procedure skin; restores the skin's barrier or moisture balance; improves the appearance of age spots; improves the appearance of skin pigmentation, or a combination thereof. In one embodiment, the compositions reduce the appearance of fine lines and wrinkles; diminish the appearance of age spots and dyspigmentation; improve skin texture, tone and elasticity; reduce roughness and photo damage; strengthen the ability of skin to regenerate itself; prevent or reduce environmental damage; smooth and tightens skin; brighten and lighten age spots; reduce fine and coarse lines and wrinkles; improve appearance of fine and coarse periocular wrinkles; improve appearance of nasolabial folds; improve perioral wrinkles; improve facial fine and coarse lines; improve skin tone, radiance and evenness; improve skin firmness; reduce tactile roughness; improve skin texture, overall photodamage, overall hyperpigmentation; global improvement; reduction in appearance of dark spots and/or patches; improve appearance of skin brightness and youthful appearance; improve overall condition of skin; improve the appearance of photoaged skin; improve appearance of intrinsically and extrinsically aged skin; improve skin cellular turnover; improve skin barrier; improve skin's ability to retain moisture; reduce the appearance of brown and red blotchiness, redness; increase skin epidermal thickness; strengthen dermal epidermal junction; reduce the appearance of pore size and pores; improve smoothness, or a combination thereof.

In certain embodiments, administration of a composition described herein may result in at least a 2-fold improvement of one or more symptoms or conditions. Folds improvement of one or more symptoms or conditions include, but are not limited to, 3-fold, 5-fold, 10-fold, 15-fold, 20-fold, 25-fold, 75-fold, 100-fold or more, or any number therebetween. In certain embodiments, administration of a composition described herein may result in improvement of about 1% to about 100%, about 10% to about 90%, about 20% to about 80%, about 30% to about 70%, about 40% to about 60%, or about 50%. In other embodiments, administration of a composition described herein may result in improvement of one or more symptoms or conditions of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 100%, about 125%, about 150% or more of one or more symptoms or conditions.

In other embodiments, the disclosure also provides a composition comprising metabolized cell extract and an acceptable carrier. In some embodiments, the metabolized cell extract is cell extract metabolized by yeast cells. In some embodiments, the cell extract is derived from animal cells, skin cells or fibroblasts. In other embodiments, the composition is a topical or injectable composition. In some embodiments, the composition is used to treat or prevent a skin condition. In other embodiments, the skin condition is a cosmetic defect, a congenital defect, hair loss or an acquired defect. In further embodiments, the skin condition is fine lines and wrinkles; age spots and dyspigmentation; decreased skin texture, tone and elasticity; roughness and photo damage; decreased ability of skin to regenerate itself; environmental damage; decreased smoothness and tightness of skin; age spots; fine and coarse lines and wrinkles; fine and coarse periocular wrinkles; nasolabial folds; facial fine and coarse lines; decreased skin radiance and evenness; decreased skin firmness; hyperpigmentation; dark spots and/or patches; decreased skin brightness and youthful appearance; photoaged skin; intrinsically and extrinsically aged skin; abnormal skin cellular turnover; decreased skin barrier; decrease of skin's ability to retain moisture; brown and red blotchiness; redness; abnormal skin epidermal thickness; reduction of dermal epidermal junction; increased pore size and number of pores; or a combination thereof.

In one embodiment, the disclosure provides metabolized conditioned growth medium prepared by a process comprising: (a) culturing cells in a growth medium sufficient to meet the nutritional needs required to grow the cells in vitro to form a conditioned growth medium and removing the conditioned growth medium from the cultured cells; (b) culturing yeast cells; (c) exposing the yeast cells to the conditioned growth medium; (d) culturing the yeast cells to metabolize at least a portion of the conditioned growth medium; and (e) collecting the metabolized conditioned growth medium.

In another embodiment, the disclosure provides processes for preparing metabolized conditioned growth medium comprising: (a) culturing cells in a growth medium sufficient to meet the nutritional needs required to grow the cells in vitro to form a conditioned growth medium and removing the conditioned growth medium from the cultured cells; (b) culturing yeast cells; (c) exposing the yeast cells to the conditioned growth medium; (d) culturing the yeast cells to metabolize at least a portion of the conditioned growth medium; and (e) collecting the metabolized conditioned growth medium.

In another embodiment, the disclosure provides compositions comprising metabolized conditioned growth medium, and an acceptable carrier. In another embodiment, the disclosure provides compositions comprising metabolized conditioned growth medium, and an acceptable carrier, wherein the topical composition is used to treat or prevent a skin condition. In some embodiments, the composition is used to treat or prevent a skin condition. In some embodiments, the skin condition is a cosmetic defect, a congenital defect, hair loss or an acquired defect. In further embodiments, the skin condition is fine lines and wrinkles; age spots and dyspigmentation; decreased skin texture, tone and elasticity; roughness and photo damage; decreased ability of skin to regenerate itself; environmental damage; decreased smoothness and tightness of skin; age spots; fine and coarse lines and wrinkles; fine and coarse periocular wrinkles; nasolabial folds; facial fine and coarse lines; decreased skin radiance and evenness; decreased skin firmness; hyperpigmentation; dark spots and/or patches; decreased skin brightness and youthful appearance; photoaged skin; intrinsically and extrinsically aged skin; abnormal skin cellular turnover; decreased skin barrier; decrease of skin's ability to retain moisture; brown and red blotchiness; redness; abnormal skin epidermal thickness; reduction of dermal epidermal junction; increased pore size and number of pores; or a combination thereof.

In another embodiment, the disclosure provides compositions comprising metabolized conditioned growth medium, and an acceptable carrier, wherein the topical composition is used to treat or prevent a skin condition, the metabolized conditioned growth medium is present in an amount of about 0.01% to about 50% by weight of the composition, and the metabolized conditioned growth medium is prepared by culturing yeast cells in a growth medium sufficient to meet the nutritional needs required to grow the cells in vitro to form a conditioned growth medium In another embodiment, the disclosure provides methods for preventing or treating a skin condition in a subject comprising administering to the subject a therapeutically effective amount of metabolized conditioned growth medium. In some embodiments, the composition is used to treat or prevent a skin condition. In other embodiments, the skin condition is a cosmetic defect, a congenital defect, hair loss or an acquired defect. In further embodiments, the skin condition is fine lines and wrinkles; age spots and dyspigmentation; decreased skin texture, tone and elasticity; roughness and photo damage; decreased ability of skin to regenerate itself; environmental damage; decreased smoothness and tightness of skin; age spots; fine and coarse lines and wrinkles; fine and coarse periocular wrinkles; nasolabial folds; facial fine and coarse lines; decreased skin radiance and evenness; decreased skin firmness; hyperpigmentation; dark spots and/or patches; decreased skin brightness and youthful appearance; photoaged skin; intrinsically and extrinsically aged skin; abnormal skin cellular turnover; decreased skin barrier; decrease of skin's ability to retain moisture; brown and red blotchiness; redness; abnormal skin epidermal thickness; reduction of dermal epidermal junction; increased pore size and number of pores; or a combination thereof.

In one embodiment, the disclosure provides methods for treating hair loss comprising administering to a subject a therapeutically effective amount of metabolized conditioned growth medium. In another embodiment, the disclosure provides methods for stimulating hair growth comprising administering to a subject a therapeutically effective amount of metabolized conditioned growth medium. In another embodiment, the disclosure provides methods for preventing or treating a congenital defect in a subject comprising administering to the subject a therapeutically effective amount of metabolized conditioned growth medium. In another embodiment, the disclosure provides methods for preventing or treating a cosmetic defect in a subject comprising administering to the subject a therapeutically effective amount of metabolized conditioned growth medium. In one embodiment, treatment of the cosmetic defect rejuvenates sun damaged and aging skin; improves the appearance of fine lines and wrinkles; promotes cell renewal; diminishes the appearance of age spots and dyspigmentation; improves skin tone, texture and elasticity; reduces roughness and photo damage; prevents or reduces environmental damage; plumps the skin; brightens the skin; lightens the skin; strengthens the ability of skin to regenerate itself; improves the appearance of age spots; brightens and lightens age spots; improves skin firmness, elasticity, resiliency; smoothes, tightens, or fills in fine lines on the skin; reduces the appearance of dark circles under the eye; improves lip texture or condition; enhances natural lip color; increases lip volume; promotes epithelialization of post-procedure skin; restores the skin's barrier or moisture balance; improves the appearance of age spots; improves the appearance of skin pigmentation, or a combination thereof. In another embodiment, the disclosure provides methods for preventing or treating an acquired defect in a subject comprising administering to the subject a therapeutically effective amount of metabolized conditioned growth medium. Said methods may rejuvenate sun damaged and aging skin; improve the appearance of fine lines and wrinkles; promote cell renewal; improve skin tone, texture and/or firmness; plump the skin; brightens the skin; lighten the skin; strengthen the skin's ability to regenerate itself; improve the appearance of age spots; improve skin firmness, elasticity, resiliency; smooth, tighten, or fill in fine lines on the skin; reduce the appearance of dark circles under the eye; improve lip texture or condition; enhance natural lip color; increases lip volume; promote epithelialization of post-procedure skin; restore the skin's barrier or moisture balance; improve the appearance of age spots; improve the appearance of skin pigmentation, reduce the appearance of fine lines and wrinkles; diminish the appearance of age spots and dyspigmentation; improve skin texture, tone and elasticity; reduce roughness and photo damage; strengthen the ability of skin to regenerate itself; prevent or reduce environmental damage; smooth and tightens skin; brighten and lighten age spots, reduce in fine and coarse lines and wrinkles, improve appearance of fine and coarse periocular wrinkles, improve appearance of nasolabial folds, improve perioral wrinkles, improve facial fine and coarse lines, improve skin tone, radiance and evenness, improve skin firmness, reduce tactile roughness, improve skin texture, overall photodamage, overall hyperpigmentation, global improvement, reduce in appearance of dark spots and/or patches, improve appearance of skin brightness and youthful appearance, improve overall condition of skin, improve the appearance of photoaged skin, improve appearance of intrinsically and extrinsically aged skin, improve skin cellular turnover, improve skin barrier, improve skin's ability to retain moisture, reduce the appearance of brown and red blotchiness, redness, increase skin epidermal thickness, strengthen dermal epidermal junction, reduce the appearance of pore size and pores, improve smoothness, or a combination thereof.

In another embodiment, the disclosure provides methods for reducing the appearance of fine lines and wrinkles comprising administering to a subject a therapeutically effective amount of metabolized conditioned growth medium. In another embodiment, the disclosure provides methods for diminishing the appearance of age spots and dyspigmentation comprising administering to a subject a therapeutically effective amount of metabolized conditioned growth medium. In another embodiment, the disclosure provides methods for improving skin texture, tone and elasticity comprising administering to a subject a therapeutically effective amount of metabolized conditioned growth medium. In another embodiment, the disclosure provides methods for reducing roughness and photo damage comprising administering to a subject a therapeutically effective amount of metabolized conditioned growth medium. In another embodiment, the disclosure provides methods for strengthening the ability of skin to regenerate itself comprising administering to a subject a therapeutically effective amount of metabolized conditioned growth medium. In another embodiment, the disclosure provides methods for preventing or reducing environmental damage comprising administering to a subject a therapeutically effective amount of metabolized conditioned growth medium. In another embodiment, the disclosure provides methods for smoothing and tightening skin comprising administering to a subject a therapeutically effective amount of metabolized conditioned growth medium. In another embodiment, the disclosure provides methods for brightening and lightening age spots comprising administering to a subject a therapeutically effective amount of metabolized conditioned growth medium.

In another embodiment, the disclosure provides metabolized cell extract prepared by a process comprising: (a) providing a cell extract; (b) culturing yeast cells; (c) exposing the yeast cells to the cell extract; (d) culturing the yeast cells to metabolize at least a portion of the cell extract; and (e) collecting the metabolized conditioned cell extract.

In another embodiment, the disclosure provides processes for preparing the metabolized cell extract comprising: (a) providing a cell extract; (b) culturing yeast cells; (c) exposing the yeast cells to the cell extract; (d) culturing the yeast cells to metabolize at least a portion of the cell extract; and (e) collecting the metabolized cell extract.

In another embodiment, the disclosure provides compositions comprising metabolized cell extract, and an acceptable carrier. In another embodiment, the disclosure provides compositions comprising metabolized cell extract, and an acceptable carrier, wherein the topical composition is used to treat or prevent a skin condition. In some embodiments, the composition is used to treat or prevent a skin condition. In other embodiments, the skin condition is a cosmetic defect, a congenital defect, hair loss or an acquired defect. In further embodiments, the skin condition is fine lines and wrinkles; age spots and dyspigmentation; decreased skin texture, tone and elasticity; roughness and photo damage; decreased ability of skin to regenerate itself; environmental damage; decreased smoothness and tightness of skin; age spots; fine and coarse lines and wrinkles; fine and coarse periocular wrinkles; nasolabial folds; facial fine and coarse lines; decreased skin radiance and evenness; decreased skin firmness; hyperpigmentation; dark spots and/or patches; decreased skin brightness and youthful appearance; photoaged skin; intrinsically and extrinsically aged skin; abnormal skin cellular turnover; decreased skin barrier; decrease of skin's ability to retain moisture; brown and red blotchiness; redness; abnormal skin epidermal thickness; reduction of dermal epidermal junction; increased pore size and number of pores; or a combination thereof.

In another embodiment, the disclosure provides compositions comprising metabolized cell extract, and an acceptable carrier, wherein the topical composition is used to treat or prevent skin condition, the metabolized cell extract is present in an amount of about 0.01% to about 50% by weight of the composition, and the metabolized cell extract is cell extract metabolized by yeast cells. In other embodiments, the skin condition is a cosmetic defect, a congenital defect, hair loss or an acquired defect. In further embodiments, the skin condition is fine lines and wrinkles; age spots and dyspigmentation; decreased skin texture, tone and elasticity; roughness and photo damage; decreased ability of skin to regenerate itself; environmental damage; decreased smoothness and tightness of skin; age spots; fine and coarse lines and wrinkles; fine and coarse periocular wrinkles; nasolabial folds; facial fine and coarse lines; decreased skin radiance and evenness; decreased skin firmness; hyperpigmentation; dark spots and/or patches; decreased skin brightness and youthful appearance; photoaged skin; intrinsically and extrinsically aged skin; abnormal skin cellular turnover; decreased skin barrier; decrease of skin's ability to retain moisture; brown and red blotchiness; redness; abnormal skin epidermal thickness; reduction of dermal epidermal junction; increased pore size and number of pores; or a combination thereof. In one embodiment, treatment of the cosmetic defect rejuvenates sun damaged and aging skin; improves the appearance of fine lines and wrinkles; promotes cell renewal; diminishes the appearance of age spots and dyspigmentation; improves skin tone, texture and elasticity; reduces roughness and photo damage; prevents or reduces environmental damage; plumps the skin; brightens the skin; lightens the skin; strengthens the ability of skin to regenerate itself; improves the appearance of age spots; brightens and lightens age spots; improves skin firmness, elasticity, resiliency; smoothes, tightens, or fills in fine lines on the skin; reduces the appearance of dark circles under the eye; improves lip texture or condition; enhances natural lip color; increases lip volume; promotes epithelialization of post-procedure skin; restores the skin's barrier or moisture balance; improves the appearance of age spots; improves the appearance of skin pigmentation, or a combination thereof.

In another embodiment, the disclosure provides methods for preventing or treating a skin condition in a subject comprising administering to the subject a therapeutically effective amount of metabolized cell extract. In another embodiment, the disclosure provides methods for treating hair loss comprising administering to a subject a therapeutically effective amount of metabolized cell extract. In another embodiment, the disclosure provides methods for stimulating hair growth comprising administering to a subject a therapeutically effective amount of metabolized cell extract. In another embodiment, the disclosure provides methods for preventing or treating a congenital defect in a subject comprising administering to the subject a therapeutically effective amount of metabolized cell extract. In another embodiment, the disclosure provides methods for preventing or treating a cosmetic defect in a subject comprising administering to the subject a therapeutically effective amount of metabolized cell extract. In one embodiment, treatment of the cosmetic defect rejuvenates sun damaged and aging skin; improves the appearance of fine lines and wrinkles; promotes cell renewal; diminishes the appearance of age spots and dyspigmentation; improves skin tone, texture and elasticity; reduces roughness and photo damage; prevents or reduces environmental damage; plumps the skin; brightens the skin; lightens the skin; strengthens the ability of skin to regenerate itself; improves the appearance of age spots; brightens and lightens age spots; improves skin firmness, elasticity, resiliency; smoothes, tightens, or fills in fine lines on the skin; reduces the appearance of dark circles under the eye; improves lip texture or condition; enhances natural lip color; increases lip volume; promotes epithelialization of post-procedure skin; restores the skin's barrier or moisture balance; improves the appearance of age spots; improves the appearance of skin pigmentation, or a combination thereof. In another embodiment, the disclosure provides methods for preventing or treating a acquired defect in a subject comprising administering to the subject a therapeutically effective amount of metabolized cell extract. Said methods may rejuvenate sun damaged and aging skin; improve the appearance of fine lines and wrinkles; promote cell renewal; improve skin tone, texture and/or firmness; plump the skin; brightens the skin; lighten the skin; strengthen the skin's ability to regenerate itself; improve the appearance of age spots; improve skin firmness, elasticity, resiliency; smooth, tighten, or fill in fine lines on the skin; reduce the appearance of dark circles under the eye; improve lip texture or condition; enhance natural lip color; increases lip volume; promote epithelialization of post-procedure skin; restore the skin's barrier or moisture balance; improve the appearance of age spots; improve the appearance of skin pigmentation, reduce the appearance of fine lines and wrinkles; diminish the appearance of age spots and dyspigmentation; improve skin texture, tone and elasticity; reduce roughness and photo damage; strengthen the ability of skin to regenerate itself; prevent or reduce environmental damage; smooth and tightens skin; brighten and lighten age spots, reduce in fine and coarse lines and wrinkles, improve appearance of fine and coarse periocular wrinkles, improve appearance of nasolabial folds, improve perioral wrinkles, improve facial fine and coarse lines, improve skin tone, radiance and evenness, improve skin firmness, reduce tactile roughness, improve skin texture, overall photodamage, overall hyperpigmentation, global improvement, reduce in appearance of dark spots and/or patches, improve appearance of skin brightness and youthful appearance, improve overall condition of skin, improve the appearance of photoaged skin, improve appearance of intrinsically and extrinsically aged skin, improve skin cellular turnover, improve skin barrier, improve skin's ability to retain moisture, reduce the appearance of brown and red blotchiness, redness, increase skin epidermal thickness, strengthen dermal epidermal junction, reduce the appearance of pore size and pores, improve smoothness, or a combination thereof.

In another embodiment, the disclosure provides methods for reducing the appearance of fine lines and wrinkles comprising administering to a subject a therapeutically effective amount of metabolized cell extract. In another embodiment, the disclosure provides methods for diminishing the appearance of age spots and dyspigmentation comprising administering to a subject a therapeutically effective amount of metabolized cell extract. In another embodiment, the disclosure provides methods for improving skin texture, tone and elasticity comprising administering to a subject a therapeutically effective amount of metabolized cell extract. In another embodiment, the disclosure provides methods for reducing roughness and photo damage comprising administering to a subject a therapeutically effective amount of metabolized cell extract. In another embodiment, the disclosure provides methods for strengthening the ability of skin to regenerate itself comprising administering to a subject a therapeutically effective amount of metabolized cell extract. In another embodiment, the disclosure provides methods for preventing or reducing environmental damage comprising administering to a subject a therapeutically effective amount of metabolized cell extract. In another embodiment, the disclosure provides methods for smoothing and tightening skin comprising administering to a subject a therapeutically effective amount of metabolized cell extract. In another embodiment, the disclosure provides methods for brightening and lightening age spots comprising administering to a subject a therapeutically effective amount of metabolized cell extract.

In one embodiment, also provided are compositions comprising a metabolized conditioned growth medium and an acceptable carrier, wherein the metabolized conditioned growth medium is conditioned growth medium metabolized by yeast cells. In one embodiment, the conditioned growth medium is prepared by culturing cells in a growth medium sufficient to meet the nutritional needs required to grow the cells in vitro to form a conditioned growth medium. In another embodiment, the composition is an injectable composition or a topical composition. In yet another embodiment, the topical composition is an ointment, a cream, a hydrogel, or a lotion. In still another embodiment, the metabolized condition growth medium is encapsulated within an encapsulant. In one embodiment, the encapsulant is at least one of liposomes, niosomes, sub-micron emulsions, polymeric encapsulates, gels, creams and lotions. In some embodiments, the composition is used to treat or prevent a skin condition. In other embodiments, the composition is used to treat or prevent fine lines and wrinkles; age spots and dyspigmentation; decreased skin texture, tone and elasticity; roughness and photo damage; decreased ability of skin to regenerate itself; environmental damage; decreased smoothness and tightness of skin; age spots; fine and coarse lines and wrinkles; fine and coarse periocular wrinkles; nasolabial folds; facial fine and coarse lines; decreased skin radiance and evenness; decreased skin firmness; hyperpigmentation; dark spots and/or patches; decreased skin brightness and youthful appearance; photoaged skin; intrinsically and extrinsically aged skin; abnormal skin cellular turnover; decreased skin barrier; decrease of skin's ability to retain moisture; brown and red blotchiness; redness; abnormal skin epidermal thickness; reduction of dermal epidermal junction; increased pore size and number of pores; or a combination thereof. In still other embodiments, the composition is used to treat or prevent a cosmetic defect, a congenital defect, hair loss or an acquired defect. In some embodiments, the cosmetic defect is a glabellar frown line, deep nasolabial crease, circum-oral geographical wrinkle, sunken cheeks or mammary hypoplasia. In other embodiments, treatment of the cosmetic defect rejuvenates sun damaged and aging skin; improves the appearance of fine lines and wrinkles; promotes cell renewal; diminishes the appearance of age spots and dyspigmentation; improves skin tone, texture and elasticity; reduces roughness and photo damage; prevents or reduces environmental damage; plumps the skin; brightens the skin; lightens the skin; strengthens the ability of skin to regenerate itself improves the appearance of age spots; brightens and lightens age spots; improves skin firmness, elasticity, resiliency; smoothes, tightens, or fills in fine lines on the skin; reduces the appearance of dark circles under the eye; improves lip texture or condition; enhances natural lip color; increases lip volume; promotes epithelialization of post-procedure skin; restores the skin's barrier or moisture balance; improves the appearance of age spots; improves the appearance of skin pigmentation, or a combination thereof. In some embodiments, the acquired defect is a medical condition that occurs post-trauma, post-surgery or post-infection. In other embodiments, the acquired defect is a post-medical procedure defect. In yet other embodiments, the acquired defect is a depressed scar, subcutaneous atrophy, a keratotic lesion, enophthalmos in an unucleated eye, acne pitting of the face, linear scleroderma with subcutaneous atrophy, saddle-nose deformity, Romberg's disease or unilateral vocal cord paralysis.

Also provided are compositions comprising a metabolized cell extract and an acceptable carrier, wherein the metabolized cell extract is cell extract metabolized by yeast cells. In some embodiments, the cell extract is derived from animal cells. In other embodiments, the cell extract is derived from skin cells. In another embodiment, the cell extract is derived from fibroblasts. In some embodiments, the composition is an injectable composition or a topical composition. In some embodiments, the topical composition is an ointment, a cream, a hydrogel, or a lotion. In other embodiments, the metabolized condition growth medium is encapsulated within an encapsulant. In one embodiment, the encapsulant is at least one of liposomes, niosomes, submicron emulsions, polymeric encapsulates, gels, creams and lotions. In some embodiments, the composition is used to treat or prevent a skin condition. In other embodiments, the skin condition is a cosmetic defect, a congenital defect, hair loss or an acquired defect. In further embodiments, the skin condition is fine lines and wrinkles; age spots and dyspigmentation; decreased skin texture, tone and elasticity; roughness and photo damage; decreased ability of skin to regenerate itself; environmental damage; decreased smoothness and tightness of skin; age spots; fine and coarse lines and wrinkles; fine and coarse periocular wrinkles; nasolabial folds; facial fine and coarse lines; decreased skin radiance and evenness; decreased skin firmness; hyperpigmentation; dark spots and/or patches; decreased skin brightness and youthful appearance; photoaged skin; intrinsically and extrinsically aged skin; abnormal skin cellular turnover; decreased skin barrier; decrease of skin's ability to retain moisture; brown and red blotchiness; redness; abnormal skin epidermal thickness; reduction of dermal epidermal junction; increased pore size and number of pores; or a combination thereof.

In yet other embodiments, the composition is used to treat or prevent a cosmetic defect, a congenital defect, hair loss or an acquired defect. In some embodiments, the cosmetic defect is a glabellar frown line, deep nasolabial crease, circum-oral geographical wrinkle, sunken cheeks or mammary hypoplasia. In some embodiments, treatment of the cosmetic defect rejuvenates sun damaged and aging skin; improves the appearance of fine lines and wrinkles; promotes cell renewal; diminishes the appearance of age spots and dyspigmentation; improves skin tone, texture and elasticity; reduces roughness and photo damage; prevents or reduces environmental damage; plumps the skin; brightens the skin; lightens the skin; strengthens the ability of skin to regenerate itself; improves the appearance of age spots; brightens and lightens age spots; improves skin firmness, elasticity, resiliency; smoothes, tightens, or fills in fine lines on the skin; reduces the appearance of dark circles under the eye; improves lip texture or condition; enhances natural lip color; increases lip volume; promotes epithelialization of post-procedure skin; restores the skin's barrier or moisture balance; improves the appearance of age spots; improves the appearance of skin pigmentation, or a combination thereof. In some embodiments, the acquired defect is a medical condition that occurs post-trauma, post-surgery or post-infection. In other embodiments, the acquired defect is a post-medical procedure defect. In yet other embodiments, the acquired defect is a depressed scar, subcutaneous atrophy, a keratotic lesion, enophthalmos in an unucleated eye, acne pitting of the face, linear scleroderma with subcutaneous atrophy, saddle-nose deformity, Romberg's disease or unilateral vocal cord paralysis. In still other embodiments, the composition is used to treat or prevent fine lines and wrinkles; age spots and dyspigmentation; decreased skin texture, tone and elasticity; roughness and photo damage; decreased ability of skin to regenerate itself; environmental damage; decreased smoothness and tightness of skin; age spots; fine and coarse lines and wrinkles; fine and coarse periocular wrinkles; nasolabial folds; facial fine and coarse lines; decreased skin radiance and evenness; decreased skin firmness; hyperpigmentation; dark spots and/or patches; decreased skin brightness and youthful appearance; photoaged skin; intrinsically and extrinsically aged skin; abnormal skin cellular turnover; decreased skin barrier; decrease of skin's ability to retain moisture; brown and red blotchiness; redness; abnormal skin epidermal thickness; reduction of dermal epidermal junction; increased pore size and number of pores; or a combination thereof.

Also provided herein is a metabolized conditioned growth medium prepared by a process comprising:

(a) culturing cells in a growth medium sufficient to meet the nutritional needs required to grow the cells in vitro to form a conditioned growth medium and removing the conditioned growth medium from the cultured cells;

(b) culturing yeast cells;

(c) exposing the yeast cells to the conditioned growth medium;

(d) culturing the yeast cells to metabolize at least a portion of the conditioned growth medium; and (e) collecting the metabolized conditioned growth medium. In some embodiments, the yeast used in the process above is of the *Pichia* genus. In other embodiments, the yeast is *Pichia pastoris*. In other embodiments, the cells in step (a) are skin cells. In yet other embodiments, the cells in step (a) are fibroblasts. In still other embodiments, the cells in step (a) are animal cells. In still other embodiments, the process to prepare the metabolized conditioned growth medium further comprises (e) processing the metabolized conditioned growth medium, wherein processing is concentrating, filtering, purifying, or a combination thereof. In some embodiments, the metabolized conditioned growth medium includes a continuous flow system or a bioreactor system in the culturing step of (a) or (b). In yet other embodiments, the cells are suspended or floated in the growth medium.

Provided herein is a process for preparing the metabolized conditioned growth medium above, comprising:

(a) culturing cells in a growth medium sufficient to meet the nutritional needs required to grow the cells in vitro to form a conditioned growth medium and removing the conditioned growth medium from the cultured cells;

(b) culturing yeast cells;

(c) exposing the yeast cells to the conditioned growth medium;

(d) culturing the yeast cells to metabolize at least a portion of the conditioned growth medium; and (e) collecting the metabolized conditioned growth medium. In one embodiment, a composition is provided comprising the metabolized conditioned growth medium and an acceptable carrier. In some embodiments, the metabolized conditioned growth medium is present in an amount of about 0.0001% to about 95% by weight of the composition. In other embodiments, the metabolized conditioned growth medium is present in an amount of about 0.01% to about 50% by weight of the composition. In some embodiments, the metabolized conditioned growth medium is present in an amount of about 0.01% to about 10% by weight of the composition. In some embodiments, the metabolized conditioned growth medium is present in an amount of about 10% to about 20% by weight of the composition. In some embodiments, the metabolized conditioned growth medium is present in an amount of about 0.01%, 0.5%, 1.0%, 5.0%, 10%, 15%, 20%, 25%, 30%, 35%, 40%, 45%, 50%, 55%, 60%, 65%, 70%, 75%, 80%, 85%, 90% or 95% by weight of the composition. In one non-limiting example, the metabolized conditioned growth medium is present in the composition in an amount of about 10%, about 15%, or about 20% by weight of the composition. In other embodiments, the composition further comprises at least one of water, surfactants, emulsifiers, conditioners, emollients, waxes, oils, polymers, thickeners, fixatives, colorants, nutraceuticals, cosmeceuticals, therapeutics, pharmaceuticals, antifungals, antimicrobials, steroidal hormones, antidandruff agents, anti-acne components, sunscreens, and preservatives. In some embodiments, the composition is an injectable composition or a topical composition. In one embodiment, the topical composition is an ointment, a cream, a hydrogel, or a lotion. In other embodiments, the metabolized conditioned growth medium is encapsulated within an encapsulant. In some embodiments, the encapsulant is at least one of liposomes, niosomes, sub-micron emulsions, polymeric encapsulates, gels, creams, and lotions.

Also provided herein is a metabolized cell extract prepared by a process comprising:

(a) providing a cell extract;

(b) culturing yeast cells;

(c) exposing the yeast cells to the cell extract;

(d) culturing the yeast cells to metabolize at least a portion of the cell extract; and (e) collecting the metabolized cell extract. In some embodiments, the yeast is of the *Pichia* genus. In other embodiments, the yeast is *Pichia pastoris*. In yet other embodiments, the cell extract is derived from skin cells. In still other embodiments, the cell extract is derived from fibroblasts. In still other embodiments, the cell extract is derived from animal cells. In yet other embodiments, the process further comprises (e) processing the metabolized cell extract, wherein processing is concentrating, filtering, purifying, or a combination thereof. In one embodiment, the culturing comprises a continuous flow system or a bioreactor system.

In still other embodiments, a process for preparing the metabolized cell extract above comprises:

(a) providing a cell extract;

(b) culturing yeast cells;

(c) exposing the yeast cells to the cell extract;

(d) culturing the yeast cells to metabolize at least a portion of the cell extract; and (e) collecting the metabolized cell extract.

Also provided herein are compositions comprising: an acceptable carrier and a metabolized conditioned growth medium prepared by a process comprising:

(a) culturing cells in a growth medium sufficient to meet the nutritional needs required to grow the cells in vitro to form a conditioned growth medium and removing the conditioned growth medium from the cultured cells;

(b) culturing yeast cells;

(c) exposing the yeast cells to the conditioned growth medium;

(d) culturing the yeast cells to metabolize at least a portion of the conditioned growth medium; and (e) collecting the metabolized conditioned growth medium. In some embodiments, the yeast is of the *Pichia* genus. In other embodiments, the yeast is *Pichia pastoris*. In some embodiments, the cells in step (a) are skin cells. In other embodiments, the cells in step (a) are fibroblasts. In yet another embodiment, the cells in step (a) are animal cells. In some embodiments, the process further comprises (e) processing the metabolized conditioned growth medium, wherein processing is concentrating, filtering, purifying, or a combination thereof. In some embodiments, the culturing of step (a) or (b) comprises a continuous flow system or a bioreactor system. In yet other embodiments, the cells are suspended or floated in the growth medium. In still other embodiments, the metabolized conditioned growth medium is present in an amount of about 0.0001% to about 95% by weight of the composition. In still other embodiments, the metabolized conditioned growth medium is present in an amount of about 0.01% to about 50% by weight of the composition. In yet other embodiments, the metabolized conditioned growth medium is present in an amount of about 0.01% to about 10% by weight of the composition. In some embodiments, the metabolized conditioned growth medium is present in an amount of about 0.01%, 0.5%, 1.0%, 5.0%, 10%, 15%, 20%, 25%, 30%, 35%, 40%, 45%, 50%, 55%, 60%, 65%, 70%, 75%, 80%, 85%, 90% or 95% by weight of the composition. In one non-limiting example, the metabolized conditioned growth medium is present in the composition in an amount of about 10%, about 15%, or about 20% by weight of the composition. In still other embodiments, the composition further comprises at least one of water, surfactants, emulsifiers, conditioners, emollients, waxes, oils, polymers, thickeners, fixatives, colorants, nutraceuticals, cosmeceuticals, therapeutics, pharmaceuticals, antifungals, antimicrobials, steroidal hormones, antidandruff agents, anti-acne components, sunscreens, and preservatives. In still other embodiments, the composition is an injectable composition or a topical composition. In yet other embodiments, the topical composition is an ointment, a cream, a hydrogel, or a lotion. In some embodiments, the metabolized conditioned growth medium is encapsulated within an encapsulant. In one embodiment, the encapsulant is at least one of liposomes, niosomes, sub-micron emulsions, polymeric encapsulates, gels, creams, and lotions.

Also provided herein are compositions comprising: an acceptable carrier and a metabolized cell extract prepared by a process comprising:
(a) providing a cell extract;
(b) culturing yeast cells;
(c) exposing the yeast cells to the cell extract;
(d) culturing the yeast cells to metabolize at least a portion of the cell extract; and
(e) collecting the metabolized cell extract. In some embodiments, the yeast is of the *Pichia* genus. In other embodiments, the yeast is *Pichia pastoris*. In other embodiments, the cell extract is derived from skin cells. In yet other embodiments, the cell extract is derived from fibroblasts. In still other embodiments, the cell extract is derived from animal cells. In one embodiment, the process further comprises (e) processing the metabolized cell extract, wherein processing is concentrating, filtering, purifying, or a combination thereof. In another embodiment, the culturing comprises a continuous flow system or a bioreactor system. In still other embodiments, the metabolized conditioned growth medium is present in an amount of about 0.0001% to about 95% by weight of the composition. In yet another embodiment, the metabolized cell extract is present in an amount of about 0.01% to about 50% by weight of the composition. In still other embodiments, the metabolized cell extract is present in an amount of about 0.01% to about 10% by weight of the composition. In some embodiments, the metabolized cell extract is present in an amount of about 10% to about 20% by weight of the composition. In some embodiments, the metabolized cell extract is present in an amount of about 0.01%, 0.5%, 1.0%, 5.0%, 10%, 15%, 20%, 25%, 30%, 35%, 40%, 45%, 50%, 55%, 60%, 65%, 70%, 75%, 80%, 85%, 90% or 95% by weight of the composition. In one non-limiting example, the metabolized cell extract is present in the composition in an amount of about 10%, about 15%, or about 20% by weight of the composition. In one embodiment, the composition further comprises at least one of water, surfactants, emulsifiers, conditioners, emollients, waxes, oils, polymers, thickeners, fixatives, colorants, nutraceuticals, cosmeceuticals, therapeutics, pharmaceuticals, antifungals, antimicrobials, steroidal hormones, antidandruff agents, anti-acne components, sunscreens, and preservatives. In still other embodiments, the composition is an injectable composition or a topical composition. In yet another embodiment, the topical composition is an ointment, a cream, a hydrogel, or a lotion. In one embodiment, the metabolized conditioned growth medium is encapsulated within an encapsulant. In another embodiment, the encapsulant is at least one of liposomes, niosomes, sub-micron emulsions, polymeric encapsulates, gels, creams, and lotions.

Also provided herein are methods for preventing or treating a skin condition in a subject comprising administering to the subject a therapeutically effective amount of a composition comprising: an acceptable carrier and a metabolized conditioned growth medium prepared by a process comprising:
(a) culturing cells in a growth medium sufficient to meet the nutritional needs required to grow the cells in vitro to form a conditioned growth medium and removing the conditioned growth medium from the cultured cells;
(b) culturing yeast cells;
(c) exposing the yeast cells to the conditioned growth medium;
(d) culturing the yeast cells to metabolize at least a portion of the conditioned growth medium; and
(e) collecting the metabolized conditioned growth medium. In one embodiment, the skin condition is a cosmetic defect. In another embodiment, the condition is hair loss. In another embodiment, the condition is a congenital defect or an acquired defect. In one embodiment, the acquired defect is a medical condition that occurs post-trauma, post-surgery or post-infection. In another embodiment, the acquired defect is a post-medical procedure defect. In yet another embodiment, the acquired defect is a depressed scar, subcutaneous atrophy, a keratotic lesion, enophthalmos in an unucleated eye, acne pitting of the face, linear scleroderma with subcutaneous atrophy, saddle-nose deformity, Romberg's disease or unilateral vocal cord paralysis. In one embodiment, the cosmetic defect is a glabellar frown line, deep nasolabial crease, circum-oral geographical wrinkle, sunken cheeks or mammary hypoplasia. In certain embodiments, the condition is fine lines and wrinkles; age spots and dyspigmentation; decreased skin texture, tone and elasticity; roughness and photo damage; decreased ability of skin to regenerate itself; environmental damage; decreased smoothness and tightness of skin; age spots; fine and coarse lines and wrinkles; fine and coarse periocular wrinkles; nasolabial folds; facial fine and coarse lines; decreased skin radiance and evenness; decreased skin firmness; hyperpigmentation; dark spots and/or patches; decreased skin brightness and youthful appearance; photoaged skin; intrinsically and extrinsically aged skin; abnormal skin cellular turnover; decreased skin barrier; decrease of skin's ability to retain moisture; brown and red blotchiness; redness; abnormal skin epidermal thickness; reduction of dermal epidermal junction; increased pore size and number of pores; or a combination thereof. In certain embodiments, administration of a composition described herein may result in at least a 2-fold improvement of one or more symptoms or conditions. Folds improvement of one or more symptoms or conditions include, but are not limited to, 3-fold, 5-fold, 10-fold, 15-fold, 20-fold, 25-fold, 75-fold, 100-fold or more, or any number therebetween. In certain embodiments, administration of a composition described herein may result in improvement of about 1% to about 100%, about 10% to about 90%, about 20% to about 80%, about 30% to about 70%, about 40% to about 60%, or about 50%. In other embodiments, administration of a composition described herein may result in improvement of one or more symptoms or conditions of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 100%, about 125%, about 150% or more of one or more symptoms or conditions. In some embodiments, the yeast is of the *Pichia* genus. In some embodiments, the yeast is *Pichia pastoris*. In one embodiment, the cells in step (a) are skin cells. In another embodiment, the cells in step (a) are fibroblasts. In some embodiments, the cells in step (a) are animal cells. In other embodiments, the process further comprises (e) processing the metabolized conditioned growth medium, wherein processing is concentrating, filtering, purifying, or a combination thereof. In one embodiment, the culturing of step (a) or (b) comprises a continuous flow system or a bioreactor system. In another embodiment, the cells are suspended or floated in the growth medium. In still other embodiments, the metabolized conditioned growth medium is present in the composition in an amount of about 0.0001% to about 95% by weight of the composition. In another embodiment, the metabolized conditioned growth medium is present in the composition in an amount of about 0.01% to about 50% by weight of the composition. In one embodiment, the metabolized conditioned growth medium is present in the composition in an amount of about 0.01% to about 10% by weight of the composition. In some embodiments, the metabolized conditioned growth medium is present in an amount of about 10% to about 20% by weight of the composition. In some embodiments, the metabolized conditioned growth medium is present in an amount of about 0.01%, 0.5%, 1.0%, 5.0%, 10%, 15%, 20%, 25%, 30%, 35%, 40%, 45%, 50%, 55%, 60%, 65%, 70%, 75%, 80%, 85%, 90% or 95% by weight of the composition. In one non-limiting example, the metabolized conditioned growth medium is present in the composition in an amount of about 10%, about 15%, or about 20% by weight of the composition. In some embodiments, the composition further comprises at least one of water, surfactants, emulsifiers, conditioners, emollients, waxes, oils, polymers, thickeners, fixatives, colorants, nutraceuticals, cosmeceuticals, therapeutics, pharmaceuticals, antifungals, antimicrobials, steroidal hormones, antidandruff agents, anti-acne components, sunscreens, and preservatives. In one embodiment, the composition is an injectable composition or a topical composition. In another embodiment, the topical composition is an ointment, a cream, a hydrogel, or a lotion. In one embodiment, the metabolized conditioned growth medium is encapsulated within an encapsulant. In some embodiments, the encapsulant is at least one of liposomes, niosomes, submicron emulsions, polymeric encapsulates, gels, creams, and lotions. In some embodiments, at least one extracellular matrix protein is up-regulated by the administration of the composition to the subject. In some embodiments, the extracellular matrix protein is up-regulated by about 5% to about 100%. In one embodiment, the extracellular matrix protein is up-regulated by about 10% to about 50%. In another embodiment, the extracellular matrix protein is up-regulated by about 60% to about 100%. In yet another embodiment, the extracellular matrix protein is up-regulated by about 5%, by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95% or by about 100%. In one embodiment, the extracellular matrix protein is a collagen protein or a lysyl hydroxylase protein. In some embodiments, the extracellular matrix protein is encoded by COL4A1 gene or PLOD1 gene. In other embodiments, at least one repair protein is up-regulated by the administration of the composition to the subject. In one embodiment, the repair protein is up-regulated by about 10% to about 70%. In another embodiment, the repair protein is up-regulated by about 25% to about 50%. In some embodiments, the repair-protein is up-regulated by about 5%, by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95% or by about 100%. In one embodiment, the repair protein is a fibronectin protein. In yet another embodiment, the repair protein is encoded by FN1 gene. In some embodiments, at least one cellular connectivity protein is up-regulated by the administration of the composition to the subject. In one embodiment, the cellular connectivity protein is up-regulated by about 5% to about 200%. In one embodiment, the cellular connectivity protein is up-regulated by about 10% to about 80%. In some embodiments, the cellular connectivity protein is up-regulated by about 30% to about 50%. In one embodiment, the cellular connectivity protein is up-regulated by about 5%, by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95%, by about 100%, by about 110%, by about 120%, by about 130%, by about 140%, by about 150%, by about 160%, by about 170%, by about 180%, by about 190% or by about 200%. In other embodiments, the cellular connectivity protein is involucrin protein. In some embodiments, the cellular connectivity protein is encoded by IVL gene. In one embodiment, at least one antioxidant protein is up-regulated by the administration of the composition to the subject. In yet another embodiment, the antioxidant protein is up-regulated by about 5% to about 300%. In some embodiments, the antioxidant protein is up-regulated by about 10% to about 50%. In other embodiments, the antioxidant protein is up-regulated by about 200% to about 250%. In some embodiments, the antioxidant protein is up-regulated by about 5%, by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95%, by about 100%, by about 125%, by about 150%, by about 175%, by about 200%, by about 250% or by about 300%. In one embodiment, the antioxidant protein is a superoxide dismutase protein. In another embodiment, the antioxidant protein is encoded by SOD2 gene.

Also provided herein are methods for preventing or treating a skin condition in a subject comprising administering to the subject a therapeutically effective amount of a composition comprising: an acceptable carrier and a metabolized cell extract prepared by a process comprising:
  (a) providing a cell extract;
  (b) culturing yeast cells;
  (c) exposing the yeast cells to the cell extract;
  (d) culturing the yeast cells to metabolize at least a portion of the cell extract; and
  (e) collecting the metabolized cell extract.

In one embodiment, the condition is a cosmetic defect. In another embodiment, the condition is hair loss. In another embodiment, the condition is a congenital defect or an acquired defect. In one embodiment, the acquired defect is a medical condition that occurs post-trauma, post-surgery or post-infection. In another embodiment, the acquired defect is a post-medical procedure defect. In yet another embodiment, the acquired defect is a depressed scar, subcutaneous atrophy, a keratotic lesion, enophthalmos in an unucleated eye, acne pitting of the face, linear scleroderma with subcutaneous atrophy, saddle-nose deformity, Romberg's disease or unilateral vocal cord paralysis. In one embodiment, the cosmetic defect is a glabellar frown line, deep nasolabial crease, circum-oral geographical wrinkle, sunken cheeks or mammary hypoplasia. In certain embodiments, the skin condition is a cosmetic defect, a congenital defect, hair loss or an acquired medical defect. In further embodiments, the skin condition is fine lines and wrinkles; age spots and dyspigmentation; decreased skin texture, tone and elasticity; roughness and photo damage; decreased ability of skin to regenerate itself; environmental damage; decreased smoothness and tightness of skin; age spots; fine and coarse lines and wrinkles; fine and coarse periocular wrinkles; nasolabial folds; facial fine and coarse lines; decreased skin radiance and evenness; decreased skin firmness; hyperpigmentation; dark spots and/or patches; decreased skin brightness and youthful appearance; photoaged skin; intrinsically and extrinsically aged skin; abnormal skin cellular turnover; decreased skin barrier; decrease of skin's ability to retain moisture; brown and red blotchiness; redness; abnormal skin epidermal thickness; reduction of dermal epidermal junction; increased pore size and number of pores; or a combination thereof. In certain embodiments, administration of a composition described herein may result in at least a 2-fold improvement of one or more symptoms or conditions. Folds improvement of one or more symptoms or conditions include, but are not limited to, 3-fold, 5-fold, 10-fold, 15-fold, 20-fold, 25-fold, 75-fold, 100-fold or more, or any number therebetween. In certain embodiments, administration of a composition described herein may result in improvement of about 1% to about 100%, about 10% to about 90%, about 20% to about 80%, about 30% to about 70%, about 40% to about 60%, or about 50%. In other embodiments, administration of a composition described herein may result in improvement of one or more symptoms or conditions of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 100%, about 125%, about 150% or more of one or more symptoms or conditions. In some embodiments, the yeast is of the *Pichia* genus. In some embodiments, the yeast is *Pichia pastoris*. In one embodiment, the cells in step (a) are derived from skin cells. In another embodiment, the cells in step (a) are derived from fibroblasts. In some embodiments, the cells in step (a) are derived from animal cells. In other embodiments, the process further comprises (e) processing the metabolized cell extract, wherein processing is concentrating, filtering, purifying, or a combination thereof. In one embodiment, the culturing of step (a) or (b) comprises a continuous flow system or a bioreactor system. In another embodiment, the cells are suspended or floated in the growth medium. In still other embodiments, the metabolized cell extract is present in the composition in an amount of about 0.0001% to about 95% by weight of the composition. In another embodiment, the metabolized cell extract is present in the composition in an amount of about 0.01% to about 50% by weight of the composition. In one embodiment, the metabolized cell extract is present in the composition in an amount of about 0.01% to about 10% by weight of the composition. In some embodiments, the metabolized cell extract is present in an amount of about 10% to about 20% by weight of the composition. In some embodiments, the metabolized cell extract is present in an amount of about 0.01%, 0.5%, 1.0%, 5.0%, 10%, 15%, 20%, 25%, 30%, 35%, 40%, 45%, 50%, 55%, 60%, 65%, 70%, 75%, 80%, 85%, 90% or 95% by weight of the composition. In one non-limiting example, the metabolized cell extract is present in the composition in an amount of about 10%, about 15%, or about 20% by weight of the composition. In some embodiments, the composition further comprises at least one of water, surfactants, emulsifiers, conditioners, emollients, waxes, oils, polymers, thickeners, fixatives, colorants, nutraceuticals, cosmeceuticals, therapeutics, pharmaceuticals, antifungals, antimicrobials, steroidal hormones, antidandruff agents, anti-acne components, sunscreens, and preservatives. In one embodiment, the composition is an injectable composition or a topical composition. In another embodiment, the topical composition is an ointment, a cream, a hydrogel, or a lotion. In one embodiment, the metabolized cell extract is encapsulated within an encapsulant. In some embodiments, the encapsulant is at least one of liposomes, niosomes, sub-micron emulsions, polymeric encapsulates, gels, creams, and lotions. In some embodiments, at least one extracellular matrix protein is up-regulated by the administration of the composition to the subject. In some embodiments, the extracellular matrix protein is up-regulated by about 5% to about 100%. In one embodiment, the extracellular matrix protein is up-regulated by about 10% to about 50%. In another embodiment, the extracellular matrix protein is up-regulated by about 60% to about 100%. In yet another embodiment, the extracellular matrix protein is up-regulated by about 5%, by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95% or by about 100%. In one embodiment, the extracellular matrix protein is a collagen protein or a lysyl hydroxylase protein. In some embodiments, the extracellular matrix protein is encoded by COL4A1 gene or PLOD1 gene. In other embodiments, at least one repair protein is up-regulated by the administration of the composition to the subject. In one embodiment, the repair protein is up-regulated by about 10% to about 70%. In another embodiment, the repair protein is up-regulated by about 25% to about 50%. In some embodiments, the repair-protein is up-regulated by about 5%, by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95% or by about 100%. In one embodiment, the repair protein is a fibronectin protein. In yet another embodiment, the repair protein is encoded by FN1 gene. In some embodiments, at least one cellular connectivity protein is up-regulated by the administration of the composition to the subject. In one embodiment, the cellular connectivity protein is up-regulated by about 5% to about 200%. In one embodiment, the cellular connectivity protein is up-regulated by about 10% to about 80%. In some embodiments, the cellular connectivity protein is up-regulated by about 30% to about 50%. In one embodiment, the cellular connectivity protein is up-regulated by about 5%, by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95%, by about 100%, by about 110%, by about 120%, by about 130%, by about 140%, by about 150%, by about 160%, by about 170%, by about 180%, by about 190% or by about 200%. In other embodiments, the cellular connectivity protein is involucrin protein. In some embodiments, the cellular connectivity protein is encoded by IVL gene. In one embodiment, at least one antioxidant protein is up-regulated by the administration of the composition to the subject. In yet another embodiment, the antioxidant protein is up-regulated by about 5% to about 300%. In some embodiments, the antioxidant protein is up-regulated by about 10% to about 50%. In other embodiments, the antioxidant protein is up-regulated by about 200% to about 250%. In some embodiments, the antioxidant protein is up-regulated by about 5%, by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95%, by about 100%, by about 125%, by about 150%, by about 175%, by about 200%, by about 250% or by about 300%. In one embodiment, the antioxidant protein is a superoxide dismutase protein. In another embodiment, the antioxidant protein is encoded by SOD2 gene.

DETAILED DESCRIPTION OF THE INVENTION

Figure 1:
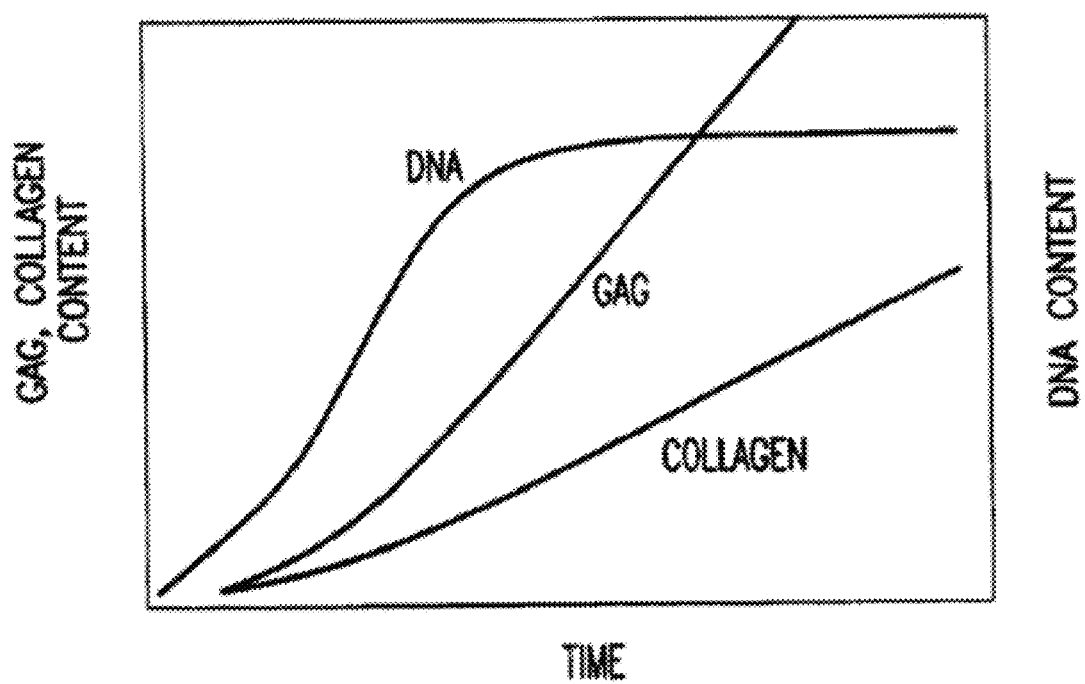
FIG. 1 is a graph representing the kinetics of the deposition of glycosaminoglycans and collagen laid down over time by the three-dimensional tissue products Transcyte™ and Dermagraft®. The deposition volumes of the glycosaminoglycans are dependent on the period of growth while the deposition of collagen is not dependent on the period of growth.

The present disclosure relates to novel compositions comprising metabolized conditioned growth medium and/or metabolized cell extract, cultured using any eukaryotic cell type or three-dimensional tissue construct, and methods for using the compositions. The cells are cultured in monolayer or in three-dimensions. The cells are preferably human and include stromal cells, parenchymal cells, mesenchymal stem cells, liver reserve cells, neural stem cells, pancreatic stem cells and/or embryonic stem cells. Medium conditioned by cell and tissue cultures will contain a variety of naturally secreted proteins, such as biologically active growth factors. Also disclosed are novel compositions comprising products derived from the conditioned cell media and uses for these compositions.

The "pre-conditioned" cell culture medium may be any cell culture medium which adequately addresses the nutritional needs of the cells being cultured. Examples of cell media include, but are not limited to Dulbecco's Modified Eagle's Medium (DMEM), Ham's F12, RPMI 1640, Iscove's, McCoy's and other media formulations readily apparent to those skilled in the art, including those found in *Methods For Preparation of Media, Supplements and Substrate For Serum-Free Animal Cell Culture* Alan R. Liss, New York (1984) and *Cell & Tissue Culture: Laboratory Procedures*, John Wiley & Sons Ltd., Chichester, England 1996, both of which are incorporated by reference herein in their entirety. The medium may be supplemented, with any components necessary to support the desired cell or tissue culture. Additionally serum, such as bovine serum, which is a complex solution of albumins, globulins, growth promoters and growth inhibitors may be added if desired. The serum should be pathogen free and carefully screened for mycoplasma bacterial, fungal, and viral contamination. Also, the serum should generally be obtained from the United States and not obtained from countries where indigenous livestock carry transmittable agents. Hormone addition into the medium may or may not be desired. The medium may also be serum-free, i.e., cells are grown in the absence of a serum supplement.

The "conditioned growth medium" may be any growth medium conditioned as disclosed herein, and can be prepared, for example, as disclosed in U.S. Pat. Nos. 6,372,494; 7,118,746; 7,160,726, all of which are incorporated herein by reference in its entirety.

Other ingredients, such as vitamins, growth and attachment factors, proteins etc., can be selected by those of skill in the art in accordance with his or her particular need. In some embodiments, any cell type appropriate to achieve the desired conditioned medium may be used. Genetically engineered cells may be used to culture the media. Such cells can be modified, for example, to express a desired protein or proteins so that the concentration of the expressed protein or proteins in the medium is optimized for the particular desired application. In accordance with the present disclosure, the cells and tissue cultures used to condition the medium may be engineered to express a target gene product which may impart a wide variety of functions, including but not limited to, improved properties in expressing proteins resembling physiological reactions, increased expression of a particular protein useful for a specific application, such as wound healing or inhibiting certain proteins such as proteases, lactic acid, etc.

The cells may be engineered to express a target gene product which is biologically active which provides a chosen biological function, which acts as a reporter of a chosen physiological condition, which augments deficient or defective expression of a gene product, or which provides an anti-viral, anti-bacterial, anti-microbial, or anti-cancer activity. In accordance with the present disclosure, the target gene product may be a peptide or protein, such as an enzyme, hormone, cytokine, antigen, or antibody, a regulatory protein, such as a transcription factor or DNA binding protein, a structural protein, such as a cell surface protein, or the target gene product may be a nucleic acid such as a ribosome or antisense molecule. The target gene products include, but are not limited to, gene products which enhance cell growth. For example, the genetic modification may upregulate an endogenous protein, introduce a new protein or regulate ion concentration by expressing a heterologous ion channel or altering endogenous ion channel function. Examples include, but are not limited to engineered tissues that express gene products which are delivered systemically (e.g., secreted gene products such as proteins including growth factors, hormones, Factor VIII, Factor IX, neurotransmitters, and enkaphalins).

In some embodiments, cells are grown in a two-dimensional monolayer according to any method known to the skilled artisan. See, e.g., cell culture techniques such as those described in Sambrook J et al. (2000) Molecular Cloning: A Laboratory Manual (Third Edition); Goeddel, ed. (1990) Methods in Enzymology 185, Current Protocols In Molecular Biology; F. M. Ausubel et al., eds., Current Protocols, a joint venture between Greene Publishing Associates, Inc. and John Wiley & Sons, Inc. (1994, supplemented through 1999); Animal Cell Culture: A Practical Approach (Freshney ed. 1986).

In some embodiments, cells are grown on a three-dimensional stromal support and grow in multiple layers, forming a cellular matrix. This matrix system approaches physiologic conditions found in vivo to a greater degree than previously described monolayer tissue culture systems. Three-dimensional cultures, such as Dermagraft® (Advanced Tissue Sciences, Inc., La Jolla, Calif.)"Dermagraft®", and TransCyte™ (Smith & Nephew, PLC, United Kingdom) "Transcyte™", produce numerous growth factors and other proteins that are secreted into the medium at physiological ratios and concentrations. Dermagraft® is composed of allogeneic neonatal fibroblasts cultured on biodegradable polyglactin. TransCyte™ is a temporary living skin replacement comprising a three-dimensional stromal tissue bonded to a transitional covering as described in U.S. Pat. No. 5,460,939. Additionally, the three-dimensional tissue cultures which condition the cell media may contain mesenchymal stem cells, liver reserve cells, neural stem cells, pancreatic stem cells, and/or embryonic stem cells and/or parenchymal cells and/or parenchymal stem cells found in many tissue types, including but not limited to bone marrow, skin, liver, pancreas, kidney, adrenal and neurologic tissue, as well as tissues of the gastrointestinal and genitourinary tracts, and the circulatory system. See U.S. Pat. Nos. 4,721,096; 4,963,489; 5,032,508; 5,266,480; 5,160,490; and 5,559,022, each of which is incorporated by reference herein in their entirety.

I. Definitions

The following terms used herein shall have the meanings indicated:

Cells: includes cells from any organism, including animals, plants, fungi, protists, or monera. In one embodiment, the source of the cells is an animal or a plant. In another embodiment, the animal is a mammal. In another embodiment, the mammal is a human.

Cell Extract: includes lysed or fragmented cell content that may or may not include cell particulate matter.

Adherent Layer: cells attached directly to the three-dimensional support or connected indirectly by attachment to cells that are themselves attached directly to the support.

Conditioned Medium: a formulation containing extracellular protein(s) and cellular metabolites, which has previously supported the growth of any desired eukaryotic cell type, said cells having been cultured in either two or three dimensions. Also called "Conditioned Cell Medium" or "Conditioned Cell and Tissue Culture Medium".

Stromal Cells: fibroblasts with or without other cells and/or elements found in loose connective tissue, including but not limited to, endothelial cells, pericytes, macrophages, monocytes, plasma cells, mast cells, adipocytes, mesenchymal stem cells, liver reserve cells, neural stem cells, pancreatic stem cells, chondrocytes, prechondrocytes, etc.

Tissue-Specific or Parenchymal Cells: the cells which form the essential and distinctive tissue of an organ as distinguished from its supportive framework.

Two-Dimensional Cell Culture: cells cultured in a monolayer, for example, on a flat surface or the like.

Three-Dimensional Framework: a three-dimensional scaffold composed of any material and/or shape that (a) allows cells to attach to it (or can be modified to allow cells to attach to it); and (b) allows cells to grow in more than one layer. This support is inoculated with stromal cells to form the living three-dimensional stromal tissue. The structure of the framework can include a mesh, a sponge or can be formed from a hydrogel.

Three-Dimensional Stromal Tissue or Living Stromal Matrix: a three-dimensional framework which has been inoculated with stromal cells that are grown on the support. The extracellular matrix proteins elaborated by the stromal cells are deposited onto the framework, thus forming a living stromal tissue. The living stromal tissue can support the growth of tissue-specific cells later inoculated to form the three-dimensional cell culture.

Tissue-Specific Three-Dimensional Cell Culture or Tissue-Specific Three-Dimensional Construct: a three-dimensional living stromal tissue which has been inoculated with tissue-specific cells and cultured. In general, the tissue specific cells used to inoculate the three-dimensional stromal matrix should include the "stem" cells (or "reserve" cells) for that tissue; i.e., those cells which generate new cells that will mature into the specialized cells that form the parenchyma of the tissue.

The following abbreviations shall have the meanings indicated:

BCS=bovine calf serum
BFU-E=burst-forming unit-erythroid
TGF-β=transforming growth factor-β
CFU-C=colony forming unit-culture
CFU-GEMM=colony forming unit-granuloid, erythroid, monocyte, megakaryocyte
CSF=colony-stimulating factor
DMEM=Dulbecco's Modified Eagle's Medium
EDTA=ethylene diamine tetraacetic acid
FBS=fetal bovine serum
FGF=fibroblast growth factor
GAG=glycosaminoglycan
GM-C SF=granulocyte/macrophage colony-stimulating factor
HBSS=Hank's balanced salt solution
HS=horse serum
IGF=insulin-like growth factor
LTBMC=long term bone marrow culture
MEM=minimal essential medium
PBL=peripheral blood leukocytes
PBS=phosphate buffered saline
PDGF=platelet-derived growth factor RPMI 1640=Roswell Park Memorial Institute medium number 1640 (GIBCO, Inc., Grand Island, N.Y.)

SEM=scanning electron microscopy

VEGF=vascular endothelial growth factor

II. Metabolized Conditioned Growth Medium and Metabolized Cell Extract

In one embodiment, the disclosure provides metabolized conditioned growth medium prepared by a process comprising: (a) culturing cells in a growth medium sufficient to meet the nutritional needs required to grow the cells in vitro to form a conditioned growth medium and removing the conditioned growth medium from the cultured cells; (b) culturing yeast cells; (c) exposing the yeast cells to the conditioned growth medium; (d) culturing the yeast cells to metabolize at least a portion of the conditioned growth medium; and (e) collecting the metabolized conditioned growth medium. In some embodiments, the cells may originate from a plant and/or animal source, including human.

In another embodiment, the disclosure provides metabolized cell extract prepared by a process comprising: (a) providing a cell extract; (b) culturing yeast cells; (c) exposing the yeast cells to the cell extract; (d) culturing the yeast cells to metabolize at least a portion of the cell extract; and (e) collecting the metabolized cell extract. In some embodiments, the cell extract is obtained by: culturing cells in a growth medium sufficient to meet the nutritional needs required to grow the cells in vitro and removing the resulting cell extract from the growth medium. In some embodiments, the cells may originate from a plant and/or animal source, including human.

Metabolizing the extracellular proteins in conditioned growth media or cell extracts, such as growth factors, cytokines, and stress proteins, opens new possibilities in the preparation of products for use in a large variety of areas including tissue repair, e.g., in the treatment of wounds and other tissue defects such as cosmetic defects as well as human and animal feed supplements. For example, growth factors are known to play an important role in the wound healing process. At least one activity of these growth factors is imparted to the conditioned cell media or cell extracts through the metabolism processes of the disclosure.

Cellular cytokines and growth factors are involved in a number of critical cellular processes including cell proliferation, adhesion, morphologic appearance, differentiation, migration, inflammatory responses, angiogenesis, and cell death. Studies have demonstrated that hypoxic stress and injury to cells induce responses including increased levels of mRNA and proteins corresponding to growth factors such as PDGF (platelet-derived growth factor), VEGF (vascular endothelial growth factor), FGF (fibroblast growth factor), and IGF (insulin-like growth factor) (Gonzalez-Rubio, M. et al., 1996, *Kidney Int.* 50(1):164-73; Abramovitch, R. et al., 1997, *Int J. Exp. Pathol.* 78(2):57-70; Stein, I. et al., 1995, *Mol Cell Biol.* 15(10):5363-8; Yang, W. et al., 1997, FEBS Lett. 403(2):139-42; West, N. R. et al., 1995, *J. Neurosci. Res.* 40(5):647-59).

Growth factors, such as transforming growth factor-β, also known as TGF-β, are induced by certain stress proteins during wound healing. Two known stress proteins are GRP78 and HSP90. These proteins stabilize cellular structures and render the cells resistant to adverse conditions. The TGF-β family of dimeric proteins includes TGF-β1, TGF-β2, and TGF-β3 and regulates the growth and differentiation of many cell types. Furthermore, this family of proteins exhibits a range of biological effects, stimulating the growth of some cell types (Noda et al., 1989, *Endocrinology* 124: 2991-2995) and inhibiting the growth of other cell types (Goey et al., 1989, *J. Immunol.* 143:877-880; Pietenpol et al., 1990, *Proc. Natl. Acad. Sci. USA* 87:3758-3762). TGF-β has also been shown to increase the expression of extracellular matrix proteins including collagen and fibronectin (Ignotz et al., 1986, *J. Biol. Chem.* 261:4337-4345) and to accelerate the healing of wounds (Mustoe et al., 1987, Science 237:1333-1335).

Another such growth factor is PDGF. PDGF was originally found to be a potent mitogen for mesenchymal-derived cells (Ross R. et al., 1974, *Proc. Natl. Acad. Sci. USA* 71(4):1207-1210; Kohler N. et al., 1974, *Exp. Cell Res.* 87:297-301). Further studies have shown that PDGF increases the rate of cellularity and granulation in tissue formation. Wounds treated with PDGF have the appearance of an early stage inflammatory response including an increase in neutrophils and macrophage cell types at the wound site. These wounds also show enhanced fibroblast function (Pierce, G. F. et al., 1988, *J. Exp. Med.* 167:974-987). Both PDGF and TGF-β have been shown to increase collagen formation, DNA content, and protein levels in animal studies (Grotendorst, G. R. et al., 1985, *J. Clin. Invest.* 76:2323-2329; Sporn, M. B. et al., 1983, *Science* (Wash D.C.) 219:1329). PDGF has been shown to be effective in the treatment of human wounds. In human wounds, PDGF-AA expression is increased within pressure ulcers undergoing healing. The increase of PDGF-AA corresponds to an increase in activated fibroblasts, extracellular matrix deposition, and active vascularization of the wound. Furthermore, such an increase in PDGF-AA is not seen in chronic non-healing wounds (Principles of Tissue Engineering, R. Lanza et al. (eds.), pp. 133-141 (R.G. Landes Co. TX 1997). A number of other growth factors having the ability to induce angiogenesis and wound healing include VEGF, KGF and basic FGF.

A. Growth Media

Growth media formulations for cell culture are well known in the literature and many are commercially available.

Preconditioned media ingredients include, but are not limited to those described below. Additionally, the concentration of the ingredients is well known to one of ordinary skill in the art. See, for example, *Methods For Preparation Of Media, Supplements and Substrate for Serum-free Animal Cell Cultures*, supra. The ingredients include amino-acids (both D and/or L-amino acids) such as glutamine, alanine, arginine, asparagine, cysteine, glutamic acid, glycine, histidine, isoleucine, leucine, lysine, methionine, phenylalanine, proline, serine, threonine, tryptophan, tyrosine, and valine and their derivatives; acid soluble subgroups such as thiamine, ascorbic acid, ferric compounds, ferrous compounds, purines, glutathione and monobasic sodium phosphates.

Additional ingredients include sugars, deoxyribose, ribose, nucleosides, water soluble vitamins, riboflavin, salts, trace metals, lipids, acetate salts, phosphate salts, HEPES, phenol red, pyruvate salts and buffers.

Other ingredients often used in media formulations include fat soluble vitamins (including A, D, E and K) steroids and their derivatives, cholesterol, fatty acids and lipids Tween 80, 2-mercaptoethanol pyramidines as well as a variety of supplements including serum (fetal, horse, calf, etc.), proteins (insulin, transferrin, growth factors, hormones, etc.) antibiotics (gentamicin, penicillin, streptomycin, amphotericin B, etc.) whole egg ultra filtrate, and attachment factors (fibronectins, vitronectins, collagens, laminins, tenascins, etc.).

The media may or may not need to be supplemented with growth factors and other proteins such as attachment factors since many of the cell constructs, particularly the three-dimensional cell and tissue culture constructs described in this application themselves elaborate such growth and attachment factors and other products into the media.

B. Cell Cultures

1. The Cells

Any cells may be used in the cell cultures. For example, the cells may be stromal cells, parenchymal cells, mesenchymal stem cells (lineage committed or uncommitted progenitor cells), liver reserve cells, neural stem cells, pancreatic stem cells, and/or embryonic stem cells. The cells may include, but are not limited to, bone marrow, skin, liver, pancreas, kidney, neurological tissue, adrenal gland, mucosal epithelium, and smooth muscle, to name but a few. The fibroblasts and fibroblast-like cells and other cells and/or elements that comprise the stroma may be fetal or adult in origin, and may be derived from convenient sources such as skin, liver, pancreas, mucosa, arteries, veins, umbilical cord, and placental tissues, etc. Such tissues and/or organs can be obtained by appropriate biopsy or upon autopsy. In fact, cadaver organs may be used to provide a generous supply of stromal cells and elements.

Embryonic stem cells and/or other elements that comprise the stroma may be isolated using methods known in the art. For instance, recently human embryonic stem cell populations and methods for isolating and using these cells have been reported in Keller et al., *Nature Med.*, 5:151-152 (1999), *Smith Curr. Biol.* 8:R802-804 (1998); isolated from primordial germ cells, Shamblatt et al., *PNAS* 95:13726-1373 (1998), isolated from blastocytes, Thomason et al., *Science* 282:1145-1147 (1988). The isolation and culture of mesenchymal stem cells are known in the art. See Mackay et al., *Tissue Eng.* 4:415-428 (1988); William et al., *Am Surg.* 65:22-26 (1999). Inoculation of these cells is described infra, in Section 5.3. Likewise, neural stem cells may be isolated in the manner described in Flax et al., *Nature Biotechnol.*, 16:1033-1039 (1998); and Frisen et al., *Cell. Mol. Life. Sci.*, 54:935-945 (1998).

The cells may be cultured in any manner known in the art including in monolayer, beads or in three-dimensions and by any means (i.e., culture dish, roller bottle, a continuous flow system, etc.). Methods of cell and tissue culturing are well known in the art, and are described, for example, in *Cell & Tissue Culture: Laboratory Procedures*, supra, Freshney (1987), *Culture of Animal Cells: A Manual of Basic Techniques*, infra.

In general, the cell lines utilized are carefully screened for human and animal pathogens. Depending upon the application, such screening may be of critical importance where only pathogen free cells are acceptable (e.g., for wound healing, food additives, etc.) Methods of screening for pathogens are well known in the art. The cell type, whether cultured in two-dimensions or three-dimensions, will affect the properties of the conditioned medium. In some embodiments, the cells are cultured in two dimensions. In other embodiments, the cells are cultured in three dimensions.

a. Genetically Engineered Cells

In some embodiments, the cells can act as vehicles for introducing gene products into the media or extract that promote the repair and/or regeneration of tissue defects, for example. The cells can be genetically engineered to express, for example, inflammatory mediators, such as IL-6, IL-8 and G-CSF. The cells could also or alternatively be genetically engineering to express anti-inflammatory factors, e.g., anti-GM-CSF, anti-TNF, anti-IL-1, anti-IL-2, etc.

In another embodiment, the cells can be genetically engineered to express a gene into the media or extract which would exert a therapeutic effect, e.g., in the production of TGF-$\beta$3 to stimulate cartilage production, or other factors such as BMP-13 to promote chondrogenesis or stimulatory factors that promote migration of stromal cells and/or matrix deposition. Since the constructs comprise eukaryotic cells, the gene product will be properly expressed and processed to form an active product. Preferably, the expression control elements used should allow for the regulated expression of the gene so that the product can be over-synthesized in culture. The transcriptional promoter chosen, generally, and promoter elements specifically, depend, in part, upon the type of tissue and cells cultured. Cells and tissues which are capable of secreting proteins are preferable (e.g., those having abundant rough endoplasmic reticulum and Golgi complex organelles). The over-produced gene product will then be secreted by the engineered cell into the conditioned media.

The cells may be genetically engineered to regulate one or more genes; or the regulation of gene expression may be transient or long-term; or the gene activity may be non-inducible or inducible.

The cells can also be genetically engineered to "knock out" expression of factors that promote inflammation. Negative modulatory techniques for the reduction of target gene expression levels or target gene product activity levels are discussed below. "Negative modulation", as used herein, refers to a reduction in the level and/or activity of target gene product relative to the level and/or activity of the target gene product in the absence of the modulatory treatment. The expression of a gene native to the cell can be reduced or knocked out using a number of techniques, for example, expression may be inhibited by inactivating the gene completely (commonly termed "knockout") using standard homologous recombination techniques. Usually, an exon encoding an important region of the protein (or an exon 5' to that region) is interrupted by a positive selectable marker (for example neo), preventing the production of normal mRNA from the target gene and resulting in inactivation of the gene. A gene may also be inactivated by creating a deletion or an inactivating insertion in part of a gene, or by deleting the entire gene. By using a construct with two regions of homology to the target gene that are far apart in the genome, the sequences intervening the two regions can be deleted. Mombaerts et al., 1991, *Proc. Nat. Acad. Sci. U.S.A.* 88:3084-3087. Alternatively, a gene may also be inactivated by deletion of upstream or downstream expression elements.

Antisense and ribozyme molecules which inhibit expression of the target gene can also be used to reduce the level of target gene activity. For example, antisense RNA molecules which inhibit the expression of major histocompatibility gene complexes (HLA) have been shown to be most versatile with respect to immune responses. Furthermore, appropriate ribozyme molecules can be designed as described, e.g., by Haseloff et al., 1988, Nature 334:585-591; Zaug et al., 1984, *Science* 224:574-578; and Zaug and Cech, 1986, *Science* 231:470-475. Still further, triple helix molecules can be utilized in reducing the level of target gene activity. These techniques are described in detail by L. G. Davis et al., eds, *Basic Methods in Molecular Biology*, 2nd ed., Appleton & Lange, Norwalk, Conn. 1994.

Methods that may be useful to genetically engineer the cells are well-known in the art and are further detailed in co-owned U.S. Pat. Nos. 4,963,489 and 5,785,964, the disclosures of which are incorporated herein by reference.

For example, a recombinant DNA construct or vector containing an exogenous nucleic acid, e.g., encoding a gene product of interest, may be constructed and used to transform or transfect the stromal cells. Such transformed or transfected cells that carry the exogenous nucleic acid, and that are capable of expressing said nucleic acid, are selected and clonally expanded in the three-dimensional constructs of this disclosure.

Methods for preparing DNA constructs containing the gene of interest, for transforming or transfecting cells, and for selecting cells carrying and expressing the gene of interest are well-known in the art. See, for example, the techniques described in Maniatis et al., 1989, *Molecular Cloning, A Laboratory Manual*, Cold Spring Harbor Laboratory Press, Cold Spring Harbor, N.Y.; Ausubel et al., 1989, *Current Protocols in Molecular Biology*, Greene Publishing Associates & Wiley Interscience, N.Y.; and Sambrook et al., 1989, *Molecular Cloning: A Laboratory Manual*, 2nd Ed., Cold Spring Harbor Laboratory Press, Cold Spring Harbor, N.Y.

The cells can be engineered using any of a variety of vectors including, but not limited to, integrating viral vectors, e.g., retrovirus vector or adeno-associated viral vectors; or non-integrating replicating vectors, e.g., papilloma virus vectors, SV40 vectors, adenoviral vectors; or replication-defective viral vectors. Where transient expression is desired, non-integrating vectors and replication defective vectors may be preferred, since either inducible or constitutive promoters can be used in these systems to control expression of the gene of interest. Alternatively, integrating vectors can be used to obtain transient expression, provided the gene of interest is controlled by an inducible promoter. Other methods of introducing DNA into cells include the use of liposomes, lipofection, electroporation, a particle gun, or by direct DNA injection.

The cells are preferably transformed or transfected with a nucleic acid, e.g., DNA, controlled by, i.e., in operative association with, one or more appropriate expression control elements such as promoter or enhancer sequences, transcription terminators, polyadenylation sites, among others, and a selectable marker. Following the introduction of the foreign DNA, engineered cells may be allowed to grow in enriched media and then switched to selective media. The selectable marker in the foreign DNA confers resistance to the selection and allows cells to stably integrate the foreign DNA as, for example, on a plasmid, into their chromosomes and grow to form foci which, in turn, can be cloned and expanded into cell lines. This method can be advantageously used to engineer cell lines which express the gene product into the media.

Any promoter may be used to drive the expression of the inserted gene. For example, viral promoters include but are not limited to the CMV promoter/enhancer, SV40, papillomavirus, Epstein-Barr virus, elastin gene promoter and β-globin. Preferably, the control elements used to control expression of the gene of interest should allow for the regulated expression of the gene so that the product is synthesized only when needed in vivo. If transient expression is desired, constitutive promoters are preferably used in a non-integrating and/or replication-defective vector. Alternatively, inducible promoters could be used to drive the expression of the inserted gene when necessary. Inducible promoters can be built into integrating and/or replicating vectors. For example, inducible promoters include, but are not limited to, metallothionien and heat shock protein.

According to one embodiment, the inducible promoters used for expressing exogenous genes of interest are those that are the native promoters of those regulatory proteins as disclosed herein that are induced as a result of cyropreservation and subsequent thawing. For example, the promoter of TGF-β, VEGF, or various known heat shock proteins can be used as the expression control element, i.e., can be operatively linked to an exogenous gene of interest in order to express a desired gene product in the tissue constructs conditioning the cell media.

A variety of methods may be used to obtain the constitutive or transient expression of gene products engineered into the cells. For example, the transkaryotic implantation technique described by Seldon et al., 1987, *Science* 236: 714-718 can be used. "Transkaryotic", as used herein, suggests that the nuclei of the implanted cells have been altered by the addition of DNA sequences by stable or transient transfection. Preferably, the cells are engineered to express such gene products transiently and/or under inducible control during the post-operative recovery period, or as a chimeric fusion protein anchored to the stromal cells, for example, as a chimeric molecule composed of an intracellular and/or transmembrane domain of a receptor or receptor-like molecule, fused to the gene product as the extracellular domain.

Furthermore, it may be desirable to prepare a construct having an extracellular matrix containing a foreign gene product, growth factor, regulatory factor, etc., which is then found in the conditioned media. This embodiment is based on the discovery that, during the growth of human stromal cells on a three-dimensional support framework, the cells synthesize and deposit on the framework a human extracellular matrix as produced in normal human tissue. The extracellular matrix is secreted locally by cells and not only binds cells and tissue together but also influences the development and behavior of the cells it contacts. The extracellular matrix contains various connective tissue proteins, e.g., fiber-forming proteins interwoven in a hydrated gel composed of a network of glycosaminoglycans chains. The glycosaminoglycans are a heterogeneous group of long, negatively charged polysaccharide chains, which (except for hyaluronic acid) are covalently linked to protein to form proteoglycans molecules. According to this embodiment, the stromal cells may be genetically engineered to express a desired gene product, or altered forms of a gene product, which will be present in the extracellular matrix and ultimately the cell medium.

2. Culturing the Cells

In some embodiments, the cells are grown in two-dimensional cell cultures. In other embodiments, the cells are grown in three-dimensional cell cultures. See, e.g., U.S. Pat. No. 6,372,494, herein incorporated by reference in its entirety. The stromal cells used in the cell cultures preferably comprise fibroblasts, mesenchymal stem cells, liver reserve cells, neural stem cells, pancreatic stem cells, and/or embryonic stem cells with or without additional cells and/or elements described more fully herein.

The cells can be cultured by any means known in the art. Preferably, the cells are cultured in an environment which enables aseptic processing and handling. Conventional means of cell and tissue culture have been limited by the need for human supervision and control of the media. This limits the amount of cells and tissue that can be cultured at a single time and consequently the volume of conditioned cell media that can be obtained at a single time. For this reason, it is preferred that the media be conditioned in a manner allowing for large scale growth (yielding large scale conditioned media) using, for example, an apparatus for aseptic large scale culturing like that described in co-owned U.S. Pat. No. 5,763,267 (the '267 patent) which is incorporated by reference herein in its entirety for all purposes. Using the aseptic closed system described in the '267 patent, preconditioned culture media is transported from a fluid reservoir to an inlet manifold and evenly distributed to the cultures in a continuous flow system and is useful in culturing three-dimensional cell and tissue cultures, such as Dermagraft® for example. In particular, the apparatus described in the '267 patent includes a plurality of flexible or semi-flexible treatment chambers comprising one or more individual culture pockets, a plurality of rigid spacers, an inlet fluid manifold, an outlet fluid manifold, a fluid reservoir, and a means for transporting fluid within the system.

During treatment, liquid medium is transported from the fluid reservoir to the inlet manifold, which in turn evenly distributes the media to each of the connected treatment chambers and internal culture pockets. An outlet fluid manifold is also provided to ensure that each treatment chamber is evenly filled and to ensure that any air bubbles formed during treatment are removed from the treatment chambers. The treatment chambers are flexible or semi-flexible so as to provide for easy end-user handling during rinsing and application of the cultured transplants. Due to the flexibility of the treatment chambers, rigid spacers are also provided which ensure even fluid distribution within the chambers during treatment.

In another embodiment, the tissue is cultivated in an apparatus for aseptic growth of tissue cultures as described in U.S. Pat. No. 5,843,766 (the '766 patent) incorporated herein in its entirety for all purposes. The '766 patent discloses a tissue culture chamber in which the chamber is a casing that provides for growth of tissue that can be grown, preserved in frozen form, and shipped to the end user in the same aseptic container. The tissue culture chamber includes a casing comprising a substrate within the casing designed to facilitate three-dimensional tissue growth on the surface of the substrate. The casing includes an inlet and an outlet port which assist the inflow and outflow of medium. The casing also includes at least one flow distributor. In one embodiment, the flow distributor is a baffle, which is used to distribute the flow of the medium within the chamber to create a continuous, uniform piece of tissue. In a second embodiment, the flow distributor is a combination of deflector plates, distribution channels, and a flow channel. In each embodiment, the casing further includes a seal so as to ensure an aseptic environment inside the chamber during tissue growth and storage.

Fibroblasts will support the growth of many different cells and tissues in the three-dimensional culture system, and, therefore, can be inoculated onto the matrix to form a "generic" stromal support matrix for culturing any of a variety of cells and tissues. However, in certain instances, it may be preferable to use a "specific" rather than "generic" stromal support matrix, in which case stromal cells and elements can be obtained from a particular tissue, organ, or individual. Moreover, fibroblasts and other stromal cells and/or elements may be derived from the same type of tissue to be cultured in the three-dimensional system. This might be advantageous when culturing tissues in which specialized stromal cells may play particular structural/functional roles; e.g., smooth muscle cells of arteries, glial cells of neurological tissue, Kupffer cells of liver, etc.

Once inoculated onto the three-dimensional support, the stromal cells will proliferate on the framework and deposit the connective tissue proteins naturally secreted by the stromal cells such as growth factors, regulatory factors and extracellular matrix proteins. The stromal cells and their naturally secreted connective tissue proteins substantially envelop the framework thus forming the living stromal tissue which will support the growth of tissue-specific cells inoculated into the three-dimensional culture system of the disclosure. In fact, when inoculated with the tissue-specific cells, the three-dimensional stromal tissue will sustain active proliferation of the culture for long periods of time. Importantly, because openings in the mesh permit the exit of stromal cells in culture, confluent stromal cultures do not exhibit contact inhibition, and the stromal cells continue to grow, divide, and remain functionally active.

Growth and regulatory factors are elaborated by the stromal tissue into the media. Growth factors (for example, but not limited to, αFGF, βFGF, insulin growth factor or TGF-betas), or natural or modified blood products or other bioactive biological molecules (for example, but not limited to, hyaluronic acid or hormones), enhance the colonization of the three-dimensional framework or scaffolding and condition the culture media.

The extent to which the stromal cells are grown prior to use of the cultures in vivo may vary depending on the type of tissue to be grown in three-dimensional tissue culture. The living stromal tissues which condition the medium may be used as corrective structures by implanting them in vivo. Alternatively, the living stromal tissues may be inoculated with another cell type and implanted in vivo. The stromal cells may be genetically engineered to adjust the level of protein products secreted into the culture medium to improve the concentration of recovered product obtained from the conditioned medium. For example, stromal cells may be genetically engineered to improve concentration of one or more or the following products obtained from the conditioned medium. anti-inflammatory factors, e.g., anti-GM-CSF, anti-TNF, anti-IL-1, anti-IL-2, etc. Alternatively, the stromal cells may be genetically engineered to "knock out" expression of native gene products that promote inflammation, e.g., GM-CSF, TNF, IL-1, IL-2, or "knock out" expression of MHC in order to lower the risk of rejection.

Growth of the stromal cells in three-dimensions will sustain active proliferation of both the stromal and tissue-specific cells in culture for much longer time periods than will monolayer systems. Moreover, the three-dimensional system supports the maturation, differentiation, and segregation of cells in culture in vitro to form components of adult tissues analogous to counterparts found in vivo and secure proteins into the conditional medium more closely resembling physiological ratios.

a. Establishment of Three-Dimensional Stromal Tissue

The three-dimensional support or framework may be of any material and/or shape that: (a) allows cells to attach to it (or can be modified to allow cells to attach to it); and (b) allows cells to grow in more than one layer. A number of different materials may be used to form the framework, including but not limited to: non-biodegradable materials, e.g., nylon (polyamides), dacron (polyesters), polystyrene, polypropylene, polyacrylates, polyvinyl compounds (e.g., polyvinylchloride), polycarbonate (PVC), polytetrafluoroethylene (PTFE; teflon), thermanox (TPX), nitrocellulose, cotton; and biodegradable materials, e.g., polyglycolic acid (PGA), collagen, collagen sponges, cat gut sutures, cellulose, gelatin, dextran, polyalkanoates, etc. Any of these materials may be woven braided, knitted, etc., into a mesh, for example, to form the three-dimensional framework. The framework, in turn can be fashioned into any shape desired as the corrective structure, e.g., tubes, ropes, filaments, etc. Certain materials, such as nylon, polystyrene, etc., are poor substrates for cellular attachment. When these materials are used as the three-dimensional framework, it is advisable to pre-treat the framework prior to inoculation of stromal cells in order to enhance the attachment of stromal cells to the support. For example, prior to inoculation with stromal cells, nylon frameworks could be treated with 0.1M acetic acid, and incubated in polylysine, FBS, and/or collagen to coat the nylon. Polystyrene could be similarly treated using sulfuric acid.

When the cultures are to be implanted in vivo, it may be preferable to use biodegradable matrices such as polyglycolic acid, collagen, collagen sponges, woven collagen, catgut suture material, gelatin, polylactic acid, or polyglycolic acid and copolymers thereof, for example. Where the cultures are to be maintained for long periods of time or cryopreserved, non-degradable materials such as nylon, dacron, polystyrene, polyacrylates, polyvinyls, teflons, cotton, etc., may be preferred. A convenient nylon mesh which could be used in accordance with the disclosure is NITEX®, a nylon filtration mesh having an average pore size of 210 µm and an average nylon fiber diameter of 90 µm (#3-210/36, Tetko, Inc., N.Y.).

Stromal cells comprising fibroblasts, mesenchymal stem cells, liver reserve cells, neural stem cells, pancreatic stem cells and/or embryonic stem cells with or without other cells and elements described below, are inoculated onto the framework. Also, cells found in loose connective tissue may be inoculated onto the three-dimensional support along with fibroblasts. Such cells include but are not limited to smooth muscle cells, endothelial cells, pericytes, macrophages, monocytes, plasma cells, mast cells, adipocytes, etc. As previously explained, fetal fibroblasts can be used to form a "generic" three-dimensional stromal matrix that will support the growth of a variety of different cells and/or tissues. However, a "specific" stromal tissue may be prepared by inoculating the three-dimensional framework with fibroblasts derived from the same type of tissue to be cultured and/or from a particular individual who is later to receive the cells and/or tissues grown in culture in accordance with the three-dimensional system.

Thus, in one embodiment, stromal cells which are specialized for the particular tissue may be cultured. For example, stromal cells of hematopoietic tissue, including but not limited to fibroblasts, endothelial cells, macrophages/monocytes, adipocytes and reticular cells, could be used to form the three-dimensional subconfluent stroma for the long term culture of bone marrow in vitro. Hematopoietic stromal cells may be readily obtained from the "buffy coat" formed in bone marrow suspensions by centrifugation at low forces, e.g., 3000×g. In the stromal layer that makes up the inner wall of arteries, a high proportion of undifferentiated smooth muscle cells can be added to provide the protein elastic. Stromal cells of liver may include fibroblasts, Kupffer cells, and vascular and bile duct endothelial cells. Similarly, glial cells could be used as the stroma to support the proliferation of neurological cells and tissues; glial cells for this purpose can be obtained by trypsinization or collagenase digestion of embryonic or adult brain (Ponten and Westermark, 1980, in Federof, S. Hertz, L., eds, "Advances in Cellular Neurobiology," Vol. 1, New York, Academic Press, pp. 209-227). The growth of cells in the three-dimensional stromal cell culture may be further enhanced by adding to the framework, or coating the support with proteins (e.g., collagens, elastic fibers, reticular fibers) glycoproteins, glycosaminoglycans (e.g., heparin sulfate, chondroitin-4-sulfate, chondroitin-6-sulfate, dermatan sulfate, keratin sulfate, etc.), a cellular matrix, and/or other materials.

Further, mesenchymal stem cells (lineage committed or uncommitted progenitor cells) are advantageous "stromal" cells for inoculation onto the framework. The cells may differentiate into osteocytes, fibroblasts of the tendons and ligaments, marrow stromal cells, adipocytes and other cells of connective tissue, chondrocytes, depending on endogens or supplemented growth and regulatory factors and other factors including prostaglandin, interleukins and naturally-occurring chalones which regulate proliferation and/or differentiation.

Fibroblasts may be readily isolated by disaggregating an appropriate organ or tissue which is to serve as the source of the fibroblasts. This may be readily accomplished using techniques known to those skilled in the art. For example, the tissue or organ can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes either alone or in combination. These include but are not limited to trypsin, chymotrypsin, collagenase, elastase, and/or hyaluronidase, DNase, pronase, dispase etc. Mechanical disruption can also be accomplished by a number of methods including, but not limited to, the use of grinders, blenders, sieves, homogenizers, pressure cells, or insonators to name but a few. For a review of tissue disaggregation techniques, see Freshney, *Culture of Animal Cells: A Manual of Basic Technique,* 2d Ed., A. R. Liss, Inc., New York, 1987, Ch. 9, pp. 107-126.

Once the tissue has been reduced to a suspension of individual cells, the suspension can be fractionated into subpopulations from which the fibroblasts and/or other stromal cells and/or elements can be obtained. This also may be accomplished using standard techniques for cell separation including, but not limited to, cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counterstreaming centrifugation), unit gravity separation, countercurrent distribution, electrophoresis and fluorescence-activated cell sorting. For a review of clonal selection and cell separation techniques, see Freshney, *Culture of Animal Cells: A Manual of Basic Techniques,* 2d Ed., A. R. Liss, Inc., New York, 1987, Ch. 11 and 12, pp. 137-168.

The isolation of fibroblasts may, for example, be carried out as follows: fresh tissue samples are thoroughly washed and minced in Hanks balanced salt solution (HBSS) in order to remove serum. The minced tissue is incubated from 1-12 hours in a freshly prepared solution of a dissociating enzyme such as trypsin. After such incubation, the dissociated cells are suspended, pelleted by centrifugation and plated onto culture dishes. All fibroblasts will attach before other cells, therefore, appropriate stromal cells can be selectively isolated and grown. The isolated fibroblasts can then be grown to confluency, lifted from the confluent culture and inoculated onto the three-dimensional matrix (see, Naughton et al., 1987, *J. Med.* 18 (3 and 4) 219-250). Inoculation of the three-dimensional framework with a high concentration of stromal cells, e.g., approximately $10^6$ to $5 \times 10^7$ cells/ml, will result in the establishment of the three-dimensional stromal tissue in shorter periods of time.

After inoculation of the stromal cells, the three-dimensional framework should be incubated in an appropriate nutrient medium. As previously mentioned, many commercially available media such as RPMI 1640, Fisher's, Iscove's, McCoy's, and the like may be suitable for use. It is important that the three-dimensional stromal cell cultures be suspended or floated in the medium during the incubation period in order to maximize proliferative activity. The culture is "fed" periodically and the conditioned media is recovered and processed as described below in Sections 5.6 and 5.7. Thus, depending upon the tissue to be cultured and the collagen types desired, the appropriate stromal cell(s) may be selected to inoculate the three-dimensional matrix.

During incubation of the three-dimensional stromal cell cultures, proliferating cells may be released from the matrix. These released cells may stick to the walls of the culture vessel where they may continue to proliferate and form a confluent monolayer. This should be prevented or minimized, for example, by removal of the released cells during feeding, or by transferring the three-dimensional stromal culture to a new culture vessel. The presence of a confluent monolayer in the vessel will "shut down" the growth of cells in the three-dimensional matrix and/or culture. Removal of the confluent monolayer or transfer of the culture to fresh media in a new vessel will restore proliferative activity of the three-dimensional culture system. It should be noted that the conditioned media is processed, if necessary, so that it does not contain any whole cells (unless whole cells are used for a specific application). Such removal or transfers should be done in any culture vessel which has a stromal monolayer exceeding 25% confluency. Alternatively, the culture system could be agitated to prevent the released cells from sticking, or instead of periodically feeding the cultures, the culture system could be set up so that fresh media continuously flows through the system. The flow rate could be adjusted to both maximize proliferation within the three-dimensional culture, and to wash out and remove cells released from the culture, so that they will not stick to the walls of the vessel and grow to confluence.

Other cells, such as parenchymal cells, may be inoculated and grown on the three-dimensional living stromal tissue.

b. Innoculation of Additional Cells into the Cell Cultures

Once the cell culture has reached a particular degree of growth, additional cells may be inoculated into the cell culture and cultured along with the cells of the cell culture. The additional cells are grown on the living tissue in vitro to form a cultured counterpart of the native tissue and condition the media by elaborating extracellular products into the media at ratios resembling physiological levels. A high concentration of cells in the inoculum will advantageously result in increased proliferation in culture much sooner than will low concentrations.

The cells chosen for inoculation will depend upon the tissue to be cultured, which may include, but is not limited to, bone marrow, skin, liver, pancreas, kidney, neurological tissue, adrenal gland, mucosal epithelium, and smooth muscle, to name but a few. Such cells with elaborate characteristic extracellular proteins such as certain growth factors into the media resulting in media optimized for certain tissue specific applications.

For example, and not by way of limitation, a variety of epithelial cells can be cultured on the living tissue. Examples of such epithelial cells include, but are not limited to, keratinocytes, oral mucosa and gastrointestinal (G.I.) tract cells. Such epithelial cells may be isolated by enzymatic treatment of the tissue according to methods known in the art, followed by expansion of these cells in culture and application of epithelial cells to, for example, the three-dimensional stromal support cell matrix. The presence of the stromal support provides growth factors and other proteins which promote normal division and differentiation of epithelial cells.

In general, this inoculum should include the "stem" cell (also called the "reserve" cell) for that tissue; i.e., those cells which generate new cells that will mature into the specialized cells that form the various components of the tissue.

The parenchymal or other surface layer cells used in the inoculum may be obtained from cell suspensions prepared by disaggregating the desired tissue using standard techniques described above for obtaining stromal cells. The entire cellular suspension itself could be used to inoculate the three-dimensional living stromal tissue. As a result, the regenerative cells contained within the homogenate will proliferate, mature, and differentiate properly on the matrix, whereas non-regenerative cells will not. Alternatively, particular cell types may be isolated from appropriate fractions of the cellular suspension using standard techniques described above for fractionating stromal cells. Where the "stem" cells or "reserve" cells can be readily isolated, these may be used to preferentially inoculate the three-dimensional stromal support. For example, when culturing bone marrow, the stroma may be inoculated with bone marrow cells, either fresh or derived from a cryopreserved sample. When culturing skin, the three-dimensional stroma may be inoculated with melanocytes and keratinocytes. When culturing liver, the three-dimensional stroma may be inoculated with hepatocytes. When culturing pancreas, the three-dimensional stroma may be inoculated with pancreatic endocrine cells. For a review of methods which may be utilized to obtain parenchymal cells from various tissues, see, Freshney, Culture of Animal Cells. A Manual of Basic Technique, 2d Ed., A. R. Liss, Inc., New York, 1987, Ch. 20, pp. 257-288.

In fact, different proportions of the various types of collagen deposited on the stromal matrix prior to inoculation can affect the growth of the later-inoculated tissue-specific cells. For example, for optimal growth of hematopoietic cells, the matrix should preferably contain collagen types III, IV and I in an approximate ratio of 6:3:1 in the initial matrix. For three dimensional skin culture systems, collagen types I and III are preferably deposited in the initial matrix. The proportions of collagen types deposited can be manipulated or enhanced by selecting fibroblasts which elaborate the appropriate collagen type. This can be accomplished using monoclonal antibodies of an appropriate isotype or subclass that is capable of activating complement, and which define particular collagen types. These antibodies and complement can be used to negatively select the fibroblasts which express the desired collagen type. Alternatively, the stromal cells used to inoculate the matrix can be a mixture of cells which synthesize the appropriate collagen type desired. The distribution and origins of various types of collagen is shown in Table I.

TABLE 1

DISTRIBUTIONS AND ORIGINS OF VARIOUS TYPES OF COLLAGEN

| Collagen Type | Principal Tissue Distribution | Cells of Origin |
|---|---|---|
| I | Loose and dense ordinary connective tissue; collagen fibers Fibrocartilage | Fibroblasts and reticular cells; smooth muscle cells |

TABLE 1-continued

DISTRIBUTIONS AND ORIGINS OF VARIOUS TYPES OF COLLAGEN

| Collagen Type | Principal Tissue Distribution | Cells of Origin |
|---|---|---|
| | Bone | Osteoblast |
| | Dentin | Odontoblasts |
| II | Hyaline and elastic cartilage | Chondrocytes |
| | Vitreous body of eye | Retinal cells |
| III | Loose connective tissue; reticular fibers | Fibroblasts and reticular cells |
| | Papillary layer of dermis | |
| | Blood vessels | Smooth muscle cells; endothelial cells |
| IV | Basement membranes | Epithelial and endothelial cells |
| | Lens capsule of eye | Lens fibers |
| V | Fetal membranes; placenta | Fibroblast |
| | Basement membranes | |
| | Bone | |
| | Smooth muscle | Smooth muscle cells Fibroblasts |
| VI | Connective Tissue | |
| VII | Epithelial basement membranes, anchoring fibrils | Fibroblasts, keratinocytes |
| | Cornea | Corneal fibroblasts |
| VIII | Cartilage | |
| IX | Hypertrophic cartilage | |
| X | Cartilage | Fibroblasts |
| XI | Papillary dermis | Fibroblasts |
| XII | Reticular dermis | Fibroblasts |
| XIV, undulin | P 170 bullous pemphigoid antigen | Keratinocytes |

During incubation, the cell culture system should be suspended or floated in the nutrient medium. Cultures should be fed with fresh media periodically. Again, care should be taken to prevent cells released from the culture from sticking to the walls of the vessel where they could proliferate and form a confluent monolayer. The release of cells from the culture appears to occur more readily when culturing diffuse tissues as opposed to structured tissues. For example, the skin culture is histologically and morphologically normal; the distinct dermal and epidermal layers do not release cells into the surrounding media. By contrast, the bone marrow cultures release mature non-adherent cells into the medium much the way such cells are released in marrow in vivo. As previously explained, should the released cells stick to the culture vessel and form a confluent monolayer, the proliferation of the three-dimensional culture will be "shut down". This can be avoided by removal of released cells during feeding, transfer of the culture to a new vessel, by agitation of the culture to prevent sticking of released cells to the vessel wall, or by the continuous flow of fresh media at a rate sufficient to replenish nutrients in the culture and remove released cells. As previously mentioned, the conditioned media is processed, if necessary, so that it is free of whole cells and cellular debris.

The growth and activity of cells in culture can be affected by a variety of growth factors such as insulin, growth hormone, somatomedins, colony stimulating factors, erythropoietin, epidermal growth factor, hepatic erythropoietic factor (hepatopoietin), and liver-cell growth factor. Other factors which regulate proliferation and/or differentiation include prostaglandins, interleukins, and naturally-occurring chalones.

C. Conditioned Growth Media and Cell Extract

1. Recovering the Conditioned Growth Media or Cell Extract from the Cell Cultures The resultant conditioned growth medium may be separated from the cell cultures by any means known to the skilled artisan. In one embodiment, the conditioned growth medium is pumped out of the cell culture system and processed for use. In some embodiments, the conditioned growth medium is recovered once the cell cultures have conditioned the growth medium to a sufficient extent (i.e., once the medium is conditioned so that extracellular proteins such as growth factors have reached desirable levels in the medium). Preferably, the conditioned growth medium is recovered at the later stages of growth of the tissue when the level of certain growth factors and connective tissue protein secretion is at its highest level (See FIG. 1). In a preferred embodiment, the conditioned growth medium is recovered after exposure of the growth medium to the cells at days 10 through day 14 of culturing.

The cell extract produced by the cell cultures can be isolated from the conditioned growth medium by any means known to the skilled artisan.

2. Processing the Conditioned Growth Media or Cell Extract

Following recovery of the conditioned growth medium or cell extract, it may be necessary to further process the resulting supernatant. Such processing may include, but are not limited to, concentration by a water flux filtration device or by defiltration using the methods described in *Cell & Tissue Culture: Laboratory Procedures*, supra, pp 29 D:0.1-29D:0.4.

Additionally, the medium may be concentrated 10 to 20 fold using a positive pressure concentration device having a filter with a 10,000 ml cut-off (Amicon, Beverly, Mass.).

Also, the conditioned growth medium or cell extract may be further processed for product isolation and purification to remove unwanted proteases, for example. The methods used for product isolation and purification so that optimal biological activity is maintained will be readily apparent to one of ordinary skill in the art. For example, it may be desirous to purify a growth factor, regulatory factor, peptide hormone, antibody, etc. Such methods include, but are not limited to, gel chromatography (using matrices such as sephadex) ion exchange, metal chelate affinity chromatography with an insoluble matrix such as cross-linked agarose, HPLC purification and hydrophobic interaction chromatography of the conditioned media. Such techniques are described in greater detail in *Cell & Tissue Culture: Laboratory Procedures*, supra. Depending upon the desired application of the conditioned growth medium or cell extract, and/or products derived thereof, appropriate measures must be taken to maintain sterility. Alternatively, sterilization may be necessary and can be accomplished by methods known to one of ordinary skill in the art, such as, for example, heat and/or filter sterilization taking care to preserve the desired biological activity.

3. Some Products Found in the Conditioned Growth Media or Cell Extract

Table 2 below lists the concentration of a number of growth factors determined by ELISA (enzyme linked immuno assay) to be in Applicants' conditioned medium which previously supported the growth of the cells grown in Dermagraft® tissue culture. It is believed that a cell extract according to the present invention would also contain these growth factors. It should be understood that the following list is not an all inclusive list of factors and is provided solely to further characterize the conditioned medium by providing the concentration of some of the biologically active factors present in the medium of the disclosure.

TABLE 2

Growth Factor Concentrations in Conditioned Medium as Measured by ELISA

| | |
|---|---|
| VEGF | 3.2 ng/ml |
| G-CSF | 2.3 ng/ml |
| IL-8 | 0.9 ng/ml |
| IL-8 | 3.2 ng/ml |
| KGF | 1.67 ng/ml |
| TGF-β | 0.8 ng/ml |

Figure 2:
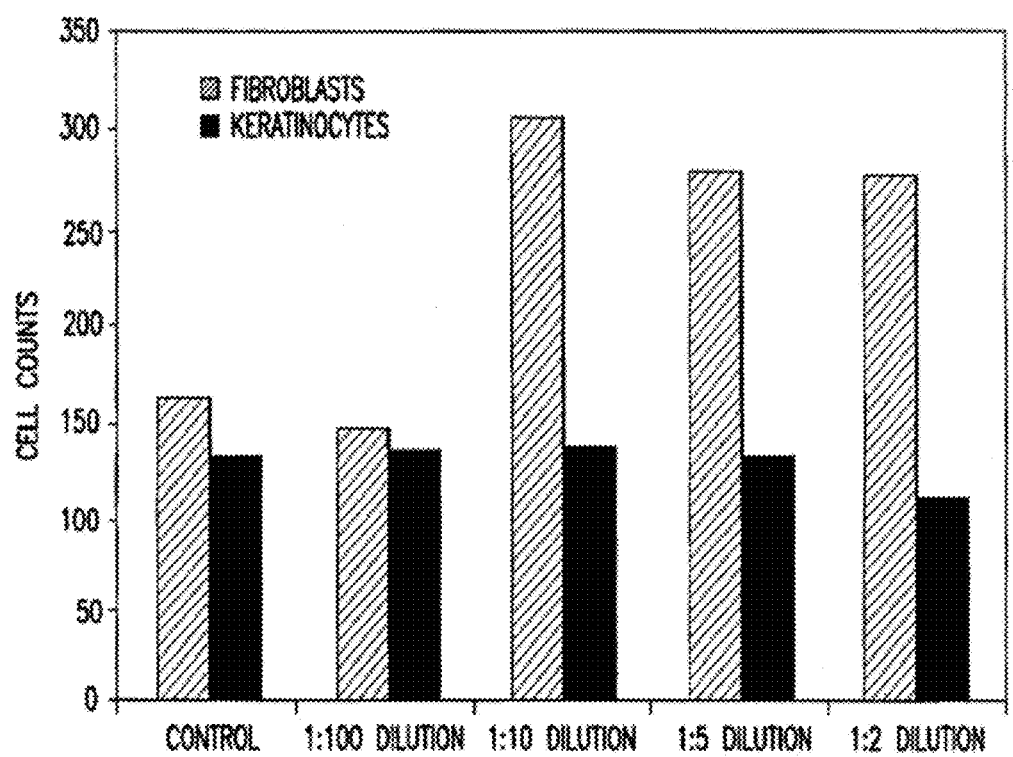
FIG. 2 is a graph representing the effect of extracellular matrix (removed from Transcyte™) and added at dilutions of 1:2, 1:5, 1:10, and 1:100 to monolayer cultures of human fibroblasts and keratinocytes. The most significant effect illustrated is at a 1:10 dilution of the matrix.

A variety of methods have been utilized to quantify and characterize the major molecular components secreted by fibroblasts found in the three-dimensional tissue cultures TransCyte™ and Dermagraft®). The human matrix proteins and glycosaminoglycans (GAGs) present in TransCyte™ and Dermagraft® include, but are not limited to, collagen I, III, fibronectin, tenascin, decorin, versican betaglycan, syndecan as well as other components (data not shown). These secreted proteins and GAGs serve major structural functions as well as stimulate cell division, migration, adhesion and signal transduction. The deposition of glycosaminoglycans (deposition volume is dependent on period of growth) and collagen (deposition volume is not dependent on period of growth) in the three-dimensional growth systems are illustrated in FIG. 1. The components have been measured by ELISA, Western blot analysis, immuno histochemistry and PCR. For example, some of the components found in TransCyte™ include collagen I, III, and VII (RNA), fibronectin, tenascin, thrombospondin 2, elastin, proteoglycans, decorin, versican as well as other components (data not shown). Activity of these components in tissue development, healing, and normal function have been well described. Additionally, Applicants describe certain effects of the human bioengineered matrix on cell function in vitro. For example, Applicants have noted that cell proliferation is increased by adding bioengineered matrix. To study its effects on cell proliferation, matrix was physically removed from TransCyte™ and Dermagraft® and added in varying dilutions to monolayer cultures of human fibroblasts and keratinocytes. The results of increased cell proliferation are shown in FIG. 2.

Further, Applicants note the effect of three dimensional conditioned medium on the preparation and composition of three-dimensional tissues was examined by measuring the amount of collagen secreted into the extracellular matrix of tissues cultured in the presence of serum-free medium, medium or three dimensional conditioned medium. The effect of three dimensional conditioned medium on the preparation and composition of three-dimensional tissues was examined by measuring the amount of collagen secreted into the extracellular matrix of tissues cultured in the presence of serum-free medium, medium or three dimensional conditioned medium. The conditioned medium of the disclosure significantly increases collagen deposition of tissue in vitro.

D. Metabolizing the Conditioned Growth Media or Cell Extract

1. The Yeast

The process of metabolizing the conditioned growth media or cell extract can occur with a variety of microorganisms such as, for example, yeast, *bacillus*, molds, plant cells and the like. Especially preferred for the present disclosure are ferments made using yeast. As used herein, the term "yeast" is meant to encompass a single yeast cell, multiple yeast cells and/or a culture of yeast cells. The yeast can be of various fungal families, known to those skilled in the art including, but not limited to: *Neurospora, Ceratostomella, Claviceps, Xylaria, Rosellinia, Helotium, Sclerotinia, Tulostoma, Rhizopogon, Truncocolumella, Mucor, Rhizopus, Entomophthora, Dictostylium, Blastocladia, Synchytrium, Saprolegnia, Peronospora, Albugo, Pythium, Phytophthora, Plasmodiophora, Tuber, Hydnum, Lecanora, Roccella, Pertusaria, Usnea, Evernia, Ramalina, Alectoria, Cladonia, Parmelia, Cetraria, Agaricus, Cantharellus, Omphalotus, Coprinus, Lactarius, Marasmius, Pleurotus, Pholiota, Russula, Lactarius, Stropharia, Entoloma, Lepiotaceae, Corticium, Pellicularia, Tricholoma, Volvaria, Clitocybe, Flammulina, Saccharomyces, Schizosaccharomyces, Saccharomycetaceae, Eurotium, Aspergillus, Thielavia, Peziza, Plectania, Morchella, Wynnea, Helvella, Gyromitra, Phallales, Dictyophera, Mutinus, Clathrus, Pseudocolus, Lycoperdon, Calvatia, Geastrum, Radiigera, Astreus, Nidularia, Gastrocybe, Macowanites, Gastroboletus, Albatrellus, Neolentinus, Nigroporus, Oligoporus, Polyporus, Fistulina, Fomes, Boletus, Fuscoboletinus, Leccinum, Phylloporus, Suillus, Strobilomyces, Boletellus, Tremella, Auricularia, Dacrymyces, Melampsora, Cronartium, Puccinia, Gymnosporangium, Tilletia, Urocystis, Septobasidium, Hygrocybe, Hygrophorus, Hygrotrama, Neohygrophorus, Cortinarius, Gymnopilus, Trichophyton, Microsporum, Monilia, Candida, Cercosporella, Penicillium, Blastomyces, Cercospora, Ustilaginoidea, Tuber cularia, Fusarium, Rhizoctinia, Ozonium, Sclerotium, Geoglossum,* or *Armillaria*. Of particular interest are the fungi belonging to the family Saccharomycetaceae. Of greater interest are the fungi belonging to the genus *Pichia*. Of most interest are the fungi belonging to the species pastoris. In a preferred embodiment, *Pichia pastoris* is used in the fermentation process. In some embodiments, the yeast is aerobically grown.

2. Fermentation Process

The yeast fermentation process can be carried out in a stirred tank bio-reactor. Examples of such bioreactors might include for example, fermentors available from New Brunswick Scientific, Edison N.J. or Applikon Biotechnology Foster City Calif.

The yeast extracts of the present disclosure include cytoplasmic and extra-cellular components of the yeast which include, but are not limited to, the nutrient broth, cellular protein material, cellular nucleic material, cellular protoplasmic material and/or cell wall components. In some embodiments, the extracts are relatively water soluble, for example, equal or more than 1-gram of yeast extracts dissolve in 1-gram of water. The extracts may also be soluble in water/organic solvent mixtures such as, but not limited to, aqueous glycols and aqueous glycerols.

3. Recovering/Processing the Metabolized Conditioned Growth Media or Metabolized Cell Extract The metabolized conditioned growth media or metabolized cell extract may be recovered and/or processed according to the procedures described above for recovering and processing the conditioned growth media or cell extract. In some embodiments, the processing includes several steps and may involve the use of techniques, including but not limited to continuous flow centrifugation, lenticular dead-end filtration for clarification of bio-mass, and tangential flow filtration with sterile and ultra-filtration capabilities. In one embodiment, the final processing step includes tangential flow filtration of a specific molecular weight cut-off in order to selectively target bio-active components. See, e.g., "Yeast Protocols" W. Xiao ed. (Humana Press 2006), which is incorporated by reference herein.

E. Activity/Characterization of the Metabolized Conditioned Growth Media or Metabolized Cell Extract During the yeast metabolism described above, therapeutic products present in the conditioned growth media and cell extract, including but not limited to enzymes, hormones, cytokines, antigens, antibodies, clotting factors, and regulatory proteins, are metabolized by the yeast. The term metabolized is known to those skilled in the art but essentially means that the yeast begin the process of digesting the components of the conditioned nutrient media or cell extract. The process of metabolizing can render larger molecules as small, more readily available components that are more useful for the applications of the present invention than the unmetabolized conditioned growth media or cell extracts. Therapeutic proteins that may be metabolized include, but are not limited to, inflammatory mediators, angiogenic factors, Factor VIII, Factor IX, erythropoietin (EPO), alpha-1 antitrypsin, calcitonin, glucocerebrosidase, human growth hormone and derivatives, low density lipoprotein (LDL), and apolipoprotein E, IL-2 receptor and its antagonists, insulin, globin, immunoglobulins, catalytic antibodies, the interleukins (ILs), insulin-like growth factors, superoxide dismutase, immune responder modifiers, BMPs (bone morphogenic proteins) parathyroid hormone and interferon, nerve growth factors, tissue plasminogen activators, and colony stimulating factors (CSFs). These metabolized components may maintain the activity of their precursors, or may be transformed to have greater enhanced activity, including the downregulation or upregulation of various physiological systems that affect, for example, skin maintenance and condition.

The medium or extract may be further processed to concentrate or reduce one or more metabolized factor or component contained within the medium or extract, for example, enrichment of a metabolized growth factor using immunoaffinity chromatography or, conversely, removal of a less desirable component, for any given application as described herein.

In other embodiments, the metabolized conditioned growth media and/or metabolized cell extract of the present disclosure contains one or more cytoplasmic and extracellular components of the yeast which include, but are not limited to, the nutrient broth, cellular protein material, cellular nucleic material, cellular protoplasmic material and/or cell wall components.

III. Compositions

In one embodiment, the disclosure provides compositions comprising the metabolized conditioned growth medium or the metabolized cell extract, and an acceptable carrier. In some embodiments, the composition is a personal care composition.

In some embodiments, the metabolized conditioned growth medium or the metabolized cell extract is present in the composition in an amount of about 0.0001% to about 95% by weight of the composition. In other embodiments, the metabolized conditioned growth medium or the metabolized cell extract is present in the composition in an amount of about 0.01% to about 50% by weight of the composition. In other embodiments, the metabolized conditioned growth medium or the metabolized cell extract is present in the composition in an amount of about 5% to about 30% by weight of the composition. In other embodiments, the metabolized conditioned growth medium or the metabolized cell extract is present in the composition in an amount of about 10% to about 20% by weight of the composition. In other embodiments, the metabolized conditioned growth medium or the metabolized cell extract is present in the composition in an amount of about 13% to about 17% by weight of the composition. In other embodiments, metabolized conditioned growth medium or the metabolized cell extract is present in the composition in an amount of about 0.01% to about 10% by weight of the composition. In one embodiment, the metabolized conditioned growth medium or the metabolized cell extract is present in the composition in an amount of about 10%, about 15%, or about 20% by weight of the composition.

In other embodiments, the composition further comprises at least one of water, a preservative, a surfactant, an emulsifier, a conditioner, an emollient, a wax, an oil, a polymer, a thickener, a fixative, a colorant, a humectant, a moisturizer, a stabilizer, a diluent, a solvent and a fragrance. Non-limiting examples of additional ingredients of the compositions include, but are not limited to, Palmitoyl tripeptide 5, hydrolyzed silk (Sericin), Dipalmitoyl hydroxyproline, Ergothioneine (EGT), Ubiquinone (Coenzyme Q10), *Camellia Sinensis* (Green Tea) Leaf Extract, Tetrahexyldecyl Ascorbate, Tocopheryl Acetate, *Rubus Fruticosus* (Blackberry) Leaf Extract, *Saccharomyces* Ferment Filtrate Lysate, Alpha-Arbutin, Gamma Aminobutyric Acid, and/or Hyaluronic Filling Spheres.

In one embodiment, the composition further comprises at least one preservative. Suitable preservatives include, but are not limited to, acids, alcohols, glycols, parabens, quaternary-nitrogen containing compounds, isothiazolinones, aldehyde-releasing compounds and halogenated compounds. Illustrative alcohols include phenoxyethanol, isopropyl alcohol, and benzyl alcohol; illustrative glycols include propylene, butylene and pentylene glycols; illustrative parabens include (also known as parahydroxybenzoic acids) methyl, propyl and butyl parabens; illustrative quaternary nitrogen containing compounds include benzalkonium chloride, Quarternium 15; illustrative isothiazoles include methylisothiazoline, methychlorolisothiazoline; illustrative aldehyde releasing agents include DMDM hydantion, imiadolidinyl urea and diazolidinyl urea; illustrative antioxidants include butylated hydroxytoluene, tocopherol and illustrative halogenated compounds include triclosan and chlorohexidene digluconate. Examples of preservatives useful for the purpose of the present disclosure can be found in Steinberg, D. "Frequency of Use of Preservatives 2007". Cosmet. Toilet. 117, 41-44 (2002) and, "Preservative Encyclopedia" Cosmet. Toilet. 117, 80-96 (2002). In addition, enzyme preservative systems such as those described in the article by Ciccognani D. Cosmetic Preservation Using Enzymes, in "Cosmetic and Drug Microbiology", Orth D S ed., Francis & Taylor, Boca Raton, Fla. (2006) can also be effective for use with the composition of the present disclosure.

In one embodiment, the composition further comprises an active ingredient. Suitable active ingredients include, but are not limited to botanicals, nutraceuticals, cosmeceuticals, therapeutics, pharmaceuticals, antimicrobials, steroidal hormones, antidandruff agents, anti-acne components, sunscreens, antibiotics, antivirals, antifungals, steroids, analgesics, antitumor drugs, investigational drugs or any compounds which would result in a complimentary or synergistic combination with the factors in the metabolized conditioned media or metabolized cell extract.

The compositions may be in the form of tablets, capsules, skin patches, inhalers, eye drops, nose drops, ear drops, suppositories, creams, ointments, injectables, hydrogels and into any other appropriate formulation known to one of skill in the art. For oral administration the pharmaceutical compositions may take the form of, for example, tablets or capsules prepared by conventional means with acceptable excipients or carriers such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolae); or wetting agents (e.g., sodium lauryl sulphate). Tablets may be coated using methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with acceptable excipients or carriers such as suspending agents (e.g., sorbitol syrup cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

In one embodiment, the compositions are in a form suitable for cosmetic application including, but not limited to, lotions, ointments, creams, sprays, spritzes, aqueous or aqueous-alcoholic mixture gels, mousses, patches, pads, masks, moistened clothes, wipes, solid sticks, clear sticks, lip sticks, aerosol creams, anhydrous powders, talcs, tonics, oils, emulsions or bath salts.

In one embodiment, the metabolized conditioned growth medium or the metabolized cell extract in the composition is present in a chemical delivery vehicle. Chemical delivery vehicles include, but are not limited to, liposomes, niosomes, sub-micron emulsions, polymeric encapsulates, gels, creams, lotions, and combinations thereof. In some embodiments, the metabolized conditioned growth medium or the metabolized cell extract is encapsulated within an encapsulant.

The compositions of the disclosure may be delivered to a subject via a variety of routes using standard procedures well known to those of skill in the art. For example, such delivery may be site-specific, oral, nasal, intravenous, subcutaneous, intradermal, transdermal, intramuscular or intraperitoneal administration. Also, they may be formulated to function as controlled or slow release vehicles.

The metabolized conditioned growth medium and/or metabolized cell extract may be used in any state, i.e., liquid or solid, frozen lyophilized or dried into a powder, as a film for topical wound treatments and anti-adhesion applications, as an injectable, see PCT WO 96/39101, incorporated herein by reference it its entirety.

Alternatively, the conditioned cell medium of the present disclosure may be formulated with polymerizable or crosslinking hydrogels as described in U.S. Pat. Nos. 5,709,854; 5,516,532; 5,654,381; and WO 98/52543, each of which is incorporated herein by reference in its entirety. Examples of materials which can be used to form a hydrogel include modified alginates. Alginate is a carbohydrate polymer isolated from seaweed, which can be cross-linked to form a hydrogel by exposure to a divalent cation such as calcium, as described, for example in WO 94/25080, the disclosure of which is incorporated herein by reference. Alginate is ionically cross-linked in the presence of divalent cations, in water, at room temperature, to form a hydrogel matrix. As used herein, the term "modified alginates" refers to chemically modified alginates with modified hydrogel properties.

Additionally, polysaccharides which gel by exposure to monovalent cations, including bacterial polysaccharides, such as gellan gum, and plant polysaccharides, such as carrageenans, may be cross-linked to form a hydrogel using methods analogous to those available for the cross-linking of alginates described above.

Modified hyaluronic acid derivatives are particularly useful. As used herein, the term "hyaluronic acids" refers to natural and chemically modified hyaluronic acids. Modified hyaluronic acids may be designed and synthesized with preselected chemical modifications to adjust the rate and degree of cross-linking and biodegradation.

Covalently cross-linkable hydrogel precursors also are useful. For example, a water soluble polyamine, such as chitosan, can be cross-linked with a water soluble diisothiocyanate, such as polyethylene glycol diisothiocyanate.

Alternatively, polymers may be utilized which include substituents which are cross-linked by a radical reaction upon contact with a radical initiator. For example, polymers including ethylenically unsaturated groups which can be photochemically cross-linked which may be utilized, as disclosed in WO 93/17669, the disclosure of which is incorporated herein by reference. In this embodiment, water soluble macromers that include at least one water soluble region, a biodegradable region, and at least two free radical-polymerizable regions, are provided. Examples of these macromers are PEG-oligolactyl-acrylates, wherein the acrylate groups are polymerized using radical initiating systems, such as an eosin dye, or by brief exposure to ultraviolet or visible light. Additionally, water soluble polymers which include cinnamoyl groups which may be photochemically cross-linked may be utilized, as disclosed in Matsuda et al., ASAID *Trans.*, 38: 154-157 (1992).

The preferred polymerizable groups are acrylates, diacrylates, oligoacrylates, dimethacrylates, oligomethacrylates, and other biologically acceptable photopolymerizable groups. Acrylates are the most preferred active species polymerizable group.

Naturally occurring and synthetic polymers may be modified using chemical reactions available in the art and described, for example, in March, "Advanced Organic Chemistry", $4^{th}$ Edition, 1992, Wiley-Interscience Publication, New York.

Polymerization is preferably initiated using photo initiators. Useful photo initiators are those which can be used to initiate polymerization of the macromers without cytotoxicity and within a short time frame, minutes at most and most preferably seconds.

Numerous dyes can be used for photopolymerization. Suitable dyes are well known to those of skill in the art. Preferred dyes include erythrosin, phloxime, rose bengal, thonine, camphorquinone, ethyl eosin, eosin, methylene blue, riboflavin, 2,2-dimethyl-2-phenylacetophenone, 2-methoxy-2-phenylacetophenone, 2,2-dimethoxy-2-phenyl acetophenone, other acetophenone derivatives, and camphorquinone. Suitable cocatalysts include amines such as N-methyl diethanolamine, N,N-dimethyl benzylamine, triethanol amine, trithylamine, dibenzyl amine, N-benzylethanolamine, -isopropyl benzylamine. Triethanolamine is a preferred cocatalyst.

In another embodiment, the metabolized conditioned growth media and/or metabolized cell extract of the disclosure, or alternatively particular metabolized extracellular matrix proteins elaborated into the media, are used to provide an excellent substance to coat sutures. The metabolized, naturally secreted extracellular matrix provides the conditioned media with an activity of type I and type III collagens, fibronectin, terascin, glycosaminologycans, acid and basic FGF, TGF-α and TGF-β, KGF, versican, decorin and various other secreted human dermal matrix proteins. Similarly, the conditioned cell media of the disclosure or the extracellular matrix proteins derived from the conditioned media may be used to coat conventional implantation devices, including vascular prosthesis, in surgical approaches to correct defects in the body—resulting in superior implantation devices. The implants should be made of biocompatible, inert materials that replace or substitute for the defective function and made of either non-biodegradable materials or biodegradable materials. By coating implantation devices with the medium containing these extracellular proteins, the implant invites proper cellular attachments resulting in superior tissue at the implantation site. Thus, sutures, bandages, and implants coated with conditioned cell media, or proteins derived from the media, enhance the recruitment of cells, such as leukocytes and fibroblasts into the injured area and induce cell proliferation and differentiation resulting in improved wound healing.

In another embodiment, the metabolized conditioned growth media and/or metabolized cell extract of the disclosure may be formulated with a pharmaceutically acceptable carrier as a vehicle for internal administration. Also, the medium may be further processed to concentrate or reduce one or more factor or component contained within the medium, for example, enrichment of a growth factor or other protein using immunoaffinity chromatography or, conversely, removal of a less desirable component, for any given application as described herein.

IV. Methods for Treating or Preventing Conditions

In one embodiment, the disclosure provides methods for preventing or treating a condition in a subject comprising administering to the subject a therapeutically effective amount of a composition comprising: an acceptable carrier and a metabolized conditioned growth medium.

In another embodiment, the disclosure provides methods for preventing or treating a condition in a subject comprising administering to the subject a therapeutically effective amount of a composition comprising: an acceptable carrier and a metabolized cell extract.

Conditions to be treated include, but are not limited to, skin conditions, including cosmetic defects, congenital defects, hair loss and acquired defects. In some embodiments, the conditions to be treated include, but are not limited to, fine lines and wrinkles; age spots and dyspigmentation; decreased skin texture, tone and elasticity; roughness and photo damage; decreased ability of skin to regenerate itself; environmental damage; decreased smoothness and tightness of skin; age spots; fine and coarse lines and wrinkles; fine and coarse periocular wrinkles; nasolabial folds; facial fine and coarse lines; decreased skin radiance and evenness; decreased skin firmness; hyperpigmentation; dark spots and/or patches; decreased skin brightness and youthful appearance; photoaged skin; intrinsically and extrinsically aged skin; abnormal skin cellular turnover; decreased skin barrier; decrease of skin's ability to retain moisture; brown and red blotchiness; redness; abnormal skin epidermal thickness; reduction of dermal epidermal junction; increased pore size and number of pores; or a combination thereof.

A. Skin Conditions

In some embodiments, the condition to treat or prevent is a skin condition. In other embodiments, the skin condition is a cosmetic defect, a congenital defect, hair loss or an acquired defect Skin conditions also include, but are not limited to, fine lines and wrinkles; age spots and dyspigmentation; decreased skin texture, tone and elasticity; roughness and photo damage; decreased ability of skin to regenerate itself; environmental damage; decreased smoothness and tightness of skin; age spots; fine and coarse lines and wrinkles; fine and coarse periocular wrinkles; nasolabial folds; facial fine and coarse lines; decreased skin radiance and evenness; decreased skin firmness; hyperpigmentation; dark spots and/or patches; decreased skin brightness and youthful appearance; photoaged skin; intrinsically and extrinsically aged skin; abnormal skin cellular turnover; decreased skin barrier; decrease of skin's ability to retain moisture; brown and red blotchiness; redness; abnormal skin epidermal thickness; reduction of dermal epidermal junction; increased pore size and number of pores; or a combination thereof.

In one non-limiting example, a topical composition as described herein is applied to the skin. Application of the compositions disclosed herein rejuvenates sun damaged and aging skin; improves the appearance of fine lines and wrinkles; promotes cell renewal; diminishes the appearance of age spots and dyspigmentation; improves skin tone, texture and elasticity; reduces roughness and photo damage; prevents or reduces environmental damage; plumps the skin; brightens the skin; lightens the skin; strengthens the ability of skin to regenerate itself; improves the appearance of age spots; brightens and lightens age spots; improves skin firmness, elasticity, resiliency; smoothes, tightens, or fills in fine lines on the skin; reduces the appearance of dark circles under the eye; improves lip texture or condition; enhances natural lip color; increases lip volume; promotes epithelialization of post-procedure skin; restores the skin's barrier or moisture balance; improves the appearance of age spots; improves the appearance of skin pigmentation, or a combination thereof.

In certain embodiments, administration of a composition described herein may result in at least a 2-fold improvement of one or more symptoms or conditions. Folds improvement of one or more symptoms or conditions include, but are not limited to, 3-fold, 5-fold, 10-fold, 15-fold, 20-fold, 25-fold, 75-fold, 100-fold or more, or any number therebetween. In certain embodiments, administration of a composition described herein may result in improvement of about 1% to about 100%, about 10% to about 90%, about 20% to about 80%, about 30% to about 70%, about 40% to about 60%, or about 50%. In other embodiments, administration of a composition described herein may result in improvement of one or more symptoms or conditions of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 100%, about 125%, about 150% or more of one or more symptoms or conditions.

The effect of the metabolized conditioned growth media and/or metabolized cell extract described above to influence human skin can be measured in a number of ways known to those skilled in the art. In particular, the metabolized conditioned growth media and/or metabolized cell extract described above can be screened for their effects on skin by employing analytical techniques such as, for example, human genomic microarrays on specific skin cells such as keratinocytes or fibroblasts, or by protein expression analysis on individual skin cells, tissue models or ex vivo or in vivo skin models. In these testing models, specific genes and or proteins may be up-regulated or down-regulated as a result of the extract treatment. Genes and proteins that are capable of regulating skin conditions are of particular interest in the screening. Of particular interest for the purpose of the present disclosure are genes and proteins related to inflammation, extracellular matrix expression, melanin regulation, skin moisturization, exfoliation and the like. Of particular interest are proteins related to cyclooxygenase expression, in particular cyclooxygenase-1 and 2 and also extracellular matrix protein expression, in particular, types, I, IV and VI collagen expression, and elastin and fibronectin expression. In addition, the influence of the extract on skin melanin expression is also of considerable interest.

The effect of the metabolized conditioned growth media and/or metabolized cell extract of the disclosure on expression of these and other important cutaneous proteins can be monitored by human genomic microarray analysis and protein expression as well as by non-invasive test methods well-known to those in skilled in the art, including, but not limited to, improved moisturization, wrinkle reduction, reduced pigmentation, improved skin tone and the like. Application of the metabolized conditioned growth media and/or metabolized cell extract of the disclosure can manifest itself by measured reductions in skin wrinkles, for example, as measured by techniques such as SiIFIo silicone modeling, PRIMOS and VISIO photographic systems and the like. In addition, moisturization might be measured using transepidermal water loss (TEWL) or cutometer or corneometric measurements. Likewise, skin pigmentation could be measured using a chromometer. Such testing technologies are well-known to those skilled in the art and can be found in the "Handbook of Non-Invasive Methods and the Skin", $2_{nd}$ edition, Serup J, Jemec G B E, Grove G L (ed.), Taylor and Francis Boca Raton Fla. 2006.

Human gene microarray analysis on human epidermal keratinocytes indicates that the metabolized conditioned growth medium up-regulates several genes involved in various skin functions. See Example 18. It is thus appreciated that the yeast-metabolized conditioned growth media or metabolized cell extract according to the present disclosure can be used in personal care compositions for the treatment of skin conditions.

B. Wound Healing Applications

The metabolized conditioned growth media and/or metabolized cell extract of the disclosure may be processed to promote wound and burn healing. When tissue is injured, polypeptide growth factors, which exhibit an array of biological activities, are released into the wound to promote healing. Wound healing is a complex process that involves several stages and is capable of sealing breaches to the integument in a controlled manner to form functionally competent tissue. The process begins with hemostasis followed by an inflammatory phase involving neutrophils and macrophages. The process continues with the development of granulation tissue and re-epithelialization to close the wound. Subsequently, scar tissue forms and is remodeled over the succeeding months to an approximation of the original anatomical structure. Ideally, scar tissue is minimal so that healthy tissue, functionally competent tissue which histologically and physiologically resembles the original normal tissue, may form.

Each stage of the healing process is controlled by cellular interactions through regulatory proteins such as cytokines, growth factors, and inflammatory mediators as well as cell contact mechanisms. For example, inflammatory mediators such as IL-6, IL-8, and G-CSF induce lymphocyte differentiation and acute phase proteins, as well as neutrophil infiltration, maturation and activation, processes that are important in the inflammatory stages of wound healing. Other examples of regulatory proteins involved in the wound healing process are VEGF that induces angiogenesis during inflammation and granulation tissue formation, the BMP's which induce bone formation, KGF that activates keratinocytes and TGF-$\beta$1 that induces deposition of extracellular matrix.

In chronic wounds, the healing process is interrupted at a point subsequent to hemostasis and prior to re-epithelialization, and is apparently unable to restart. Most of the inflammation seen in the wound bed is related to infection, but the inflammation gives rise to an environment rich in proteases that degrade regulatory proteins and thus interfere with the wound healing process.

The metabolized conditioned growth media and/or metabolized cell extract of the disclosure contains activity thought to be important in wound healing and which have been shown to be depleted in in vivo models of wound healing. For example, the metabolized conditioned growth media and/or metabolized cell extract of the disclosure may contain an activity of one or more of a number of growth factors that support healing process, such as VEGF, G-CSF, IL-8, KGF, and TGF-$\beta$. Furthermore, in some medical conditions, such as diabetes, some of the regulatory proteins needed for wound healing are in short supply. For example, it has been found in a mouse model of non-insulin-dependent diabetes (e.g., the db/db mouse) that secretion of VEGF and PDGF and expression of the PDGF receptor are all depressed in wounds compared to the levels in wounds of normal mice.

Also, the metabolized conditioned growth media and/or metabolized cell extract of the disclosure is useful in the treatment of other types of tissue damage, e.g., traumatic or congenital, wherein the repair and/or regeneration of tissue defects or damage is desired since an activity of many of these growth factors are found in Applicants' metabolized conditioned growth media and/or metabolized cell extract, including, for example, fibroblast growth factors (FGFs), platelet derived growth factors (PDGFs), epidermal growth factors (EGFs), bone morphogenetic proteins (BMPs) and transforming growth factors (TGFs); as well as those which modulate vascularization, such as vascular endothelial growth factor (VEGF), keratinocyte growth factor (KGF), and basic FGF; angiogenesis factors, and antiangiogenesis factors. Stress proteins, such as GR 78 and MSP90 induce growth factors such as TGF-$\beta$. TGF-$\beta$, including TGF $\beta$-1, TGF $\beta$-2, TGF $\beta$-3, TGF $\beta$-4 and TGF $\beta$-5, regulate growth and differentiation and accelerate wound healing (Noda et al. 1989, Endocrin. 124: 2991-2995; Goey et al. 1989, *J. Immunol.* 143: 877-880, Mutoe et al. 1987, *Science* 237: 1333-1335). Mitogens, such as PDGF increase the rate of cellularity and granulation in tissue formation (Kohler et al. 1974, *Exp. Cell. Res.* 87: 297-301). As previously mentioned, the cells are preferably human to minimize immunogenicity problems.

Because the metabolized conditioned growth media and/or metabolized cell extract of the disclosure contains an activity of an array of wound healing factors, the conditioned media is advantageously used in the treatment of wound and burn healing including skin wounds, broken bones, gastric ulcers, pancreas, liver, kidney, spleen, blood vessel injuries and other internal wounds. Further, the metabolized conditioned growth media and/or metabolized cell extract of the disclosure may be combined with other medicinal ingredients such as antibiotics and analgesics.

Embodiments include formulations of the metabolized conditioned growth media and/or metabolized cell extract of the disclosure with a salve or ointment for topical applications.

Alternatively, the metabolized conditioned growth media and/or metabolized cell extract of the disclosure may be combined with a bandage (adhesive or non-adhesive) to promote and/or accelerate wound healing.

Wounds at specialized tissues may require medium conditioned by that specialized tissue. For example, injuries to neuronal tissues may require proteins contained in medium conditioned by neuronal cell cultures. Specific products may be derived, or alternatively, the metabolized conditioned growth media and/or metabolized cell extract may be enriched by immunoaffinity chromatography or enhanced expression of a desired protein from the specific medium such as, for example, NGF. NGF-controlled features include, but are not limited to, the cholinergic neurotransmitter function (acetylcholinesterase (AChE) and the acetylcholine-synthesizing enzyme (ChAT)), neuronal cell size, and expression of Type II NGF receptors; NGF is secreted into the conditioned medium conditioned by glial and other neuronal cells cultured on a three-dimensional stromal tissue, which can then be used in a composition for nerve healing.

Deficits of endogenous NGF aggravate certain human neurodegenerative disorders and there is an apparent inability of injured adult CNS neurons to regenerate. Specifically, injury to a nerve is followed by degeneration of the nerve fibers distal to the injury, the result of isolation of the axon from the cell body. In the central nervous system, there is no significant growth at the site of injury typically leading to death of the damaged neuron. NGF plays a crucial role in the regenerative capabilities of adult CNS cholinergic neurons at the cell body level (e.g., septum), the intervening tissue spaces (e.g., nerve bridge) and the reinervation area (e.g., hippocampal formation). Additionally, NGF may be beneficial in improving cognitive defects. Metabolized conditioned growth media and/or metabolized cell extract conditioned with glial cells for example, can supply an activity of exogenous NGF and other nerve growth factors so that new axons can grow out from the cut ends of the injured nerve (e.g., develop a growth cone) elongating to the original site of the connection.

Further, injury to the brain and spinal cord is often accompanied by a glial response to the concomitant axonal degeneration, resulting in scar tissue. This scar tissue was initially thought to be a physical barrier to nerve growth, however, of greater significance is the presence or absence of neuronotropic factors in the extra neuronal environment. Astrocytes appear to be capable of synthesizing laminin in response to injury (laminin can also be found in the metabolized conditioned growth media). Collagen and fibronectin, and especially laminin, have been found to promote the growth of neurities from cultured neurons or neuronal explants in vitro. These extracellular matrix proteins appear to provide an adhesive substratum which facilitates the forward movement of the growth cone and elongation of the axon. Thus, the presence of neuronotropic factors and a supportive substratum are required for successful nerve regeneration since regeneration appears to require that: the neuronal cell body be capable of mounting the appropriate biosynthetic response; and the environment surrounding the injury site be capable of supporting the elongation and eventual functional reconnection of the axon. Metabolized conditioned growth media and/or metabolized cell extract conditioned by nerve cells such as astrocytes and glial cells contains an activity of neuronotropic growth factors and extracellular matrix proteins necessary for nerve regeneration in brain and spinal cord injuries. Thus, in one embodiment, the metabolized conditioned growth media and/or metabolized cell extract is formulated for the treatment of such injuries.

In other embodiments, the treatment of skin, bones, liver, pancreas, cartilage, and other specialized tissues may be treated with media conditioned by their respective specialized cell types, preferably cultured in three-dimensions, resulting in a conditioned medium containing an activity of one or more characteristic extracellular proteins and other metabolites of that tissue type useful for treating wounds to that respective tissue type.

The metabolized conditioned growth media and/or metabolized cell extract of the disclosure may also be added to devices used in periodontal surgery in order to promote uniform tissue repair, to provide biodegradable contact lenses, corneal shields or bone grafts, to provide surgical space fillers, to promote soft tissue augmentation, particularly in the skin for the purpose of reducing skin wrinkles, and as urinary sphincter augmentation, for the purpose of controlling incontinence.

In another embodiment, the compositions may be lyophilized/freeze-dried and added as a wound filler (e.g., fill holes left from hair plugs for implantation) or added to existing wound filling compositions to accelerate wound healing. In another embodiment, the medium is conditioned with genetically engineered cells to increase the concentration of wound healing proteins in the medium. For example, the cells may be engineered to express gene products such as any of the growth factors listed above.

C. The Repair and Correction of Congenital Anomalies, Acquired Defects and Cosmetic Defects As disclosed above, the metabolized conditioned growth media and/or metabolized cell extract of the disclosure may also be used to repair and correct a variety of anomalies, both congenital and acquired as well as cosmetic defects, both superficial and invasive. In one embodiment the metabolized conditioned growth media and/or metabolized cell extract of the disclosure may be used to treat or prevent fine lines and wrinkles; age spots and dyspigmentation; decreased skin texture, tone and elasticity; roughness and photo damage; decreased ability of skin to regenerate itself; environmental damage; decreased smoothness and tightness of skin; age spots; fine and coarse lines and wrinkles; fine and coarse periocular wrinkles; nasolabial folds; facial fine and coarse lines; decreased skin radiance and evenness; decreased skin firmness; hyperpigmentation; dark spots and/or patches; decreased skin brightness and youthful appearance; photoaged skin; intrinsically and extrinsically aged skin; abnormal skin cellular turnover; decreased skin barrier; decrease of skin's ability to retain moisture; brown and red blotchiness; redness; abnormal skin epidermal thickness; reduction of dermal epidermal junction; increased pore size and number of pores; or a combination thereof. In another embodiment, the metabolized conditioned growth media and/or metabolized cell extract of the disclosure may be used to rejuvenate sun damaged and aging skin; improve the appearance of fine lines and wrinkles; promote cell renewal; and/or improve skin tone, texture and/or firmness. In another embodiment, the metabolized conditioned growth media and/or metabolized cell extract of the disclosure may be used to plump the skin and/or brighten and/or lighten the skin. In another embodiment, the metabolized conditioned growth media and/or metabolized cell extract of the disclosure may be used to strengthen the skin's ability to regenerate itself; improve the appearance of age spots; and/or improve skin firmness, elasticity, and/or resiliency. In another embodiment, the metabolized conditioned growth media and/or metabolized cell extract of the disclosure may be used to smooth, tighten, and/or fill in fine lines on the skin. In another embodiment, the metabolized conditioned growth media and/or metabolized cell extract of the disclosure may be used to reduce the appearance of dark circles under the eye. In another embodiment, the metabolized conditioned growth media and/or metabolized cell extract of the disclosure may be used to improve lip texture and/or condition, enhance natural lip color, and/or increase lip volume. In another embodiment, the metabolized conditioned growth media and/or metabolized cell extract of the disclosure may be used to promote epithelialization of post-procedure skin and/or restore the skin's barrier and/or moisture balance. In another embodiment, the metabolized conditioned growth media and/or metabolized cell extract of the disclosure may be used to improve the appearance of age spots and/or pigmentation.

For example, compositions comprising metabolized conditioned growth media and/or metabolized cell extract of the disclosure may be added in any form and may be used in a hydrogel, injectable, cream, ointment, and may even be added to eye shadow, pancake makeup, compacts or other cosmetics to fortify the skin topically.

In another embodiment, topical or application by any known method such as injection, oral, etc., of the metabolized conditioned growth medium is made to reverse and/or prevent wrinkles and a number of the deleterious effects induced by UV light, exposure to a variety of pollutants and normal aging for example.

Additionally, in another embodiment, the metabolized conditioned growth media and/or metabolized cell extract of the disclosure is used to reduce cell aging and inhibit the activity of the factors which cause skin cancer. That the metabolized conditioned growth media and/or metabolized cell extract has antioxidant activity is shown in the examples. Again, application to a mammal may be topical or application by any known method such as injection, oral, etc. Applicants have discovered that a statistically significant ($p<0.003$) reduction in intracellular oxidation of approximately 50 percent was noted in human keratinocytes exposed to Applicants' metabolized conditioned growth medium.

Thus, in addition to inducing epidermal and dermal cell proliferation and collagen secretion in vitro the metabolized conditioned growth media and/or metabolized cell extract of the disclosure has antioxidant activity. See Example 18.

This sterile enriched nutrient solution represents a bioengineered cosmeceutical that is readily available in large volumes and may be useful as an additive for a variety of skin, cosmetic, and dermatologic products to supplement the levels of growth factors and matrix molecules in human skin, hair, and nails. Products are envisioned to use with Alpha Hydroxy Acids exfoliates to potentially optimize penetration of the growth factors and other biomolecules into the skin and with chemical peels to potentially accelerate healing and reduce inflammation.

The metabolized conditioned growth media and/or metabolized cell extract of the disclosure may be formulated for eliminating wrinkles, frown lines, scarring and other skin conditions instead of using silicone or other products to do so. The metabolized conditioned growth media and/or metabolized cell extract contains an activity of growth factors and inflammatory mediators such as, for example, VEGF, HGF, IL-6, IL-8, G-CSF and TFGβ, as well as extracellular matrix proteins such as type I and type III collagens, fibronectin, tenascin, glycosaminologycans, acid and basic FGF, TGF-α and TGF-β, KGF, versican, decorin betaglycens, syndean and various other secreted human dermal matrix proteins which are useful in repairing physical anomalies and cosmetic defects.

The metabolized conditioned growth media and/or metabolized cell extract of the disclosure can be formulated into injectable preparations. Alternatively, products derived from the conditioned media can be formulated. For example, biologically active substances, such as proteins and drugs, can be incorporated in the compositions of the present disclosure for release or controlled release of these active substances after injection of the composition. Exemplary biologically active substances can include tissue growth factors, such as TGF-β, and the like which promote healing and tissue repair at the site of the injection. Methods of product purification include, but are not limited to gel chromatography using matrices such as SEPHADEX®, ion exchange, metal chelate affinity chromatography, with an insoluble matrix such as cross-linked agarose, HPLC purification, hydrophobic interaction chromatography of the conditioned media. Such techniques are described in greater detail in *Cell & Tissue Culture; Laboratory Procedures*, supra; Sanbrook et al., 1989, *Molecular Cloning: A Laboratory Manual*, $2^{nd}$ Ed., Cold Spring Harbor Lab Press, Cold Spring Harbor, N.Y.

In the injectable embodiment, an aqueous suspension is used and the formulation of the aqueous suspension may have a physiological pH (i.e., about pH 6.8 to 7.5). Additionally, a local anesthetic, such as lidocaine, (usually at a concentration of about 0.3% by weight) is usually added to reduce local pain upon injection. The final formulation may also contain a fluid lubricant, such as maltose, which must be tolerated by the body. Exemplary lubricant components include glycerol, glycogen, maltose and the like. Organic polymer base materials, such as polyethylene glycol and hyaluronic acid as well as non-fibrillar collagen, preferably succinylated collagen, can also act as lubricants. Such lubricants are generally used to improve the injectability, intrudability and dispersion of the injected biomaterial at the site of injection and to decrease the amount of spiking by modifying the viscosity of the compositions. The final formulation is by definition the processed metabolized conditioned growth cell media in a pharmaceutically acceptable carrier.

The processed metabolized conditioned growth media and/or metabolized cell extract of the disclosure is subsequently placed in a syringe or other injection apparatus for precise placement of the metabolized conditioned growth media and/or metabolized cell extract of the disclosure at the site of the tissue defect. In the case of formulations for dermal augmentation, the term "injectable" means the formulation can be dispensed from syringes having a gauge as low as 25 under normal conditions under normal pressure without substantial spiking. Spiking can cause the composition to ooze from the syringe rather than be injected into the tissue. For this precise placement, needles as fine as 27 gauges (200 μI.D.) or even 30 gauges (150 μI.D.) are desirable. The maximum particle size that can be extruded through such needles will be a complex function of at least the following: particle maximum dimension, particle aspect ratio (length:width), particle rigidity, surface roughness of particles and related factors affecting particle:particle adhesion, the viscoelastic properties of the suspending fluid, and the rate of flow through the needle. Rigid spherical beads suspended in a Newtonian fluid represent the simplest case, while fibrous or branched particles in a viscoelastic fluid are likely to be more complex.

The above described steps in the process for preparing injectable secreted metabolized conditioned growth media and/or metabolized cell extract of the disclosure are preferably carried out under sterile conditions using sterile materials. The processed metabolized conditioned growth media and/or metabolized cell extract of the disclosure in a pharmaceutically acceptable carrier can be injected intradermally or subcutaneously to augment soft tissue, to repair or correct congenital anomalies, acquired defects or cosmetic defects. Examples of such conditions are congenital anomalies as hemifacial microsomia, malar and zygomatic hypoplasia, unilateral mammary hypoplasia, pectus excavatum, pectoralis agenesis (Poland's anomaly) and velopharyngeal incompetence secondary to cleft palate repair or submucous cleft palate (as a retropharyngeal implant); acquired defects (post-traumatic, post-surgical, post-infectious) such as depressed scars, subcutaneous atrophy (e.g., secondary to discoid lupis erythematosus), keratotic lesions, enophthalmos in the unucleated eye (also superior sulcus syndrome), acne pitting of the face, linear scleroderma with subcutaneous atrophy, saddle-nose deformity, Romberg's disease and unilateral vocal cord paralysis; and cosmetic defects such as glabellar frown lines, deep nasolabial creases, circum-oral geographical wrinkles, sunken cheeks and mammary hypoplasia. The compositions of the present disclosure can also be injected into internal tissues, such as the tissues defining body sphincters to augment such tissues.

Other tissue types used to condition the media include but are not limited to bone marrow, skin, epithelial cells, and cartilage, however, it is expressly understood that the three-dimensional culture system can be used with other types of cells and tissues.

Alternatively, the metabolized conditioned growth media and/or metabolized cell extract of the disclosure may be formulated with polymerizable or cross-linking hydrogels as described in the previous section on wound treatment.

D. Pharmaceutical Applications

The metabolized conditioned growth media and/or metabolized cell extract of the disclosure contain a variety of useful pharmaceutical factors and components such as growth factors, regulatory factors, peptide hormones, antibodies, etc., as described throughout the specification and are therefore useful for a variety of pharmaceutical applications. Also, products which may be added include, but are not limited to, antibiotics, antivirals, antifungals, steroids, analgesics, antitumor drugs, investigational drugs or any compounds which would result in a complimentary or synergistic combination with the factors in the conditioned media. As previously discussed, the cells are cultured, and the media recovered under aseptic conditions. Additionally, the media can be tested for pathogens. If sterilization is done, it must be done in a manner which minimally affects the desired biological activity as described, supra. The medium may be further processed to concentrate or reduce one or more factor or component contained within the medium, for example, enrichment of a growth factor using immunoaffinity chromatography or, conversely, removal of a less desirable component, for any given application as described therein. In a preferred embodiment, formulations are made from medium conditioned by a three-dimensional cell construct. The three-dimensional cultures produce a multitude of growth factors and proteins that are secreted into the medium at optimal physiological ratios and concentrations. See for example, Table 2. The medium, therefore, provides a unique combination of factors and specified ratios that closely represent those found in vivo. Bovine serum is generally not preferred in this application. It may be preferable to remove cellular debris or other particular matter as well as proteases, lactic acid and other components possibly detrimental to cell growth.

Assays commonly employed by those of skill in the art may be utilized to test the activity of the particular factor or factors, thereby ensuring that an acceptable level of biological activity (e.g., a therapeutically effective activity) is retained by the attached molecule or encapsulated molecule.

Thus, the metabolized conditioned growth media and/or metabolized cell extract of the disclosure and products derived from the media may be used, for example, to provide insulin in the treatment of diabetes, nerve growth factor for the treatment of Alzheimer's disease, factor VIII and other clotting factors for the treatment of hemophilia, dopamine for the treatment of Parkinson's disease, enkaphalins via adrenal chromaffin cells for the treatment of chronic pain, dystrophin for the treatment of muscular dystrophy, and human growth hormone for the treatment of abnormal growth.

Doses of such therapeutic protein agents are well known to those of skill in the art and may be found in pharmaceutical compedia such as the PHYSICIANS DESK REFERENCE, Medical Economics Data Publishers; REMINGTON'S PHARMACEUTICAL SCIENCES, Mack Publishing Co.; GOODMAN & GILMAN, THE PHARMACOLOGICAL BASIS OF THERAPEUTICS, McGraw Hill Publ., THE CHEMOTHERAPY SOURCE BOOK, Williams and Wilkens Publishers.

The therapeutically effective doses of any of the drugs or agents described above may routinely be determined using techniques well known to those of skill in the art. A "therapeutically effective" dose refers to that amount of the compound sufficient to result in amelioration of at least one symptom of the processes and/or diseases being treated.

Toxicity and therapeutic efficacy of the drugs can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the disclosure, the therapeutically effective dose can be estimated initially from cell culture assays. A circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Additionally, the cells and tissues may be genetically engineered to enhance expression of a desired product such as insulin, for example, and/or to express nucleotide sequences and/or moieties which target the gene products listed above e.g. ribozyme, antisense molecules and triple helices, which may have an inhibitory effect on target gene expression and/or activity. This might be advantageous when culturing tissues in which specialized stromal cells in the medium may play particular structural/functional roles, e.g., glial cells of neurological tissue, Kupffer cells of liver, etc.

E. Stimulation of Hair Growth

The medium may be conditioned using, for example, human hair papilla cells. Preferably, the medium conditioned by such cells is grown in three-dimensions. Hair papilla cells are a type of mesenchymal stem cell that plays a pivotal role in hair formation, growth and restoration (Matsuzaki et al., *Wound Repair Regen,* 6:524-530 (1998)). The subsequently metabolized conditioned growth medium is preferably concentrated and applied as a topical formulation. The metabolized conditioned media compositions may be formulated for topical applications using an agent that facilitates penetration of the compound into the skin, for example, DMSO, and applied as a topical application for stimulating hair growth.

The compositions of the disclosure promote or restore hair growth when applied topically by providing factors that increase epithelial cell migration to hair follicles. In addition to the factors found in the metabolized conditioned media, other compounds, such as minoxidil and antibiotics can be used. During hair growth there is a reduction in blood supply during catagen (the transitional phase of the hair follicle between growth and resting phases) and telogen (the resting phase). Biologically active molecules derived from the metabolized conditioned cell medium can be determined and optimized for use during these phases of hair growth using assays known in the art including the stump-tailed macaque model for male-patterned baldness, see for example, Brigham, Pa., A. Cappas, and H. Uno, The Stumptailed Macaque as a Model for Androgenetic Alopecia: Effects of Topical Minoxidil Analyzed by Use of the Folliculogram, *Clin Dermatol,* 1988, 6(4): p. 177-87; Diani, A. R. and C. J. Mills, Immunocytochemical Localization of Androgen Receptors in the Scalp of the Stumptail Macaque Monkey, a Model of Androgenetic Alopecia, *J Invest Dermatol,* 1994, 102(4): p. 511-4; Holland, J. M., Animal Models of Alopecia, *Clin Dermatol,* 1988, 6(4): p. 159-162; Pan, H. J., et al., Evaluation of RU58841 as an Anti-Androgen in Prostate PC3 Cells and a Topical Anti-Alopecia Agent in the Bald Scalp of Stumptailed Macaques, *Endocrine,* 1998, 9(1): p. 39-43; Rittmaster, R. S., et al., The Effects of N,N-diethyl-4-methyl-3-oxo-4-aza-5 alpha-androstane-17 beta-carboxamide, a 5 alpha-reductase Inhibitor and Antiandrogen, on the Development of Baldness in the Stumptail Macaque, *J. Clin Endocrinol Metab,* 1987, 65(1): p. 188-93 (each of which is incorporated by reference in its entirety). Additional models include measuring differences in hair follicle proliferation from follicles cultured from bald and hairy areas, a newborn rat model as well as a rat model of alopecia greata, see, Neste, D. V., The Growth of Human hair in Nude Mice, *Dermatol Clin.,* 1996, 14(4): p. 609-17; McElwee, K. J., E. M. Spiers, and R. F. Oliver, In Vivo Depletion of CD8+T Cells Restores Hair Growth in the DEBR Model for Alopecia Areata, *Br J Dermatol,* 1996, 135(2): p. 211-7; Hussein, A. M., Protection Against Cytosine Arabinowide-Induced Alopecia by Minoxidil in a Rat Animal Model, *Int J Dermatol,* 1995, 34(7): p. 470-3; Oliver, R. F., et al., The DEBR Rat Model for Alopecia Areata, *J Invest Dermatol,* 1991, 96(5): p. 978; Michie, H. J., et al., Immunobiological Studies on the Alopecic (DEBER) Rat, *Br J Dermatol,* 1990, 123(5): p. 557-67 (each of which is incorporated by reference in its entirety).

V. Other Uses

A. Food Additives and Dietary Supplements

The metabolized conditioned growth media and/or metabolized cell extract of the disclosure may be used as food additives and formulated into dietary supplements. The metabolized conditioned growth media and/or metabolized cell extract of the disclosure may contain many useful nutrients including essential amino acids, minerals, and vitamins in an abundance and variety not found in individual foods or good groups. The metabolized conditioned growth media and/or metabolized cell extract of the disclosure can be used as an inexpensive source for a balanced nutritional supplement for weight loss or alternatively for enhancing the nutritional content of food, particularly for third world countries. The metabolized conditioned growth media and/or metabolized cell extract of the disclosure is sterile and is free from contamination by human pathogens (i.e., aseptic). The metabolized conditioned growth media and/or metabolized cell extract of the disclosure may be concentrated and/or lyophilized and preferably administered in capsules or tablets for ingestion. Alternatively, the compositions may be directly added to adult or baby food to enhance nutritional content. This rich source of nutrients may be processed relatively inexpensively and can be invaluable to undernourished elderly people, and in particular, to children in under-developed countries where increased mortality due to poor responses to infection have been associated with malnutrition.

Additionally, many trace elements, such as iron and magnesium, are critical for mammalian survival and reproduction, and there is concern that marginal trace element deficiency may be a public health problem. The intake of various essential micronutrients has been suggested to decrease infection as well as cancer risk by modifying specific phases of carcinogenesis. Micronutrients also enhance the functional activities of the immune system and its interacting mechanism of T cells and B cells, Mos, and NK cells specifically by enhancing the production of various cytokines to facilitate their phagocytic and cytotoxic action against invading pathogens and/or to destroy emerging premalignant cells in various vital organs. See, Chandra, R. K. ed. (1988), *Nutrition and Immunology. Contemporary Issues in Clinical Nutrition,* Alan R. Liss, New York. Thus, there is a need for a relatively inexpensive source of balanced nutrients. Ideal food products for enrichment with the conditioned media are breads, cereals and other grain products such as pastas, crackers, etc. Also, the metabolized medium may be further processed to concentrate or reduce one or more factor or component contained within the medium, for example, enrichment of a growth factor using immunoaffinity chromatography or, conversely, removal of a less desirable component, for any given application as described in this section.

B. Animal Feed Supplement

The metabolized conditioned growth media and/or metabolized cell extract of the disclosure may be used as a supplemental to animal feed. In one embodiment, the metabolized conditioned growth media and/or metabolized cell extract of the disclosure contains bovine serum that provides a source of protein and other factors that are beneficial for mammals such as cattle and other ruminant animals, such as cows, deer and the like. The medium is screened for pathogens and is free of bovine pathogens and mycoplasma. The metabolized conditioned growth media and/or metabolized cell extract of the disclosure is preferably obtained from cows raised in the United States so that the likelihood of pathogens is markedly diminished.

In one embodiment, provided are compositions comprising a metabolized conditioned growth medium and an acceptable carrier, wherein the metabolized conditioned growth medium is conditioned growth medium metabolized by yeast cells. In some embodiments, the conditioned growth medium is prepared by culturing cells in a growth medium sufficient to meet the nutritional needs required to grow the cells in vitro to form a conditioned growth medium. In some embodiments, the composition is an injectable composition or a topical composition. In some embodiments, the topical composition is an ointment, a cream, a hydrogel, or a lotion. In other embodiments, the composition is used to treat or prevent a cosmetic defect, a congenital defect, hair loss or an acquired defect. In other embodiments, the cosmetic defect is a glabellar frown line, deep nasolabial crease, circum-oral geographical wrinkle, sunken cheeks or mammary hypoplasia. In some embodiments, the acquired defect is a medical condition that occurs post-trauma, post-surgery, post-infection or post-medical procedure defect.

In other embodiments, provided are compositions comprising a metabolized cell extract and an acceptable carrier, wherein the metabolized cell extract is cell extract metabolized by yeast cells. In some embodiments, the cell extract is derived from fibroblasts. In other embodiments, the composition is an injectable composition or a topical composition. In yet other embodiments, the topical composition is an ointment, a cream, a hydrogel, or a lotion. In still other embodiments, the composition is used to treat or prevent a cosmetic defect, a congenital defect, hair loss or an acquired defect. In some embodiments, the cosmetic defect is a glabellar frown line, deep nasolabial crease, circum-oral geographical wrinkle, sunken cheeks or mammary hypoplasia. In yet other embodiments, the acquired defect is a medical condition that occurs post-trauma, post-surgery, post-infection or post-medical procedure defect.

In still other embodiments, provide are metabolized conditioned growth medium prepared by a process comprising:

(a) culturing cells in a growth medium sufficient to meet the nutritional needs required to grow the cells in vitro to form a conditioned growth medium and removing the conditioned growth medium from the cultured cells;

(b) culturing yeast cells;

(c) exposing the yeast cells to the conditioned growth medium;

(d) culturing the yeast cells to metabolize at least a portion of the conditioned growth medium; and (e) collecting the metabolized conditioned growth medium.

In some embodiments, the yeast is *Pichia pastoris*. In other embodiments, the cells in step (a) are fibroblasts. In yet other embodiments, the process further comprises (e) processing the metabolized conditioned growth medium, wherein processing is concentrating, filtering, purifying, or a combination thereof.

In yet other embodiments, provided are processes for preparing the metabolized conditioned growth medium of any one of claims 15 to 18, comprising:

(a) culturing cells in a growth medium sufficient to meet the nutritional needs required to grow the cells in vitro to form a conditioned growth medium and removing the conditioned growth medium from the cultured cells;

(b) culturing yeast cells;

(c) exposing the yeast cells to the conditioned growth medium;

(d) culturing the yeast cells to metabolize at least a portion of the conditioned growth medium; and (e) collecting the metabolized conditioned growth medium.

In some embodiments, the metabolized conditioned growth medium is combined with an acceptable carrier. In yet other embodiments, the metabolized conditioned growth medium is present in an amount of about 0.0001% to about 95% by weight of the composition, about 0.01% to about 50% by weight of composition or about 0.01% to about 10% by weight of composition. In still other embodiments, the composition further comprises at least one of water, surfactants, emulsifiers, conditioners, emollients, waxes, oils, polymers, thickeners, fixatives, colorants, nutraceuticals, cosmeceuticals, therapeutics, pharmaceuticals, antifungals, antimicrobials, steroidal hormones, antidandruff agents, anti-acne components, sunscreens, and preservatives. In still other embodiments, the composition is an injectable composition or a topical composition. In some embodiments, the topical composition is an ointment, a cream, a hydrogel, or a lotion.

Also provided herein are metabolized cell extract prepared by a process comprising:

(a) providing a cell extract;

(b) culturing yeast cells;

(c) exposing the yeast cells to the cell extract;

(d) culturing the yeast cells to metabolize at least a portion of the cell extract; and (e) collecting the metabolized cell extract.

In some embodiments, the yeast is *Pichia pastoris*. In other embodiments, the cell extract is derived from fibroblasts. In some embodiments, the process further comprises (e) processing the metabolized cell extract, wherein processing is concentrating, filtering, purifying, or a combination thereof.

In one embodiment, provided are compositions comprising: an acceptable carrier and a metabolized conditioned growth medium prepared by a process comprising:

(a) culturing cells in a growth medium sufficient to meet the nutritional needs required to grow the cells in vitro to form a conditioned growth medium and removing the conditioned growth medium from the cultured cells;

(b) culturing yeast cells;

(c) exposing the yeast cells to the conditioned growth medium;

(d) culturing the yeast cells to metabolize at least a portion of the conditioned growth medium; and (e) collecting the metabolized conditioned growth medium.

In some embodiments, the yeast is *Pichia pastoris*. In other embodiments, the cells in step (a) are fibroblasts. In some embodiments, the composition further comprises (e) processing the metabolized conditioned growth medium, wherein processing is concentrating, filtering, purifying, or a combination thereof. In some embodiments, the metabolized conditioned growth medium is present in an amount of about 0.0001% to about 95% by weight of the composition, about 0.01% to about 50% by weight of the composition, or about 0.01% to about 10% by weight of the composition. In other embodiments, the composition further comprises at least one of water, surfactants, emulsifiers, conditioners, emollients, waxes, oils, polymers, thickeners, fixatives, colorants, nutraceuticals, cosmeceuticals, therapeutics, pharmaceuticals, antifungals, antimicrobials, steroidal hormones, antidandruff agents, anti-acne components, sunscreens, and preservatives. In some embodiments, the composition is an injectable composition or a topical composition. In yet other embodiments, the topical composition is an ointment, a cream, a hydrogel, or a lotion.

Also provided herein are compositions comprising: an acceptable carrier and a metabolized cell extract prepared by a process comprising:
 (a) providing a cell extract;
 (b) culturing yeast cells;
 (c) exposing the yeast cells to the cell extract;
 (d) culturing the yeast cells to metabolize at least a portion of the cell extract; and
 (e) collecting the metabolized cell extract.

In one embodiment, the yeast is *Pichia pastoris*. In some embodiments, the cell extract is derived from fibroblasts. In other embodiments, the process further comprises (e) processing the metabolized cell extract, wherein processing is concentrating, filtering, purifying, or a combination thereof. In some embodiments, the metabolized conditioned growth medium is present in an amount of about 0.0001% to about 95% by weight of the composition, about 0.01% to about 50% by weight of the composition, or about 0.01% to about 10% by weight of the composition. In some embodiments, the composition further comprises at least one of water, surfactants, emulsifiers, conditioners, emollients, waxes, oils, polymers, thickeners, fixatives, colorants, nutraceuticals, cosmeceuticals, therapeutics, pharmaceuticals, antifungals, antimicrobials, steroidal hormones, antidandruff agents, anti-acne components, sunscreens, and preservatives. In other embodiments, the composition is an injectable composition or a topical composition. In still other embodiments, the topical composition is an ointment, a cream, a hydrogel, or a lotion.

Also provided herein are methods for preventing or treating a condition in a subject comprising administering to the subject a therapeutically effective amount of a composition comprising: an acceptable carrier and a metabolized conditioned growth medium prepared by a process comprising:
 (a) culturing cells in a growth medium sufficient to meet the nutritional needs required to grow the cells in vitro to form a conditioned growth medium and removing the conditioned growth medium from the cultured cells;
 (b) culturing yeast cells;
 (c) exposing the yeast cells to the conditioned growth medium;
 (d) culturing the yeast cells to metabolize at least a portion of the conditioned growth medium; and
 (e) collecting the metabolized conditioned growth medium.

In one embodiment, the condition is a cosmetic defect, hair loss, a congenital defect or an acquired defect. In other embodiments, the acquired defect is a medical condition that occurs post-trauma, post-surgery, post-infection or a post-medical procedure defect. In yet other embodiments, the cosmetic defect is a glabellar frown line, deep nasolabial crease, circum-oral geographical wrinkle, sunken cheeks or mammary hypoplasia. In still other embodiments, the yeast is *Pichia pastoris*. In some embodiments, the cells in step (a) are fibroblasts. In other embodiments, the process further comprises (e) processing the metabolized conditioned growth medium, wherein processing is concentrating, filtering, purifying, or a combination thereof. In some embodiments, the metabolized conditioned growth medium is present in the composition in an amount of about 0.0001% to about 95% by weight of the composition, about 0.01% to about 50% by weight of the composition, or about 0.01% to about 10% by weight of the composition. In one non-limiting example, the metabolized conditioned growth medium is present in the composition in an amount of about 10%, about 15%, or about 20% by weight of the composition. In still other embodiments, the composition further comprises at least one of water, surfactants, emulsifiers, conditioners, emollients, waxes, oils, polymers, thickeners, fixatives, colorants, nutraceuticals, cosmeceuticals, therapeutics, pharmaceuticals, antifungals, antimicrobials, steroidal hormones, antidandruff agents, anti-acne components, sunscreens, and preservatives. In yet other embodiments, the composition is an injectable composition or a topical composition. In other embodiments, the topical composition is an ointment, a cream, a hydrogel, or a lotion. In still other embodiments, at least one extracellular matrix protein is up-regulated by the administration of the composition to the subject. In one embodiment, the extracellular matrix protein is up-regulated by about 5% to about 100%, by about 10% to about 50%, or by about 60% to about 100%. In another embodiment, the extracellular matrix protein is a collagen protein or a lysyl hydroxylase protein. In still another embodiment, the extracellular matrix protein is encoded by COL4A1 gene or PLOD1 gene. In one embodiment, at least one repair protein is up-regulated by the administration of the composition to the subject. In another embodiment, the repair protein is up-regulated by about 10% to about 70%, by about 35% to about 50%, or by about 25% to about 50%. In another embodiment, the repair protein is a fibronectin protein. In another embodiment, the repair protein is encoded by FN1 gene. In still another embodiment, at least one cellular connectivity protein is up-regulated by the administration of the composition to the subject. In some embodiments, the cellular connectivity protein is up-regulated by about 5% to about 200%, by about 10% to about 80%, or by about 30% to about 50%. In some embodiments, the cellular connectivity protein is involucrin protein. In still other embodiments, the cellular connectivity protein is encoded by IVL gene. In one embodiment, at least one antioxidant protein is up-regulated by the administration of the composition to the subject. In another embodiment, the antioxidant protein is up-regulated by about 5% to about 300%, by about 10% to about 50%, or by about 200% to about 250%. In another embodiment, the antioxidant protein is a superoxide dismutase protein. In still other embodiments, the antioxidant protein is encoded by SOD2 gene.

Also provided herein are methods for preventing or treating a condition in a subject comprising administering to the subject a therapeutically effective amount of a composition comprising: an acceptable carrier and a metabolized cell extract prepared by a process comprising:
 (a) providing a cell extract;
 (b) culturing yeast cells;
 (c) exposing the yeast cells to the cell extract;
 (d) culturing the yeast cells to metabolize at least a portion of the cell extract; and
 (e) collecting the metabolized cell extract.

In some embodiments, the condition is a cosmetic defect, hair loss, a congenital defect or an acquired defect. In some embodiments, the acquired defect is a medical condition that occurs post-trauma, post-surgery, post-infection, or post-medical procedure defect. In other embodiments, the cosmetic defect is a glabellar frown line, deep nasolabial crease, circum-oral geographical wrinkle, sunken cheeks or mammary hypoplasia. In one embodiment, the yeast is *Pichia*

*pastoris*. In another embodiment, the cell extract is derived from fibroblasts. In still another embodiment, the process further comprises (e) processing the metabolized cell extract, wherein processing is concentrating, filtering, purifying, or a combination thereof. In still other embodiments, the metabolized conditioned growth medium is present in the composition in an amount of about 0.0001% to about 95% by weight of the composition, by about 0.01% to about 50% by weight of the composition, or by about 0.01% to about 10% by weight of the composition. In one non-limiting example, the metabolized cell extract is present in the composition in an amount of about 10%, about 15%, or about 20% by weight of the composition. In still other embodiments, the composition further comprises at least one of water, surfactants, emulsifiers, conditioners, emollients, waxes, oils, polymers, thickeners, fixatives, colorants, nutraceuticals, cosmeceuticals, therapeutics, pharmaceuticals, antifungals, antimicrobials, steroidal hormones, antidandruff agents, anti-acne components, sunscreens, and preservatives. In one embodiment, the composition is an injectable composition or a topical composition. In another embodiment, the topical composition is an ointment, a cream, a hydrogel, or a lotion. In one embodiment, at least one extracellular matrix protein is up-regulated by the administration of the composition to the subject. In another embodiment, the extracellular matrix protein is up-regulated by about 5% to about 100%, by about 10% to about 50%, or by about 60% to about 100%. In yet another embodiment, the extracellular matrix protein is a collagen protein or a lysyl hydroxylase protein. In some embodiments, the extracellular matrix protein is encoded by COL4A1 gene or PLOD1 gene. In some embodiments, at least one repair protein is up-regulated by the administration of the composition to the subject. In one embodiment, the repair protein is up-regulated by about 10% to about 70%, or by about 25% to about 50%. In another embodiment, the repair protein is a fibronectin protein. In still another embodiment, the repair protein is encoded by FN1 gene. In one embodiment, at least one cellular connectivity protein is up-regulated by the administration of the composition to the subject. In another embodiment, the cellular connectivity protein is up-regulated by about 5% to about 200%, by about 10% to about 80%, or by about 30% to about 50%. In still another embodiment, the cellular connectivity protein is involucrin protein. In still another embodiment, the cellular connectivity protein is encoded by IVL gene. In one embodiment, at least one antioxidant protein is up-regulated by the administration of the composition to the subject. In another embodiment, the antioxidant protein is up-regulated by about 5% to about 300%, by about 10% to about 50%, or by about 200% to about 250%. In another embodiment, the antioxidant protein is a superoxide dismutase protein. In yet another embodiment, the antioxidant protein is encoded by SOD2 gene.

EXAMPLES

Example 1: Fibroblast Monolayer Cell Culture

Normal human dermal fibroblasts, isolated from a human foreskin, were cultured in a 150 cm$^2$ tissue culture flasks (Corning, Corning, N.Y.) in monolayer culture using pre-conditioned cell culture media (in this example, high-glucose Dulbecco's Modified Eagle's Media (DMEM; Gibco-BRL, Grand Island, N.Y.) supplemented with 10% bovine calf serum (Hyclone Laboratories, Logan, Utah), nonessential amino acids (GibcoBRL), and 100 U/ml penicillin-streptomycin-250 ng/ml amphoterecin B (GibcoBRL) ("DMEM 1") in a 37° C., 5% $CO_2$ incubator. Monolayer cultures were fed twice weekly with fresh pre-conditioned media and passaged weekly using a 1 to 10 split, as described. See generally, Pinney et al., *J. Cell. Physio.*, 183:74 82 (2000). The dermal fibroblasts may also be expanded in roller bottles with DMEM 1. The conditioned media from these monolayer cultures is collected and saved for future use.

While fibroblast cells have been used for illustrative purposes in this example, the skilled artisan will understand that many other types of cells, for example, but not limited to, other epithelial cell types, endothelial cells, smooth muscle cells, myocytes, keratinocytes, chondrocytes, and the like, may be grown in monolayer culture and in three-dimensional culture.

Example 2: Conditioning the Medium

Human dermal fibroblasts were seeded onto the substrate of the apparatus described in the '766 patent and described in detail above. The substrate is within the casing designed to facilitate three-dimensional tissue growth on its surface and the cells were cultured in a closed system in cultured in high glucose DMEM (10% BCS supplemented with 2 mM L-glutamine and 50 mg/ml ascorbic acid) at 37° C. in a humidified, 5% $CO_2$ atmosphere. After 10 days the cell culture was removed, fresh medium was added. The cells were cultured for an additional 4 days as described above. The resulting conditioned medium, having been exposed to the cell and tissue culture for four days (days 10-14) was then removed from the individual chambers and pooled. The conditioned medium (approximately 5 to 10 liters/pool) was dispensed into 200 ml aliquots and further concentrated 10- to 20-fold using a positive pressure concentration device having a filter with a 10,000 MW cut-off (Amicon, Beverly, Mass.). The resulting 10 to 20 ml of concentrated conditioned medium was dispensed into 1 ml aliquots and frozen at −20° C. for analysis. A 1× concentration of conditioned medium results from 10× conditioned medium added to base medium as a 10% (vol/vol) solution. Likewise, a 1× concentration of "medium" or "serum free medium" results from 10× medium (i.e., base medium) or 10× serum free medium (base medium without serum) added to base medium as a 10% (vol/vol) solution which are then used as controls.

Example 3: Preparation of Metabolized Conditioned Growth Media a. Organism and Media

*Pichia pastoris* (wild-type strain) was used as the yeast cell culture for fermentation work. Stock cultures were maintained on yeast-peptone-dextrose (YPD) agar plates. The parent stock culture was grown in YPD broth and maintained at −20° C. The fermentation was carried out in Yeast Nitrogen-Base (YNB) growth media and supplemented with glycerol containing, 2.7% $H_3PO_4$, 0.09% $CaSO_4$, 1.8% $K_2SO_4$, 1.5% $MgSO_4$, 0.41% KOH, 4% glycerol (Sigma St. Louis, Mo.). Condition Growth Media was supplied by SkinMedica (California).

b. Fermentor

The fermentation process was scaled up to 2L and 15L fermentation stages (2L New Brunswick Scientific, Edison N.J. and 15L Applikon Biotechnology Foster City Calif.) using standard growing conditions for the yeast.

c. Conditioned Growth Media Metabolization Conditions

Fed-batch cultures were grown at 29° C., in Yeast Nitrogen-Base (YNB) growth media and supplemented with glycerol (2.7% $H_3PO_4$, 0.09% $CaSO_4$, 1.8% $K_2SO_4$, 1.5% $MgSO_4$, 0.41% KOH, 4% glycerol). The pH was kept constant at 5.0±0.5 by titration with 2M $NH_4OH$. The dissolved oxygen levels were measured by a sterilizable DO probe and the oxygen saturation was kept at 30% by regulating the stirring velocity between 100 and 600 rpm. Conditioned growth media was introduced to the fermentation process as a nutritional supplement by inoculating the liquid media into the fermentor during the active growth phase of the yeast. The fed-batch process was initiated during the logarithmic growth phase of *Pichia pastoris*. Growth was measured by monitoring optical density of *Pichia pastoris* during fermentation. The fermentation was carried out until such time that the conditioned growth media was metabolized by *Pichia pastoris*, as measured by the changes in the growth phase of *Pichia pastoris* from logarithmic phase to stationary phase. The fermentation may be carried out to completion wherein the conditioned growth media is fully metabolized, or may be partially fermented, i.e., partially metabolized.

The conditioned growth media may be concentrated, filtered and/or purified prior to combining the metabolized conditioned growth medium with a suitable vehicle.

Example 4: Preparation of Metabolized Cell Extract a. Cell Extract

Whole cell extract is obtained from animal cells or plant cells, for example, by any method known to the skilled artisan.

b. Organism and Media

*Pichia pastoris* (wild-type strain) is used as the yeast cell culture for fermentation work. Stock cultures are maintained on yeast-peptone-dextrose (YPD) agar plates. The parent stock culture is grown in YPD broth and maintained at −20° C. The fermentation is carried out in Yeast Nitrogen-Base (YNB) growth media and supplemented with glycerol containing, 2.7% $H_3PO_4$, 0.09% $CaSO_4$, 1.8% $K_2SO_4$, 1.5% $MgSO_4$, 0.41% KOH, 4% glycerol (Sigma St. Louis, Mo.).

b. Fermentor

The fermentation process is scaled up to 2L and 15L fermentation stages (2L New Brunswick Scientific, Edison N.J. and 15L Applikon Biotechnology Foster City Calif.) using standard growing conditions for the yeast.

c. Cell Extract Metabolization Conditions

Fed-batch cultures are grown at 29° C., in Yeast Nitrogen-Base (YNB) growth media and supplemented with glycerol (2.7% $H_3PO_4$, 0.09% $CaSO_4$, 1.8% $K_2SO_4$, 1.5% $MgSO_4$, 0.41% KOH, 4% glycerol). The pH is kept constant at 5.0±0.5 by titration with 2M $NH_4OH$. The dissolved oxygen levels are measured by a sterilizable DO probe and the oxygen saturation was kept at 30% by regulating the stirring velocity between 100 and 600 rpm. Cell extract is introduced to the fermentation process as a nutritional supplement by inoculating the liquid media into the fermentor during the active growth phase of the yeast. The fed-batch process is initiated during the logarithmic growth phase of *Pichia pastoris*. Growth is measured by monitoring optical density of *Pichia pastoris* during fermentation. The fermentation is carried out until such time that the cell extract is metabolized by *Pichia pastoris*, as measured by the changes in the growth phase of *Pichia pastoris* from logarithmic phase to stationary phase. The cell extract may be may be concentrated, filtered and/or purified prior to combining the metabolized cell extract with a suitable vehicle.

d. Proliferating Activity of Three-Dimensional-Conditioned Medium

The conditioned medium and metabolized conditioned growth medium and metabolized cell extract of Examples 2-4 may be optionally examined for the ability to promote the proliferation of human fibroblasts and keratinocytes. Human fibroblasts or human basal keratinocytes are seeded into 96 well plates (~5,000 cells/well) and cultured in high glucose DMEM (10% BCS supplemented with 2 mM L-glutamine and 1× antibiotic/antimycotic) supplemented with 1× final concentration of serum-free-medium, medium, or the three-dimensional conditioned medium, metabolized conditioned growth medium or metabolized cell extract as described above in Examples 2-4. The cultures are maintained at 37° C. in a humidified, 5% $CO_2$ atmosphere for 3 days.

Cellular proliferation is measured using a commercially available, fluorescent-based dye assay that measures total nucleic acid content as an estimation of cell proliferation (CyQuant Cell Proliferation Assay Kit, Molecular Probes, Eugene, Or). All assays are performed according to the manufacturer's instructions. Medium is removed by blotting and the cells are lysed using lysis buffer containing the green fluorescent dye, CyQuant GR dye. The dye exhibits strong fluorescence enhancement when bound to cellular nucleic acids and the amount of fluorescence is proportional to the amount of nucleic acid present in the sample. Samples are incubated for 5 minutes in the absence of light and sample fluorescence is determined using a microtiter plate reader with filters appropriate for ~480 nm excitation and ~520 nm emission maxima. The amount of nucleic acid in each sample is calculated by comparing the amount of observed fluorescence in each well against a standard curve, derived using known concentrations of calf thymus DNA as a standard.

Figure 3:
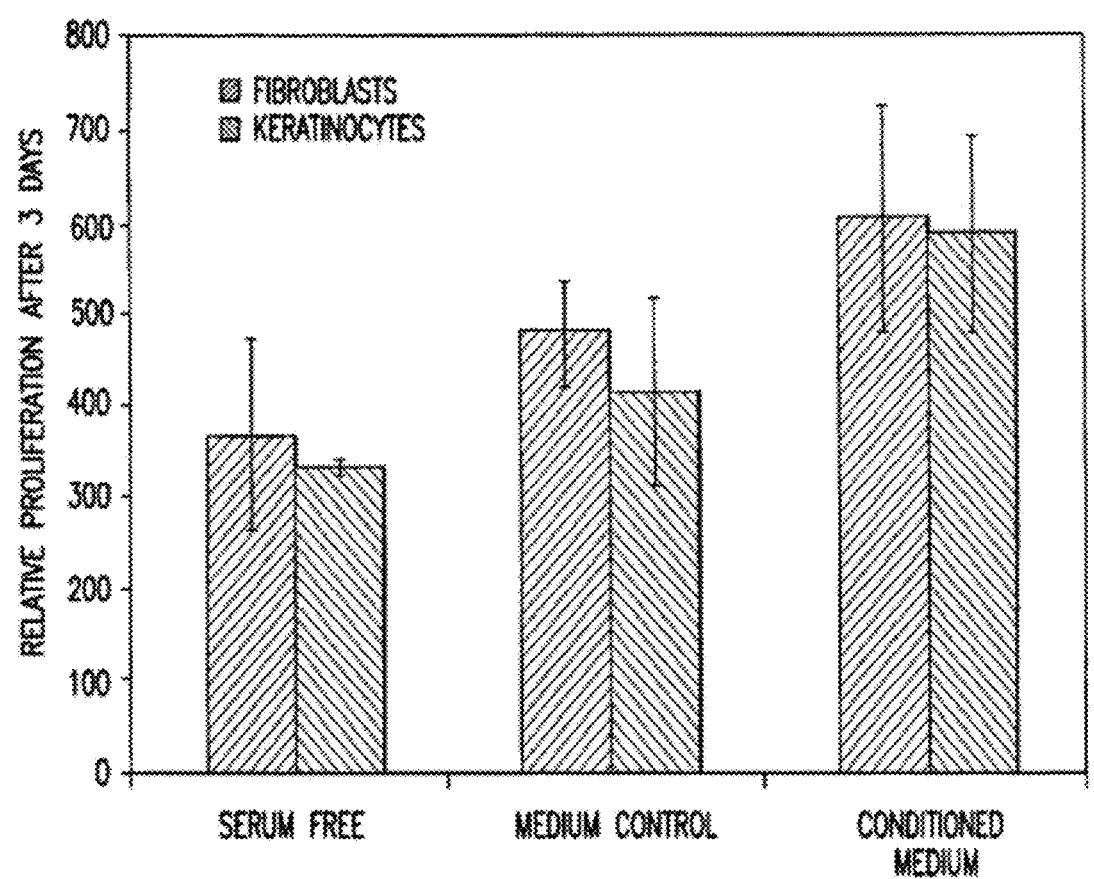
FIG. 3 is a graph representing relative proliferation of human fibroblasts and keratinocytes exposed to conditioned medium (cell culture medium which has previously supported the growth of cells in Transcyte™). An increase in cell response was revealed in as little as three days.

An exemplary result is shown in FIG. 3, where the cells cultured in the medium containing the conditioned medium resulted in increased cellular proliferation of both fibroblast and keratinocyte cells when compared to two controls.

Example 5: Modulation of Collagen Deposition into Tissues by Metabolized Conditioned Growth Medium a. Wound Healing Applications The effect of metabolized conditioned growth medium on the preparation and composition of three-dimensional tissues is examined by measuring the amount of collagen secreted into the extracellular matrix of tissues cultured in the presence of serum-free medium, medium or three dimensional conditioned medium.

Nylon scaffolds are laser-cut into 11 mm×11 mm squares, washed in 0.5M acetic acid, rinsed extensively in FBS, and seeded with 12F clinical fibroblasts at passage 8 (~38,000/cm$^2$). Cultures are grown in 1 ml of DMEM (10% BCS supplemented with 2 mM L-glutamine and 1× antibiotic/antimycotic) supplemented with 1× final concentration of serum-free-medium, medium, or the metabolized conditioned growth medium as described above in with the addition of 50 mg/ml ascorbate at each feeding. Copper sulfate is added to a final concentration of 2.5 ng/ml, and high oxygen (40%, about twice atmospheric) is maintained by regulated gassing of a standard incubator. Cultures (n=3 or greater) are maintained at 37° C. in a humidified, 5% $CO_2$ atmosphere for 10 days. A no ascorbate control is also included.

b. Collagen Isolation

Collagen is isolated and purified to near homogeneity from three-dimensional tissue cultures grown in the presence of base medium supplemented with a 1× final concentration of serum-free medium, medium or metabolized conditioned growth medium described above. The purity of the final samples preparations is estimated by subjecting the purified collagen samples to electrophoresis on gradient SDS-polyacrylamide gels, visualizing the separate protein bands using Coomassie blue, and estimating the amount of collagen-specific alpha-, beta- and gamma-bands compared to total protein (below). Purification methods should yield similar patterns in all samples.

Samples are rinsed in PBS, then sterile water, followed by 2-6 hours in 0.5M acetic acid. The samples are then digested overnight in 1 mg/ml pepsin (Worthington, Inc.) in 0.012N HCl at 4° C. Samples are clarified by centrifugation at 13000 rpm at 4° C. Collagen is precipitated 30-60 minutes at 4° C. after addition of 5 M NaCl to a final concentration of 0.7M. Precipitated collagen is separated by centrifugation at 13000 rpm at 4° C. for 30 to 60 minutes, and resuspended in 0.012N HCl.

c. Analysis

Total protein is determined using a commercially available colorimetric assay kit (Pierce, Inc. BCA assay kit) and assays are performed according to the manufacturer's instructions. Bovine skin collagens are used as a standard (InVitrogen, Carlsbad, Calif.; Cohesion Technologies, Inc., Palo Alto, Calif.) for quantifying total protein.

Samples (10 mg) are then subjected to SDS-PAGE analysis with electrophoresis on 3-8% gradient gels. The samples of isolated collagens are then heated to 95° C. in reducing sample buffer. Gels are stained with Coomassie Blue, destained, and computer-scanned for visualization.

Enhanced deposition of collagen in vivo has a number of applications, including wound healing, the treatment of wrinkles and contour lines that appear with increased age as well as being able to promote matrix deposition over bony-prominences susceptible to pressure ulcers in paralyzed or bedridden patients.

Example 6: Occlusive Patch Test Assessing the In Vivo Effects of Metabolized Conditioned Growth Medium a. Experimental Design:

Six consenting adult females (30-60 yr) in good health are enrolled. Exclusion criteria includes sensitivity to proteins, skin diseases, damaged skin in or near test sites, diabetes, renal, heart or immunological disorders, use of anti-inflammatory, immuno suppressive, antihistamine or topical drugs or cosmetics and pregnancy. Test articles are assigned to test sites (2 sites, 3.8 $cm^2$) on the right or left forearm of each subject according to a rotational scheme to minimize position or order bias. Site 1 is designated for vehicle control and site 2 treatment (i.e., metabolized conditioned growth medium). Occlusion patches are of a Webril nonwoven cotton pad with either 0.2 ml of vehicle or treatment. Patches are covered and held by a 3M occlusive, plastic, hypoallergenic tape. Occlusion patches are positioned daily on the forearms of 3 subjects for 5 consecutive, 24-hour periods. The remaining 3 subjects are patched daily for 12, consecutive 24-hour periods. On the day following the last patch application, a 2-mm biopsy is taken from each site. This protocol is approved by the IRB for the investigative organization, the California Skin Research Institute (San Diego, Calif.), and is in accordance with Title 21 of the CFR, Parts 50 and 56.

b. Evaluations:

Gross observations are graded for glazing, peeling, scabbing, fissuring, hyperpigmentation, and hypopigmentation. Irritation is scored visually using a 5 point scale and graded numerically for erythema, edema, papules and vesicles (>25% patch site), and identifiable reactions (<25% patch site), i.e., bulla reaction with or without weeping, spreading, and induration. The H & E histological assessment by a board certified pathologist includes parameters for viable epidermal thickness, epidermal hyperplasia (acanthosis), granular cell layer thickness, inflammatory infiltrate, mitotic figures, appearance of collagen and elastic fibers, and vasculature.

Example 7: Modulation of Human Endothelial Cell Behavior

The effects of metabolized conditioned growth medium on angiogenesis and endothelial cell motility are determined. Metabolized conditioned growth medium is either concentrated (10×) or lyophilized.

a. Endothelial Cell Tubule Formation Assay

Endothelial cell tubule formation assay with human umbilical vein endothelial cells (HUVEC) is used to assess angiogenesis.

b. Wounding Assay

A confluent layer of endothelial cells are scratched and the speed of closure of the resulting "wound" is measured used to assess cell motility. The "wounding" assay is measured as speed of closure in mm/h (millimeters/hour).

Example 8: Preparation of Yeast Extract a. Organism and Media

Yeast cell culture was obtained from ATCC (*Pichia pastoris* #60372). Stock cultures were maintained on yeast-peptone-dextrose (YPD) agar plates. The parent stock culture was grown in YPD broth and maintained at −20° C. The fermentation was carried out in Yeast Nitrogen-Base (YNB) growth media and supplemented with glycerol containing, 2.7% $H_3PO_4$, 0.09% $CaSO_4$, 1.8% $K_2SO_4$, 1.5% $MgSO_4$, 0.41% KOH, 4% glycerol (Sigma St. Louis, Mo.). Antifoam sigma-emulsion B was used throughout the process (Sigma, St. Louis, Mo.).

b. Fermentor

After optimization of treatment via the shake flask trials, the process was scaled up to 2L and 15L fermentation stages (2L New Brunswick Scientific, Edison N.J. and 15L Applikon Biotechnology Foster City Calif.).

c. Stress Conditions

Fed-batch cultures were grown at 29° C., in Yeast Nitrogen-Base (YNB) growth media and supplemented with glycerol (2.7% $H_3PO_4$, 0.09% $CaSO_4$, 1.8% $K_2SO_4$, 1.5% $MgSO_4$, 0.41% KOH, 4% glycerol). The pH was kept constant at 5.0±0.5 by titration with 2M $NH_4OH$. The dissolved oxygen levels were measured by a sterilizable DO probe and the oxygen saturation was kept at 30% by regulating the stirring velocity between 100 and 600 rpm. The aeration rate was set at IVVM.

Example 9: Full Thickness Evaluation

The metabolized cell extract disclosed above are tested on the MatTek full thickness skin tissue model. This skin model consists of: 1) normal human-derived epidermal keratinocytes that have been cultured to form a multilayered, highly differentiated model of the human epidermis and, 2) human fibroblasts that have been seeded into a collagen matrix to form the dermis. Upon arrival, the tissues are stored at 4° C. until used. For use, the tissues are removed from the agarose-shipping tray and placed into a 6-well plate containing 4 ml of assay medium and allowed to equilibrate overnight at 37±2° C. and 5±1% $CO_2$. After the overnight equilibration, the media is replaced with 4 ml of fresh media and 50 µl of test material (i.e. metabolized cell extract) is then applied topically to the tissues. The tissues are then incubated for 24 hours at 37+2° C. and 5+1% $CO_2$ and physiological effects of the treatment measured over time.

Example 10: Preparation of Liposomal Encapsulated Metabolized Conditioned Growth Medium Samples of metabolized conditioned growth medium are incorporated into liposome comprising phospholipid and lecithin layer obtained from soybeans. The lysate is slurried together with liposome using a high-pressure homogenizer obtained from Hydraulic Engineering Corporation (Brea, Calif.). The milky white mixture contains the metabolized conditioned growth medium encapsulated with the liposomal components.

Example 11: Preparation of Maltodextrin-Encapsulated Metabolized Cell Extract Samples of metabolized cell extract are encapsulated in maltodextrin and spray-dried to essentially provide an anhydrous powder of maltodextrin-encapsulated metabolized cell extract using the methodologies in WO2003/068161.

Example 12: Water-in-Oil Emulsion

The example illustrates a high internal phase water-in-oil emulsion incorporating the metabolized conditioned growth medium as disclosed above.

| Ingredient | Wt % |
|---|---|
| 1,3-dimethyl-2-imdazolidione | 0.2 |
| Polyoxylene (2) oleyl ether1 (Oleth-2) | 5.0 |
| Disteardimonium Hectorite | 0.5 |
| $MgSO_4 \cdot 7H_2O$ | 0.3 |
| Preservative | 0.01 |
| Metabolized conditioned growth medium | 10.0 |
| Water | To 100 |

Example 13: Water-in-Oil Cream

The example illustrates a water-in-oil cream incorporating the metabolized conditioned growth medium prepared as disclosed above.

| Ingredient | Wt % |
|---|---|
| Mineral oil | 4 |
| 1,3-dimethyl-2-imdazolidione | 1 |
| Ceteth-10 | 4 |
| Cetyl alcohol | 4 |
| Triethanolamine | 0.75 |
| Butylene glycol | 3 |
| Xanthum gum | 0.3 |
| Methyl, propyl and butyl paraben | 0.01 |
| Metabolized conditioned growth medium | 10 |
| Water | To 100 |

Example 14: Alcoholic Lotion

The example illustrates an alcoholic lotion incorporating the metabolized cell extract prepared as disclosed above.

| Ingredient | Wt % |
|---|---|
| 1,3-dimethyl-2-imdazolidione | 0.3 |
| Ethyl alcohol | 40.0 |
| Metabolized cell extract | 10.0 |
| Water | To 100 |

Example 15: Sub-Micron Emulsion Concentrate

The example illustrates a sub micron emulsion concentration that contains the metabolized conditioned growth medium prepared as disclosed above.

| Ingredient | Wt % |
|---|---|
| Trimethylopropane Tricaprylate/Tricaprate | 18.0 |
| Glycerin | 8.0 |
| Cetcaryl alcohol | 2.0 |
| Cetcareth 20 | 2.0 |
| Glyceral stearate | 2.0 |
| Butylated hydroxytoluene | 0.01 |
| Metabolized conditioned growth medium | 10 |
| Water | To 100 |

Example 16: Dilution of Metabolized Cell Extract

The example illustrates a dilution that contains the metabolized cell extract prepared as disclosed above

| Ingredient | Wt % |
|---|---|
| Water | 89 |
| Metabolized cell extract | 10 |
| Preservative | 1.0 |

Example 17: Human DNA Micro Array Studies on Normal Human Dermal Fibroblasts Normal human dermal fibroblasts were treated for 24-hour exposure as follows: (i) control 1: Nouricel (10×), i.e., conditioned growth medium (see, e.g., Example 2); (ii) control 2: *Pichia* ferment filtrate (20×), i.e., yeast ferment extract (see Example 8); (iii) partially fermented Nouricel (20×), i.e., partially metabolized conditioned growth medium (see Example 3); and (iv) fully fermented Nouricel (20×), i.e., fully metabolized conditioned growth medium (see Example 3).

The results are presented in the table below and are represented as a ratio of median between treated and untreated samples. A ratio of median >1.3 indicates strong up-regulation and < indicates strong down-regulation of the gene.

| Sample | (i) Nouricel | (ii) Pichia Ferment Filtrate | (iii) Partially fermented Nouricel | (iv) Fully fermented Nouricel |
|---|---|---|---|---|
| Gene Name | | | | |
| COL1A1 | 1.53 | 1.114 | 1.013 | 1.12 |
| COL1A2 | 1.608 | 1.994 | 1.371 | 1.806 |
| COL4A1 | 0.978 | 0.443 | 1.148 | 1.327 |
| ELN | 1.075 | 0.581 | 0.86 | 0.488 |
| FN1 | 1.248 | 1.573 | 0.706 | 1.35 |
| IVL | 0.675 | 0.316 | 0.256 | 0.5 |
| PLOD1 | 0.981 | 1.196 | 0.855 | 1.417 |
| TIMP1 | 1.874 | 1.852 | 1.397 | 1.967 |
| SOD1 | 1.184 | 1.396 | 1.215 | 0.965 |
| SOD2 | 1.293 | 2.373 | 2.543 | 2.739 |
| CAT | 0.902 | 0.294 | 0.678 | 0.48 |

Results from a second assay are presented in the table below and are as a ratio of median between treated and untreated samples. A ratio of median >1.3 indicates strong up-regulation and < indicates strong down-regulation of the gene.

| Sample | (i) Nouricel | (iv) Fully fermented Nouricel |
|---|---|---|
| Gene Name | | |
| COL1A1 | 2.914 | 1.388 |
| COL1A2 | 3.2 | 2.102 |
| COL4A1 | 0.957 | 0.714 |
| VEGFB | 1.223 | 1.339 |
| TGF-Beta1 | 1.795 | 1.615 |
| FGF3 | 2.284 | 1.867 |
| PDGFRB | 2.194 | 1.773 |
| TJP1 | 2.302 | 1.804 |
| HSP90AB1 | 1.965 | 1.921 |
| HSP90A1 | 2.871 | 2.05 |
| HSPB1 | 1.947 | 1.881 |
| ELN | 1.554 | 0.526 |
| FN1 | 2.667 | 1.903 |
| PLOD1 | 0.709 | 0.463 |
| TIMP1 | 2.832 | 1.547 |
| SOD1 | 1.313 | 1.613 |
| MMP3 | 0.601 | 0.660 |
| MMP12 | 0.364 | 0.428 |
| SOD2 | 1.293 | 2.594 |
| CAT | 0.696 | 0.291 |

In one embodiment, the administration of the metabolized conditioned growth medium or the metabolized cell extract to a subject results in the up-regulation of at least one extracellular matrix protein. In some embodiments, the extracellular matrix protein is up-regulated by about 5% to about 100%, about 10% to about 90%, about 20% to about 80%, about 30% to about 70%, about 40% to about 60%, or about 25% to about 50%. In other embodiments, the extracellular matrix protein is up-regulated by about 10% to about 50% or about 60% to about 100%. In yet another embodiment, the extracellular matrix protein is up-regulated by about 5%, by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95% or by about 100%. In some embodiments, the extracellular matrix protein that is up-regulated is a collagen or lysyl hydroxylase protein. In some embodiments, the extracellular matrix protein is encoded by COL4A1 or PLOD1.

In one embodiment, the administration of the metabolized conditioned growth medium or the metabolized cell extract to a subject results in the up-regulation of at least one repair protein. In some embodiments, the repair protein is up-regulated by about 5% to about 100%, about 10% to about 90%, about 20% to about 80%, about 30% to about 70%, about 40% to about 60%, or about 25% to about 50%. In other embodiments, the repair protein is up-regulated by about 10% to about 70%. In some embodiments, the repair-protein is up-regulated by about 5%, by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95% or by about 100%. In some embodiments, the repair protein is fibronectin. In some embodiments, the repair protein is encoded by FN1.

In one embodiment, the administration of the metabolized conditioned growth medium or the metabolized cell extract to a subject results in the up-regulation of at least one cellular connectivity protein. In one embodiment, the cellular connectivity protein is up-regulated by about 5% to about 200%. In one embodiment, the cellular connectivity protein is up-regulated by about 10% to about 80%. In some embodiments, the cellular connectivity protein is up-regulated by about 30% to about 50%. In one embodiment, the cellular connectivity protein is up-regulated by about 5%, by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95%, by about 100%, by about 110%, by about 120%, by about 130%, by about 140%, by about 150%, by about 160%, by about 170%, by about 180%, by about 190% or by about 200%. In other embodiments, the cellular connectivity protein is involucrin protein. In some embodiments, the cellular connectivity protein is encoded by IVL gene.

In one embodiment, the administration of the metabolized conditioned growth medium or the metabolized cell extract to a subject results in the up-regulation of at least one antioxidant protein. In some embodiments, the antioxidant protein is up-regulated by about 5% to about 300%, about 5% to about 200%, about 5% to about 150%, about 5% to about 100%, about 10% to about 90%, about 20% to about 80%, about 30% to about 70%, about 40% to about 60%, or about 25% to about 50%. In other embodiments, the antioxidant protein is up-regulated by about 10% to about 50% or about 200% to about 250%. In some embodiments, the antioxidant protein is up-regulated by about 5%, by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95%, by about 100%, by about 125%, by about 150%, by about 175%, by about 200%, by about 250% or by about 300%. In some embodiments, the antioxidant protein that is up-regulated is superoxide dismutase. In some embodiments, the antioxidant protein that is up-regulated is encoded by SOD2.

Example 18: In Vitro and Clinical Studies

Patients and Methods

Methods: In Vitro Study

Gene Array Analysis

Human dermal fibroblasts were seeded into either a 96-well plate (cytotoxicity assay) or into T-25 flasks (cytokine array) and grown at 37±2° C. and 5±1% $CO_2$ using fibroblast growth media (FGM). Safe working concentration for each test material was determined using an MTT assay. Upon reaching confluence, the cells were treated with the test materials for 24 hours. After the 24 hour treatment, total RNA was isolated using an RNAqueous® Kit (Ambion) per the manufacturer's instructions. After purification, the total RNA was prepared for array use by first amplifying the RNA using a MessageAmp™ aRNA Kit (Ambion), and then fluorescently labeling the aRNA with Cy3 or Cy5 using an ASAP Labeling Kit (Perkin Elmer), both per the manufacturer's instructions. The fluorescently labeled aRNA was applied to the DNA microarray chips (Agilent Technologies) and the chips were hybridized overnight and washed per the manufacturer's recommended protocol. After washing, the microarrays were scanned with an Axon GenePix 4100A Scanner and analyzed with GenePix Pro software. Fluorescence intensities for the microarrays were subjected to global normalization. The total fluorescent signal for both dyes was normalized with a correction factor that would make the ratio of total intensities for both dyes equal to one. For this study a Cy3/Cy5 (untreated/treated) fluorescence intensity ratio greater than 1.3 or less than 0.7 (this relates to a change in gene expression of at least 30%) was used as the cutoff for up- and down-regulated genes, respectively. In addition, the fluorescence intensity of the gene marker had to be greater than the background intensity.

Protein Array Analysis

Human dermal fibroblasts were seeded into either a 96-well plate (cytotoxicity assay) or into T-25 flasks (cytokine array) and grown at 37±2° C. and 5±1% CO2 using fibroblast growth media (FGM). Safe working concentration for each test material was determined using an MTT assay. Upon reaching confluence the cells were treated with the test materials for 24 hours, after which cytokine release into the culture media was assessed using cytokine arrays (Ray Biotechnology). The microarrays were scanned with an Axon GenePix 4100A Scanner analyzed with GenePix Pro software.

Methods: 12-Week, Clinical-Usage Study (Combination Product)

A 12-week open-label clinical study examined the efficacy and tolerability of the combination treatment serum in subjects with mild to severe facial photodamage. The criteria for study participation included female subjects aged 30 to 60 years (having a Fitzpatrick Skin Phototype of I-IV) with clinically-determined mild to severe, fine and coarse wrinkles in the periocular area. Subjects were excluded from the study if they had used topical retinoids within 3 months of the study start, received injections of dermal fillers or botulinum toxin or had facial peels or had facial resurfacing procedures within 6 months or used other forms of anti-aging products on the face within 30 days of study start. Subjects with known allergies to the facial product regimen were also excluded.

Subjects were instructed to apply the treatment serum on their entire facial skin, twice daily (morning and evening) for twelve weeks. In addition to the treatment serum, subjects agreed to the use of a basic skincare regimen, including a cleanser, light moisturizer and sunscreen. Subjects also agreed not to begin the usage of any new facial products other than the provided materials for the duration of the study.

IRB approval was obtained for this open-label, single-center study from IntegReview of Austin, Tex. The study was conducted according to ethical and regulatory principals from the International Conference on Harmonization and good clinical practices.

Clinical evaluations were conducted at baseline (Visit 1), week 4 (Visit 2), week 8 (Visit 3) and week 12 (Visit 4). The following procedures were conducted at each visit.

Efficacy Assessments:

Fine and coarse wrinkles were clinically graded using a ten point scale, on each subject's right and left periocular area (where 0=none, 0.5-3.5=mild, 4-6.5=moderate and 7-9=severe). Ten point scales were also used to assess skin tactile roughness (where 0=smooth, 9=rough), skin tone (0=blotchy/uneven, 9=clear/even), skin firmness (where 0=skin appears loose and sags, 9=skin appears firm) and skin radiance (0=dull/flat matte, 9=bright/luminous/radiant). All grading assessments were performed by the same investigator at each visit to ensure grading consistency.

Safety Assessments:

Tolerability of the treatment product was assessed at all visits by the reporting of adverse events and by objective and subjective assessments. Objective irritation (erythema, edema and scaling) was assessed by the investigator whereas subjective irritation (burning/stinging, itching and tingling) was assessed by the subject, all using a 4-point scale (where 0=none, 1=mild, 2=moderate and 3=severe).

Standardized Photography:

Standardized, digital images were taken of the subject's left, right and frontal facial views using raking light (standard color).

Self-Assessment Questionnaires:

Subjects completed a Self-Assessment Questionnaire at Week 12, where they rated their facial skin condition and the treatment serum's efficacy on a four point scale (Strongly Agree, Agree, Disagree, Strongly Disagree). Subjects rated their overall satisfaction with the treatment serum on a four point scale where 1=Excellent, 2=Good, 3=Fair and 4=Poor.

Statistical Analysis:

Mean clinical grading scores at weeks 4, 8 and 12 were compared to mean baseline scores using a student's paired t-test. Changes from baseline were considered significant at the $p<0.05$ level. For the subject Self-Assessment Questionnaires, the percent incidence of positive responders was reported for the treatment serum's efficacy and aesthetic attributes sections.

Results

Results: In Vitro Study

After treatment of human dermal fibroblasts with Biometa Complex (yeast metabolized conditioned growth media), the gene expression profiled was analyzed with a special emphasis on genes implicated in the anti-aging cascade. The following Table lists some of the key genes regulated by Biometa complex: Biometa complex stimulates a number of genes involved in the extracellular matrix regeneration.

| Function | Genes | Brief Description |
| --- | --- | --- |
| Extracellular Matrix Proteins | Col 1A1, COL12A1, COL15A1, | Genes encoding collagen |
| Growth Factors and Cytokines involved in repair and ECM production | TGF-Beta | Induces synthesis and secretion of major extracellular matrix proteins, collagen and elastin |
| | TIMP1/TIMP3 | TIMPs play an important role in the regulation of MMP activity |
| | VEGF-A/VEGF-B | Key role in angiogenesis |
| | FGF3 | Enhanced hyaluronan production and implications in tissue remodeling |
| | PDGFRB | Implicated in tissue remodeling |
| | IGF | Enhanced hyaluronan production and implications in tissue remodeling |
| | IL-10RB, IL-11, IL-8, etc. | Involved in several signal transduction pathways that include tissue remodeling, etc |
| Antioxidant | SOD1 | involved in regulation of ROS-mediated tissue damage; usually found in the extracellular matrix and is ideally situated to prevent cell and tissue damage initiated by reactive oxygen species (ROS) |
| Stress Related | HSP | Heat shock proteins are part of cellular defense against stress |
| Skin Barrier | TJP1/ZO-1 | Help improve skin barrier function |

Additionally we saw a down-regulation of MMP (enzyme responsible for breaking down collagen and elastin). This down-regulation of MMP correlated well with an upregulation of TIMPS (a natural inhibitor of MMPs). Biometa complex has also upregulated other genes necessary to maintain the overall health of the skin including stress proteins (HSP), antioxidant proteins (SOD1), and proteins important for maintaining skin barrier (TJ1).

Biometa Complex also stimulated fibroblasts to express and synthesize key proteins (cytokines, growth factors, etc.) known to be involved in skin repair and remodeling including bFGF (Fibroblast Growth Factor), TIMP-1 (Tissue inhibitor of Metalloproteinases), and VEGF (Vascular endothelial growth factor) based on analysis of proteins released into medium after treatment. This data shows a good correlation between gene expression and protein synthesis. These results demonstrate that Biometa complex has the ability to stimulate fibroblasts, thereby reducing signs of aging.

Results: 12 Week Clinical-Usage Study

Thirty-three female subjects aged 35-56 years with mild to severe, fine and coarse periocular wrinkles were enrolled and completed the twelve week study.

Figure 4:
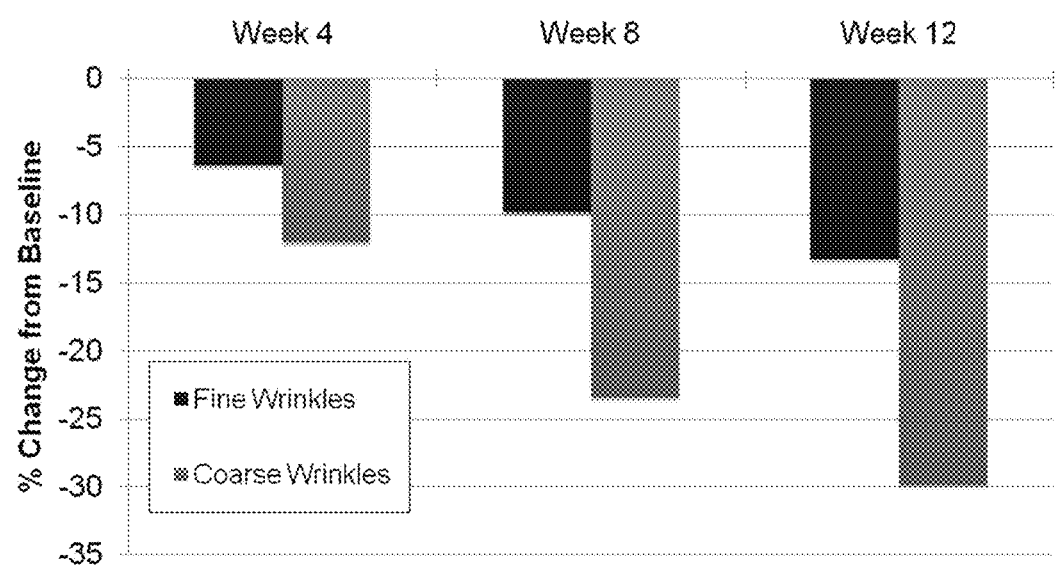
FIG. 4 is a graph demonstrating investigator assessments of fine and coarse wrinkles Significant reductions in mean scores were observed for fine and coarse wrinkles at all visits (all P<0.0001). In each data set, fine wrinkle assessment is shown on the left and coarse wrinkle assessment is shown in the right.
Figure 5:
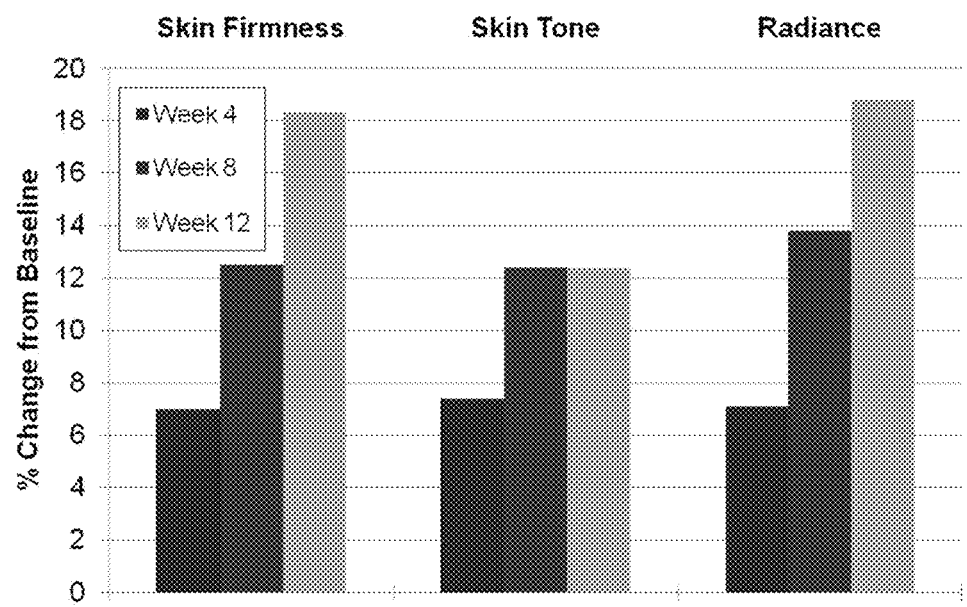
FIG. 5 a graph demonstrating investigator assessments of skin tone, firmness and radiance. Significant improvements in mean scores for skin firmness, skin tone and radiance at all visits (all P≤0.02). In each data set, week 4 results are shown on the left, week 8 results are shown in the middle and week 12 results are shown on the right.
Figure 6:
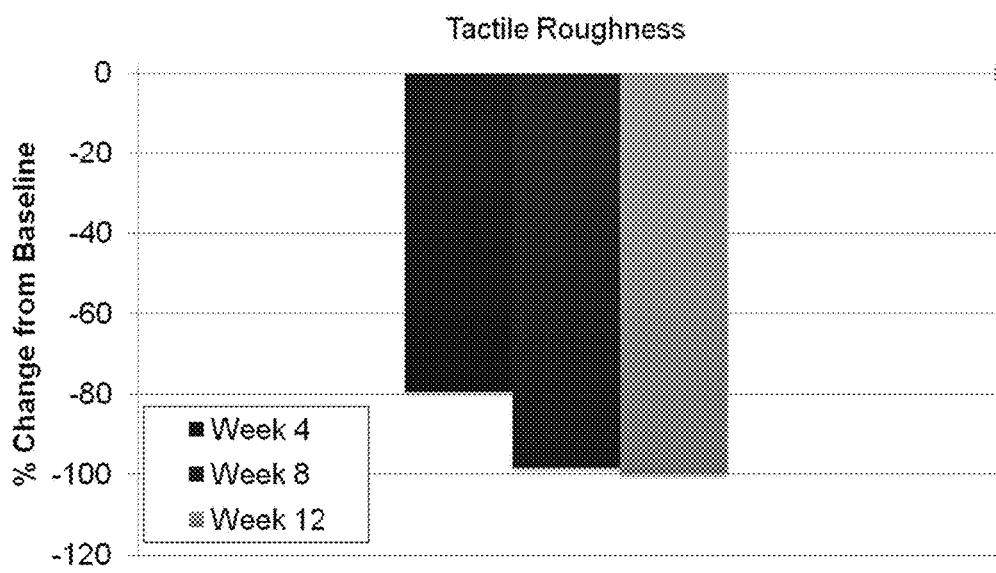
FIG. 6 is a graph demonstrating investigator assessments of tactile roughness. Significant improvements in mean scores for skin firmness, skin tone and radiance at all visits (all P<0.0001). Percent change from baseline at week 4 is shown in the left-hand column, week 8 in the middle column and week 12 in the right-hand column, respectively.

At weeks 4, 8 and 12, statistically significant improvements in mean scores for all photoaging parameters were achieved after twice-daily topical use of the combination treatment serum. Investigator assessments demonstrated significant reductions in mean scores for fine and coarse periocular wrinkles at week 4 with continued significant reductions through week 12 (all P<0.0001) as shown in FIG. 4. Most notably, mean scores for coarse periocular wrinkles decreased by 30% at week 12. In addition, mean scores for skin firmness, skin tone, radiance and tactile roughness reflected similar significant and progressive improvements from baseline and at all subsequent follow-up visits (all P≤0.02) as depicted in FIG. 5 and FIG. 6. Especially prominent was the improvement in the texture of the skin achieved as early as week 4, shown by a significant reduction (79.5%) in mean tactile roughness scores (P<0.0001).

Figure 7:
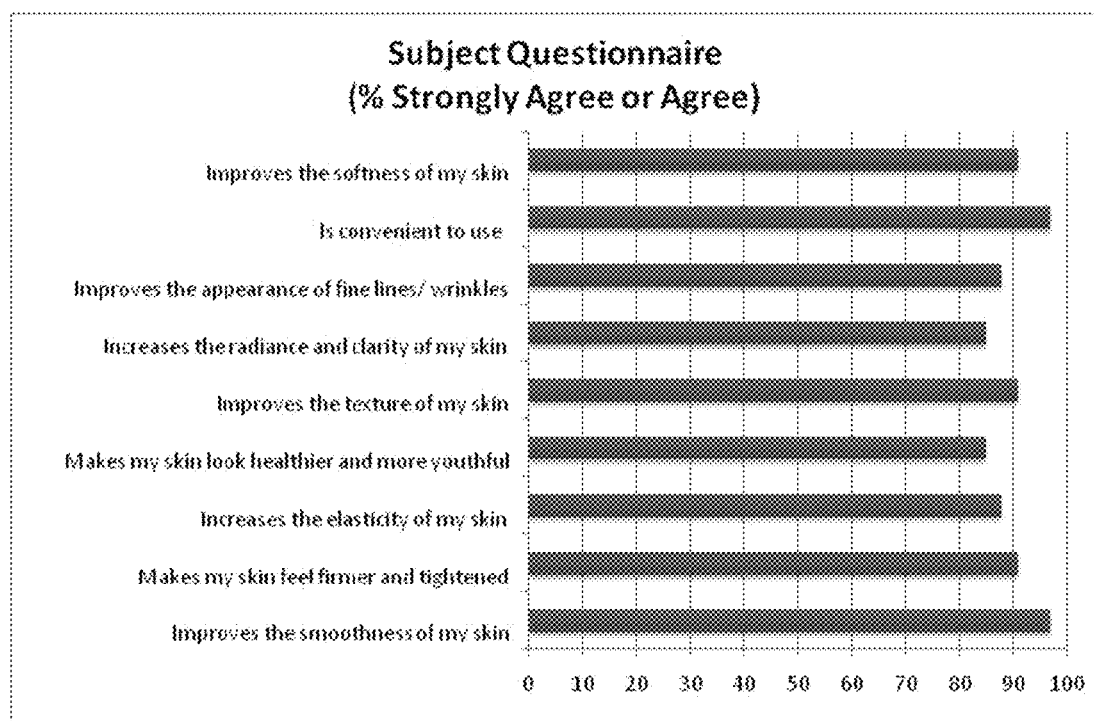
FIG. 7 is a graph providing the results at week 12 of a subject self-assessment questionnaire from the 12-week clinical usage (Combined/Combination Product) study described in Example 18.

The subject responses in the Self-Assessment Questionnaire at week 12 strongly support the improvements observed in the investigator assessments, with over 85% of subjects responding favorably to all questions. The percentage of subjects who selected Strongly Agree or Agree in response to the questionnaire at Week 12 are presented in FIG. 7.

Standardized digital photographs (data not shown) represent examples of clinical responses after twice-daily use of the combination treatment serum. Briefly, improvements in peri-ocular fine and coarse wrinkles and skin tone were demonstrated in a 49 year old Caucasian female subject after only four weeks of product use. In addition, a 46 year old Hispanic female subject showed visible improvements in fine peri-ocular wrinkles, skin tone, tactile roughness and radiance at week 4. A 46 year old Korean/Caucasian female subject presenting with fine and coarse peri-ocular wrinkles and uneven skin tone visibly improved after four weeks of product use.

The combination treatment serum was well-tolerated and there were no treatment-related adverse events reported during the course of the study. Mean scores for edema, scaling, burning/stinging, itching and tingling remained less than mild throughout the study (all scores <0.09 on the 0-4 scale). Notably, mean scores for erythema decreased from baseline at all follow-up visits, with a statistically significant decrease observed at week 8 (P<0.03).

CONCLUSION

This treatment serum provides physicians and patients with a unique and effective topical combination product that improves signs of skin aging.

The present disclosure is not to be limited in scope by the specific embodiments described herein. Indeed, various modifications in addition to those described will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A process for preparing a topical composition, the process comprising:
    (a) culturing cells derived from mammalian cells, mammalian skin cells or mammalian fibroblasts in a growth medium sufficient to meet the nutritional needs required to grow the cells in vitro to form a conditioned growth medium and removing the conditioned growth medium from the cultured cells;
    (b) culturing yeast cells;
    (c) exposing the cultured yeast cells to the conditioned growth medium;
    (d) further culturing the cultured yeast cells to metabolize at least a portion of the conditioned growth medium
    (e) collecting the metabolized conditioned growth medium; and
    (f) combining the metabolized conditioned growth medium with at least one excipient to form a topical composition in a form selected from the group consisting of a lotion, cream, ointment, gel, hydrogel, oil or emulsion.

2. The process of claim 1, wherein the collected metabolized conditioned growth medium of step (e) is concentrated, filtered and/or purified.

* * * * *